US011517749B2

(12) United States Patent
Sharma

(10) Patent No.: US 11,517,749 B2
(45) Date of Patent: *Dec. 6, 2022

(54) METHODS AND APPARATUSES FOR STIMULATING BLOOD VESSELS IN ORDER TO CONTROL, TREAT, AND/OR PREVENT A HEMORRHAGE

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 247 days.

This patent is subject to a terminal disclaimer.

(21) Appl. No.: 16/793,085

(22) Filed: Feb. 18, 2020

(65) Prior Publication Data

US 2020/0269039 A1 Aug. 27, 2020

Related U.S. Application Data

(60) Division of application No. 15/451,629, filed on Mar. 7, 2017, now Pat. No. 10,603,489, which is a (Continued)

(51) Int. Cl.
*A61N 1/36* (2006.01)
*A61N 1/05* (2006.01)

(52) U.S. Cl.
CPC .............. *A61N 1/36* (2013.01); *A61N 1/05* (2013.01); *A61N 1/0509* (2013.01);
(Continued)

(58) Field of Classification Search
CPC .......... A61N 1/36; A61N 1/05; A61N 1/0509; A61N 1/0556; A61N 1/36007; A61N 1/3606; A61N 1/36114; A61N 1/36117
See application file for complete search history.

(56) References Cited

U.S. PATENT DOCUMENTS 1,696,018 A 12/1928 Schellberg
3,628,538 A 12/1971 Vincent
(Continued)

FOREIGN PATENT DOCUMENTS

AU 2012242533 B2 11/2013
AU 2012250686 B2 11/2013
(Continued)

OTHER PUBLICATIONS

International Search Report for PCT/US2008/053780, dated Jun. 8, 2009.
(Continued)

*Primary Examiner* — Mallika D Fairchild
(74) *Attorney, Agent, or Firm* — Novel IP

(57) ABSTRACT

Methods of preventing, treating, and/or controlling a hemorrhage in an organ of a patient include providing electrical stimulation to the arteries, veins, nerves innervating the arteries or veins, or walls of the organ. The apparatus has at least one electrode operably connected to a stimulus generator and placed in electrical communication with an artery, vein, nerve, or organ wall. An electrical stimulus generator causes an electrical stimulus to be administered to the artery, vein, nerve, or wall through the at least one electrode, where the electrical stimulus is effective for preventing, treating, and/or controlling a hemorrhage.

8 Claims, 50 Drawing Sheets

Related U.S. Application Data continuation-in-part of application No. 14/728,630, filed on Jun. 2, 2015, now Pat. No. 9,656,068, which is a continuation of application No. 12/575,713, filed on Oct. 8, 2009, now Pat. No. 9,079,028.

(60) Provisional application No. 62/328,303, filed on Apr. 27, 2016, provisional application No. 62/304,841, filed on Mar. 7, 2016, provisional application No. 61/104,054, filed on Oct. 9, 2008.

(52) U.S. Cl.
CPC ......... *A61N 1/0556* (2013.01); *A61N 1/3606* (2013.01); *A61N 1/36007* (2013.01); *A61N 1/36114* (2013.01); *A61N 1/36117* (2013.01)

(56) References Cited

U.S. PATENT DOCUMENTS

| | | |
|---|---|---|
| 3,776,221 A | 12/1973 | Mc Intyre |
| 3,814,080 A | 6/1974 | Norman |
| 3,866,613 A | 2/1975 | Kenny |
| 3,910,281 A | 10/1975 | Kletschka |
| 3,916,875 A | 11/1975 | Toch |
| 3,938,502 A | 2/1976 | Bom |
| 4,106,511 A | 8/1978 | Erlandsson |
| 4,153,059 A | 5/1979 | Fravel |
| 4,222,377 A | 9/1980 | Burton |
| 4,406,288 A | 9/1983 | Horwinski |
| 4,571,749 A | 2/1986 | Fischell |
| 4,580,578 A | 4/1986 | Barsom |
| 4,607,639 A | 8/1986 | Tanagho |
| 4,731,083 A | 3/1988 | Fischell |
| 4,739,764 A | 4/1988 | Lue |
| 4,785,828 A | 11/1988 | Maurer |
| 4,792,330 A | 12/1988 | Lazarus |
| 4,846,191 A | 7/1989 | Brockway |
| 4,886,070 A | 12/1989 | Demarest |
| 4,957,484 A | 9/1990 | Murtfeldt |
| 5,188,104 A | 2/1993 | Wernicke |
| 5,231,988 A | 8/1993 | Wernicke |
| 5,263,480 A | 11/1993 | Wernicke |
| 5,290,231 A | 3/1994 | Marcadis |
| 5,305,745 A * | 4/1994 | Zacouto ............ A61B 17/22 600/324 |
| 5,345,927 A | 9/1994 | Bonutti |
| 5,387,231 A | 2/1995 | Sporer |
| 5,391,143 A | 2/1995 | Kensey |
| 5,411,535 A * | 5/1995 | Fujii ............ A61N 1/0587 128/903 |
| 5,423,872 A | 6/1995 | Cigaina |
| 5,437,284 A | 8/1995 | Trimble |
| 5,477,860 A | 12/1995 | Essen-Moller |
| 5,484,445 A | 1/1996 | Knuth |
| 5,505,201 A | 4/1996 | Grill, Jr. |
| 5,540,658 A | 7/1996 | Evans |
| 5,556,422 A | 9/1996 | Powell, III |
| 5,562,717 A | 10/1996 | Tippey |
| 5,590,649 A | 1/1997 | Caro |
| 5,617,873 A | 4/1997 | Yost |
| 5,655,548 A | 8/1997 | Nelson |
| 5,690,691 A | 11/1997 | Chen |
| 5,702,428 A | 12/1997 | Tippey |
| 5,713,371 A | 2/1998 | Sherman |
| 5,836,994 A | 11/1998 | Bourgeois |
| 5,861,014 A | 1/1999 | Familoni |
| 5,861,044 A | 1/1999 | Crenshaw |
| 5,865,744 A | 2/1999 | Lemelson |
| 5,927,282 A | 7/1999 | Lenker |
| 5,954,714 A | 9/1999 | Saadat |
| 5,968,010 A | 10/1999 | Waxman |
| 5,984,854 A | 11/1999 | Ishikawa |
| 6,002,964 A | 12/1999 | Feler |
| 6,024,704 A | 2/2000 | Meador |
| 6,041,258 A | 3/2000 | Cigaina |
| 6,097,984 A | 8/2000 | Douglas |
| 6,106,477 A | 8/2000 | Miesel |
| 6,112,123 A | 8/2000 | Kelleher |
| 6,115,637 A | 9/2000 | Lennox |
| 6,129,685 A | 10/2000 | Howard, III |
| 6,131,575 A | 10/2000 | Lenker |
| 6,135,945 A | 10/2000 | Sultan |
| 6,210,346 B1 | 4/2001 | Hall |
| 6,238,389 B1 | 5/2001 | Paddock |
| 6,238,423 B1 | 5/2001 | Bardy |
| 6,240,315 B1 | 5/2001 | Mo |
| 6,243,607 B1 | 6/2001 | Mintchev |
| 6,272,370 B1 | 8/2001 | Gillies |
| 6,292,695 B1 | 9/2001 | Webster |
| 6,299,583 B1 | 10/2001 | Eggers |
| 6,321,109 B2 | 11/2001 | Ben-Haim |
| 6,321,124 B1 | 11/2001 | Cigaina |
| 6,338,718 B1 | 1/2002 | Ogura |
| 6,364,834 B1 | 4/2002 | Reuss |
| 6,368,274 B1 | 4/2002 | Van Antwerp |
| 6,370,417 B1 | 4/2002 | Horbaschek |
| 6,383,142 B1 | 5/2002 | Gavriely |
| 6,428,467 B1 | 8/2002 | Benderev |
| 6,449,511 B1 | 9/2002 | Mintchev |
| 6,475,223 B1 | 11/2002 | Werp |
| 6,510,332 B1 | 1/2003 | Greenstein |
| 6,535,764 B2 | 3/2003 | Imran |
| 6,542,776 B1 | 4/2003 | Gordon |
| 6,569,012 B2 | 5/2003 | Lydon |
| 6,587,719 B1 | 7/2003 | Barrett |
| 6,591,137 B1 | 7/2003 | Fischell |
| 6,606,523 B1 | 8/2003 | Jenkins |
| 6,609,025 B2 | 8/2003 | Barrett |
| 6,611,715 B1 | 8/2003 | Boveja |
| 6,612,977 B2 | 9/2003 | Staskin |
| 6,615,084 B1 | 9/2003 | Cigaina |
| 6,658,297 B2 | 12/2003 | Loeb |
| 6,659,936 B1 | 12/2003 | Furness |
| 6,676,686 B2 | 1/2004 | Naganuma |
| 6,678,557 B1 | 1/2004 | Tumey |
| 6,684,104 B2 | 1/2004 | Gordon |
| 6,685,729 B2 | 2/2004 | Gonzalez |
| 6,735,474 B1 | 5/2004 | Loeb |
| 6,741,882 B2 | 5/2004 | Schaeffter |
| 6,749,607 B2 | 6/2004 | Edwards |
| 6,761,631 B2 | 7/2004 | Lydon |
| 6,826,428 B1 | 11/2004 | Chen |
| 6,832,114 B1 | 12/2004 | Whitehurst |
| 6,837,886 B2 | 1/2005 | Collins |
| 6,845,776 B2 | 1/2005 | Stack |
| 6,865,416 B2 | 3/2005 | Dev |
| 6,879,859 B1 | 4/2005 | Boveja |
| 6,889,076 B2 | 5/2005 | Cigaina |
| 6,895,278 B1 | 5/2005 | Gordon |
| 6,901,295 B2 | 5/2005 | Sharma |
| 6,905,496 B1 | 6/2005 | Ellman |
| 6,911,003 B2 | 6/2005 | Anderson |
| 6,915,165 B2 | 7/2005 | Forsell |
| 6,918,873 B1 | 7/2005 | Millar |
| 6,934,583 B2 | 8/2005 | Weinberg |
| 6,947,792 B2 | 9/2005 | Ben-Haim |
| 6,950,707 B2 | 9/2005 | Whitehurst |
| 6,960,203 B2 | 11/2005 | Xiao |
| 6,961,621 B2 | 11/2005 | Krishnan |
| 6,970,746 B2 | 11/2005 | Eckmiller |
| 7,006,871 B1 | 2/2006 | Darvish |
| 7,025,762 B2 | 4/2006 | Johnston |
| 7,054,689 B1 | 5/2006 | Whitehurst |
| 7,054,690 B2 | 5/2006 | Imran |
| 7,076,306 B2 | 7/2006 | Marchal |
| 7,087,053 B2 | 8/2006 | Vanney |
| 7,120,498 B2 | 10/2006 | Imran |
| 7,177,693 B2 | 2/2007 | Starkebaum |
| 7,194,301 B2 | 3/2007 | Jenkins |
| 7,200,443 B2 | 4/2007 | Faul |
| 7,299,091 B2 | 11/2007 | Barrett |
| 7,310,557 B2 | 12/2007 | Maschino |
| 7,320,675 B2 | 1/2008 | Pastore |

(56) References Cited

U.S. PATENT DOCUMENTS

| | | |
|---|---|---|
| 7,324,852 B2 | 1/2008 | Barolat |
| 7,340,306 B2 | 3/2008 | Barrett |
| 7,373,204 B2 * | 5/2008 | Gelfand ............ A61N 1/36114 607/2 |
| 7,418,292 B2 | 8/2008 | Shafer |
| 7,445,630 B2 | 11/2008 | Lashinski |
| 7,481,759 B2 | 1/2009 | Whitehurst |
| 7,519,421 B2 | 4/2009 | Denker |
| 7,526,337 B2 | 4/2009 | Shuros |
| 7,551,964 B2 | 6/2009 | Dobak, III |
| 7,596,413 B2 | 9/2009 | Libbus |
| 7,632,234 B2 | 12/2009 | Manda |
| 7,653,438 B2 | 1/2010 | Deem |
| 7,664,548 B2 | 2/2010 | Amurthur |
| 7,689,276 B2 | 3/2010 | Dobak |
| 7,734,341 B2 | 6/2010 | Shuros |
| 7,738,961 B2 | 6/2010 | Sharma |
| 7,761,166 B2 | 7/2010 | Giftakis |
| 7,765,006 B2 | 7/2010 | Martino |
| 7,765,007 B2 | 7/2010 | Martino |
| 7,803,195 B2 | 9/2010 | Levy |
| 7,844,338 B2 | 11/2010 | Knudson |
| 7,881,797 B2 | 2/2011 | Griffin |
| 7,894,906 B2 | 2/2011 | Shuros |
| 7,901,419 B2 | 3/2011 | Bachmann |
| 7,917,208 B2 | 3/2011 | Yomtov |
| 7,941,221 B2 | 5/2011 | Foley |
| 8,007,507 B2 | 8/2011 | Waller |
| 8,024,035 B2 | 9/2011 | Dobak |
| 8,126,538 B2 | 2/2012 | Shuros |
| 8,160,709 B2 | 4/2012 | Soffer |
| 8,346,482 B2 | 1/2013 | Fernandez |
| 8,447,403 B2 | 5/2013 | Sharma |
| 8,447,404 B2 | 5/2013 | Sharma |
| 8,538,534 B2 | 9/2013 | Soffer |
| 8,543,210 B2 | 9/2013 | Sharma |
| 8,594,811 B2 | 11/2013 | Chen |
| 8,628,554 B2 | 1/2014 | Sharma |
| 8,706,234 B2 | 4/2014 | Sharma |
| 8,712,529 B2 | 4/2014 | Sharma |
| 8,712,530 B2 | 4/2014 | Sharma |
| 8,761,903 B2 | 6/2014 | Chen |
| 8,798,753 B2 | 8/2014 | Sharma |
| 8,831,729 B2 | 9/2014 | Policker |
| 8,868,190 B2 | 10/2014 | Guez |
| 9,020,597 B2 | 4/2015 | Sharma |
| 9,037,244 B2 | 5/2015 | Sharma |
| 9,037,245 B2 | 5/2015 | Sharma |
| 9,061,147 B2 | 6/2015 | Sharma |
| 9,079,028 B2 | 7/2015 | Sharma |
| 9,345,879 B2 | 5/2016 | Sharma |
| 9,381,344 B2 | 7/2016 | Sharma |
| 9,498,619 B2 | 11/2016 | Goode |
| 9,561,367 B2 | 2/2017 | Sharma |
| 9,616,225 B2 | 4/2017 | Sharma |
| 9,623,238 B2 | 4/2017 | Sharma |
| 9,656,068 B2 | 5/2017 | Sharma |
| 9,682,234 B2 | 6/2017 | Hogg |
| 9,724,510 B2 | 8/2017 | Sharma |
| 9,782,583 B2 | 10/2017 | Sharma |
| 9,789,309 B2 | 10/2017 | Sharma |
| 9,827,425 B2 | 11/2017 | Glasberg |
| 9,925,367 B2 | 3/2018 | Sharma |
| 9,950,160 B2 | 4/2018 | Sharma |
| 10,376,694 B2 | 8/2019 | Sharma |
| 10,603,489 B2 | 3/2020 | Sharma |
| 2001/0041831 A1 | 11/2001 | Starkweather |
| 2001/0041870 A1 | 11/2001 | Gillis |
| 2002/0016615 A1 | 2/2002 | Dev |
| 2002/0029037 A1 | 3/2002 | Kim |
| 2002/0072780 A1 | 6/2002 | Foley |
| 2002/0123674 A1 | 9/2002 | Plicchi |
| 2002/0161382 A1 | 10/2002 | Neisz |
| 2002/0165589 A1 | 11/2002 | Imran |
| 2002/0177846 A1 | 11/2002 | Mulier |
| 2002/0188253 A1 | 12/2002 | Gordon |
| 2003/0014086 A1 | 1/2003 | Sharma |
| 2003/0028232 A1 | 2/2003 | Camps |
| 2003/0036773 A1 | 2/2003 | Whitehurst |
| 2003/0040808 A1 | 2/2003 | Stack |
| 2003/0055466 A1 | 3/2003 | Ben-Haim |
| 2003/0060848 A1 | 3/2003 | Kieval |
| 2003/0088145 A1 | 5/2003 | Scott |
| 2003/0109935 A1 | 6/2003 | Geitz |
| 2003/0113303 A1 | 6/2003 | Schwartz |
| 2003/0114895 A1 | 6/2003 | Gordon |
| 2003/0120321 A1 | 6/2003 | Bumm |
| 2003/0144708 A1 | 7/2003 | Starkebaum |
| 2003/0195600 A1 | 10/2003 | Tronnes |
| 2003/0204185 A1 | 10/2003 | Sherman |
| 2003/0216729 A1 | 11/2003 | Marchitto |
| 2004/0015201 A1 | 1/2004 | Greenstein |
| 2004/0037986 A1 | 2/2004 | Houston |
| 2004/0039453 A1 | 2/2004 | Anderson |
| 2004/0044376 A1 | 3/2004 | Flesler |
| 2004/0059393 A1 | 3/2004 | Policker |
| 2004/0073453 A1 | 4/2004 | Nenov |
| 2004/0088022 A1 | 5/2004 | Chen |
| 2004/0102804 A1 | 5/2004 | Chin |
| 2004/0102818 A1 * | 5/2004 | Hakky .................. A61N 1/32 607/44 |
| 2004/0147976 A1 | 7/2004 | Gordon |
| 2004/0158297 A1 | 8/2004 | Gonzalez |
| 2004/0167583 A1 | 8/2004 | Knudson |
| 2004/0172085 A1 | 9/2004 | Knudson |
| 2004/0172102 A1 | 9/2004 | Leysieffer |
| 2004/0186544 A1 | 9/2004 | King |
| 2004/0193229 A1 | 9/2004 | Starkebaum |
| 2004/0210118 A1 | 10/2004 | Letort |
| 2004/0220682 A1 | 11/2004 | Levine |
| 2004/0230188 A1 | 11/2004 | Cioanta |
| 2004/0236382 A1 | 11/2004 | Dinsmoor |
| 2004/0236385 A1 | 11/2004 | Rowe |
| 2004/0243152 A1 | 12/2004 | Taylor |
| 2005/0070974 A1 | 3/2005 | Knudson |
| 2005/0075702 A1 | 4/2005 | Shafer |
| 2005/0095168 A1 | 5/2005 | Centanni |
| 2005/0113878 A1 | 5/2005 | Gerber |
| 2005/0143787 A1 | 6/2005 | Boveja |
| 2005/0149014 A1 | 7/2005 | Hauck |
| 2005/0149142 A1 | 7/2005 | Starkebaum |
| 2005/0149157 A1 | 7/2005 | Hunter |
| 2005/0160395 A1 | 7/2005 | Hughes |
| 2005/0187584 A1 | 8/2005 | Denker |
| 2005/0192642 A1 | 9/2005 | Forsell |
| 2005/0216069 A1 | 9/2005 | Cohen |
| 2005/0222637 A1 | 10/2005 | Chen |
| 2005/0222638 A1 | 10/2005 | Foley |
| 2005/0240239 A1 | 10/2005 | Boveja |
| 2005/0251219 A1 | 11/2005 | Evans |
| 2005/0256587 A1 | 11/2005 | Egan |
| 2005/0267440 A1 | 12/2005 | Herman |
| 2006/0036237 A1 | 2/2006 | Davison |
| 2006/0036293 A1 | 2/2006 | Whitehurst |
| 2006/0064037 A1 | 3/2006 | Shalon |
| 2006/0074449 A1 * | 4/2006 | Denker .............. A61N 1/37516 607/116 |
| 2006/0074453 A1 | 4/2006 | Kieval |
| 2006/0085042 A1 * | 4/2006 | Hastings ............ A61N 1/37223 607/33 |
| 2006/0106442 A1 | 5/2006 | Richardson |
| 2006/0116736 A1 | 6/2006 | Dilorenzo |
| 2006/0161217 A1 | 7/2006 | Jaax |
| 2006/0167498 A1 | 7/2006 | Dilorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0287678 A1 | 12/2006 | Shafer |
| 2007/0016262 A1 | 1/2007 | Gross |
| 2007/0016274 A1 | 1/2007 | Boveja |
| 2007/0021650 A1 | 1/2007 | Rocheleau |
| 2007/0021731 A1 | 1/2007 | Garibaldi |
| 2007/0027484 A1 | 2/2007 | Guzman |

(56) References Cited

U.S. PATENT DOCUMENTS

| | | |
|---|---|---|
| 2007/0038259 A1* | 2/2007 | Kieval .............. A61N 1/36114 607/44 |
| 2007/0100367 A1 | 5/2007 | Quijano |
| 2007/0106337 A1 | 5/2007 | Errico |
| 2007/0162085 A1 | 7/2007 | Dilorenzo |
| 2007/0185535 A1 | 8/2007 | Libbus |
| 2007/0238942 A1 | 10/2007 | Baylor |
| 2007/0244520 A1 | 10/2007 | Ferren |
| 2007/0276293 A1 | 11/2007 | Gertner |
| 2007/0282376 A1 | 12/2007 | Shuros |
| 2007/0282410 A1 | 12/2007 | Cross |
| 2008/0004673 A1 | 1/2008 | Rossing |
| 2008/0021512 A1 | 1/2008 | Knudson |
| 2008/0039904 A1 | 2/2008 | Bulkes |
| 2008/0058887 A1 | 3/2008 | Griffin |
| 2008/0058891 A1 | 3/2008 | Ben-Haim |
| 2008/0065136 A1 | 3/2008 | Young |
| 2008/0097412 A1 | 4/2008 | Shuros |
| 2008/0097466 A1 | 4/2008 | Levine |
| 2008/0154191 A1 | 6/2008 | Gobel |
| 2008/0167699 A1 | 7/2008 | Kieval |
| 2008/0195171 A1 | 8/2008 | Sharma |
| 2008/0195174 A1 | 8/2008 | Walker |
| 2008/0208355 A1 | 8/2008 | Stack |
| 2008/0255678 A1 | 10/2008 | Cully |
| 2008/0281267 A1 | 11/2008 | Mehier |
| 2008/0294228 A1 | 11/2008 | Brooke |
| 2008/0300449 A1 | 12/2008 | Gerber |
| 2009/0005867 A1 | 1/2009 | Lefranc |
| 2009/0030475 A1 | 1/2009 | Brynelsen |
| 2009/0036945 A1 | 2/2009 | Chancellor |
| 2009/0054950 A1 | 2/2009 | Stephens |
| 2009/0062881 A1 | 3/2009 | Gross |
| 2009/0069803 A1 | 3/2009 | Starkebaum |
| 2009/0131993 A1 | 5/2009 | Rousso |
| 2009/0132001 A1 | 5/2009 | Soffer |
| 2009/0192570 A1 | 7/2009 | Jaax |
| 2009/0204063 A1 | 8/2009 | Policker |
| 2009/0222058 A1 | 9/2009 | Craggs |
| 2009/0222060 A1 | 9/2009 | Boyd |
| 2009/0228059 A1 | 9/2009 | Shuros |
| 2009/0264951 A1 | 10/2009 | Sharma |
| 2009/0281553 A1 | 11/2009 | Kalloo |
| 2010/0076254 A1 | 3/2010 | Jimenez |
| 2010/0094270 A1 | 4/2010 | Sharma |
| 2010/0094373 A1 | 4/2010 | Sharma |
| 2010/0114082 A1 | 5/2010 | Sharma |
| 2010/0114083 A1 | 5/2010 | Sharma |
| 2010/0256775 A1 | 10/2010 | Belhe |
| 2010/0324432 A1 | 12/2010 | Bjorling |
| 2011/0004266 A1 | 1/2011 | Sharma |
| 2011/0071589 A1 | 3/2011 | Starkebaum |
| 2011/0213437 A9 | 9/2011 | Armstrong |
| 2011/0307075 A1 | 12/2011 | Sharma |
| 2012/0150245 A1 | 6/2012 | Rezai |
| 2012/0232610 A1 | 9/2012 | Soffer |
| 2012/0265103 A1 | 10/2012 | Policker |
| 2013/0006231 A1 | 1/2013 | Sharma |
| 2013/0013084 A1 | 1/2013 | Birk |
| 2013/0030503 A1 | 1/2013 | Yaniv |
| 2013/0172882 A1 | 7/2013 | Hastings |
| 2013/0178912 A1 | 7/2013 | Sharma |
| 2013/0218229 A1 | 8/2013 | Sharma |
| 2013/0231660 A1 | 9/2013 | Edwards |
| 2013/0238066 A1 | 9/2013 | Boggs, II |
| 2013/0289446 A1 | 10/2013 | Stone |
| 2014/0058372 A1 | 2/2014 | Belson |
| 2014/0088664 A1 | 3/2014 | Sharma |
| 2014/0194917 A1 | 7/2014 | Sharma |
| 2014/0200568 A1 | 7/2014 | Sharma |
| 2014/0222106 A1 | 8/2014 | Sharma |
| 2014/0228911 A1 | 8/2014 | Sharma |
| 2014/0243593 A1 | 8/2014 | Goode |
| 2014/0243922 A1 | 8/2014 | Haessler |
| 2014/0276336 A1 | 9/2014 | Sharma |
| 2014/0309708 A1 | 10/2014 | Sharma |
| 2015/0018924 A1 | 1/2015 | Sharma |
| 2015/0057718 A1 | 2/2015 | Sharma |
| 2015/0066109 A1 | 3/2015 | Glasberg |
| 2015/0119646 A1 | 4/2015 | Sharma |
| 2015/0119869 A1 | 4/2015 | Sharma |
| 2015/0119952 A1 | 4/2015 | Sharma |
| 2015/0126990 A1 | 5/2015 | Sharma |
| 2015/0224310 A1 | 8/2015 | Sharma |
| 2015/0297885 A1 | 10/2015 | Goode |
| 2016/0030734 A1 | 2/2016 | Sharma |
| 2016/0303370 A1 | 10/2016 | Sharma |
| 2017/0021169 A1 | 1/2017 | Sharma |
| 2017/0036021 A1 | 2/2017 | Sharma |
| 2017/0128716 A1 | 5/2017 | Goode |
| 2017/0165483 A1 | 6/2017 | Sharma |
| 2017/0296813 A1 | 10/2017 | Sharma |
| 2017/0296814 A1 | 10/2017 | Sharma |
| 2017/0361092 A1 | 12/2017 | Sharma |
| 2018/0085576 A1 | 3/2018 | Sharma |
| 2018/0154135 A1 | 6/2018 | Goode |

FOREIGN PATENT DOCUMENTS

| | | |
|---|---|---|
| CN | 103648582 B | 3/2014 |
| DE | 21201110038 | 7/2012 |
| EP | 1504778 | 2/2005 |
| EP | 2542174 A2 | 1/2013 |
| EP | 2696792 B1 | 2/2014 |
| EP | 2704791 B1 | 3/2014 |
| EP | 2888000 A2 | 7/2015 |
| EP | 3041564 A2 | 7/2016 |
| EP | 3071289 A1 | 9/2016 |
| EP | 3071291 A1 | 9/2016 |
| EP | 3103509 A1 | 12/2016 |
| EP | 3308830 A1 | 4/2018 |
| FR | 2655548 | 6/1991 |
| NZ | 616894 | 1/2016 |
| NZ | 616944 | 6/2016 |
| WO | 1993014694 A1 | 8/1993 |
| WO | 1998053878 A1 | 12/1998 |
| WO | 2000019939 | 4/2000 |
| WO | 2000019940 | 4/2000 |
| WO | 2000061223 A1 | 10/2000 |
| WO | 2000061224 A1 | 10/2000 |
| WO | 0226317 A1 | 4/2002 |
| WO | 2003098177 A1 | 11/2003 |
| WO | 2004006785 A1 | 1/2004 |
| WO | 2004006795 A1 | 1/2004 |
| WO | 2004032791 A1 | 4/2004 |
| WO | 2005089863 A1 | 9/2005 |
| WO | 2006092007 | 9/2006 |
| WO | 2007067690 A2 | 6/2007 |
| WO | 2007146489 A1 | 12/2007 |
| WO | 2007146493 A1 | 12/2007 |
| WO | 2007146517 A1 | 12/2007 |
| WO | 2008030344 A1 | 3/2008 |
| WO | 2008100974 A2 | 8/2008 |
| WO | 2009018518 | 2/2009 |
| WO | 2009042217 A1 | 4/2009 |
| WO | 2009094609 | 7/2009 |
| WO | 2009114008 | 9/2009 |
| WO | 2010042461 | 4/2010 |
| WO | 2010042686 | 4/2010 |
| WO | 2011109739 | 9/2011 |
| WO | 2011159271 | 12/2011 |
| WO | 2012142539 | 10/2012 |
| WO | 2012151449 | 11/2012 |
| WO | 2012167213 | 12/2012 |
| WO | 2013033673 | 3/2013 |
| WO | 2013126930 | 8/2013 |
| WO | 2014032030 | 2/2014 |
| WO | 2014113724 | 7/2014 |
| WO | 2014153267 | 9/2014 |
| WO | 2015034867 | 3/2015 |
| WO | 2015077425 | 5/2015 |
| WO | 2015077435 | 5/2015 |
| WO | 2016154076 | 9/2016 |

(56) References Cited

FOREIGN PATENT DOCUMENTS

| WO | 2016154076 A2 | 9/2016 |
|---|---|---|
| WO | 2017155916 A1 | 9/2017 |
| WO | 2018039552 A1 | 3/2018 |

OTHER PUBLICATIONS

International Search Report for PCT/US2007/018631, dated Mar. 25, 2008.
Written Opinion for PCT/US2007/018631, dated Mar. 25, 2008.
International Search Report for PCT/US2007/006178, dated Dec. 5, 2008.
Written Opinion for PCT/US2007/006178, dated Dec. 5, 2008.
International Search Report for PCT/US2007/068617, dated Mar. 10, 2008.
Written Opinion for PCT/US2007/068617, dated Mar. 10, 2008.
International Search Report for PCT/US2007/066916, dated Dec. 20, 2017.
International Search Report for PCT/US2003/029744, dated Apr. 22, 2004.
International Search Report for PCT/US2003/015174, dated Apr. 27, 2004.
International Search Report for PCT/US2009/059609, dated Mar. 5, 2010.
International Search Report for PCT/US2012/040639, dated Dec. 18, 2012.
International Search Report for PCT/US2010/038444, dated Sep. 16, 2010.
International Search Report for PCT/US2009/59947, dated Feb. 12, 2010.
International Search Report for PCT/US2013/035031, dated Jun. 24, 2015.
International Search Report for PCT/US2014/012131, dated Jul. 30, 2014.
International Search Report for PCT/US2014/029846, dated Apr. 2, 2015.
International Search Report for PCT/US2009/031935, dated Jun. 15, 2009.
International Search Report for PCT/US2008/056479, dated Aug. 20, 2008.
International Search Report for PCT/2011/027243, dated Jul. 8, 2011.
International Search Report for PCT/US2012/033695, dated Aug. 7, 2012.
International Search Report for PCT/US2012/053576, dated Dec. 24, 2012.
International Search Report for PCT/US2013/056520, dated Apr. 4, 2014.
International Search Report for PCT/US2012/036408, dated Aug. 17, 2012.
International Search Report for PCT/US2014/066565, dated Mar. 12, 2015.
International Search Report for PCT/US2014/053793, dated Mar. 27, 2015.
International Search Report for PCT/US2014/066578, dated Mar. 19, 2015.
International Search Report for PCT/US2016/023327, dated Jan. 12, 2017.
International Search Report for PCT/US2017/048594, dated Dec. 26, 2017.
International Search Report for PCT/US2017/021044, dated Jul. 26, 2017.
Knott, E. M., et al., "Increased Lymphatic Flow in the Thoracic Duct During Manipulative Intervention", J Am Osteopath Assoc., 105(10), (Oct. 2005), 447-456.
Issa, Z. F., et al., "Thoracic Spinal Cord Stimulation Reduces the Risk of Ischemic Ventricular Arrhythmias in a Postinfarction Heart Failure Canine Model", Circulation, 111(24) (Jun. 21, 2005), 3217-3220.
Jameison, GG et al. "Laparoscopic Nissen Fundoplication". Annals of Surgery, vol. 220. No. 2, p. 139 (1994).
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
International Search Report for PCT/US2009/059947, dated Feb. 12, 2010.
Noelting et al. "Normal Values for High-Resolution Anorectal Manometry in Healthy Women: Effects of Age and Significance of Rectoanal Gradient". Am J Gastroenterol. Oct. 2012; 107(10):1530-1536.
Seong et al. "Comparative analysis of summary scoring systems in measuring fecal incontinence". J Korean Surg Soc. 2011; 81:326-331.
Rust et al. "The GRISS: A Psychometric Instrument for the Assessment of Sexual Dysfunction". Articles of Sexual Behavior, vol. 15, No. 2, 1986, 157-165.
Infrasca, R. "Sexual Dysfunction Questionnaire: scale development and psychometric validation". Giorn Ital Psicopat 2011; 17:253-260.
Althof et al. "Outcome Measurement in Female Sexual Dysfunction Clinical Trials: Review and Recommendations". Journal of Sex & Marital Therapy, 31: 153-166, 2005.
Janssen et al. "Promis Sexual Function and Satisfaction Measures User Manual", nihpromis.org; Jul. 8, 2015, 1-15.
Rosen et al. "The International Index of Erectile Function (IIEF)". Sample; 1997. 1-5.
Ghoniem et al. "Evaluation and outcome measures in the treatment of female urinary stress incontinence: International Urogynecological Association (IUGA) guidelines for research and clinical practice". Int Urogynecol J (2008) 19:5-33.
Gill et al. "Urodynamic Studies for Urinary Incontinence", http://emedicine.medscape.com/article/1988665overview#a4; Mar. 17, 2016, 1-14.
Brizzolara et al., "Evidence for noradrenergic-purinergic cotransmission in the hepatic artery of the rabbit"; Br. J. Pharmacol. (1990), 99, 835-839.
"Miniature electrical stimulator for hemorrhage control", Brinton et al., IEEE Trans Biomed Eng. Jun. 2014; 61(6): 1765-71. doi: 10.1109/TBME.2014.2306672 (Year: 2014).
Mandel Y, Manivanh R, Dalal R, et al. Vasoconstriction by electrical stimulation: new approach to control of non-compressible hemorrhage. Sci Rep. 2013;3:2111. doi: 10.1038/srep02111 (Year: 2013).

\* cited by examiner

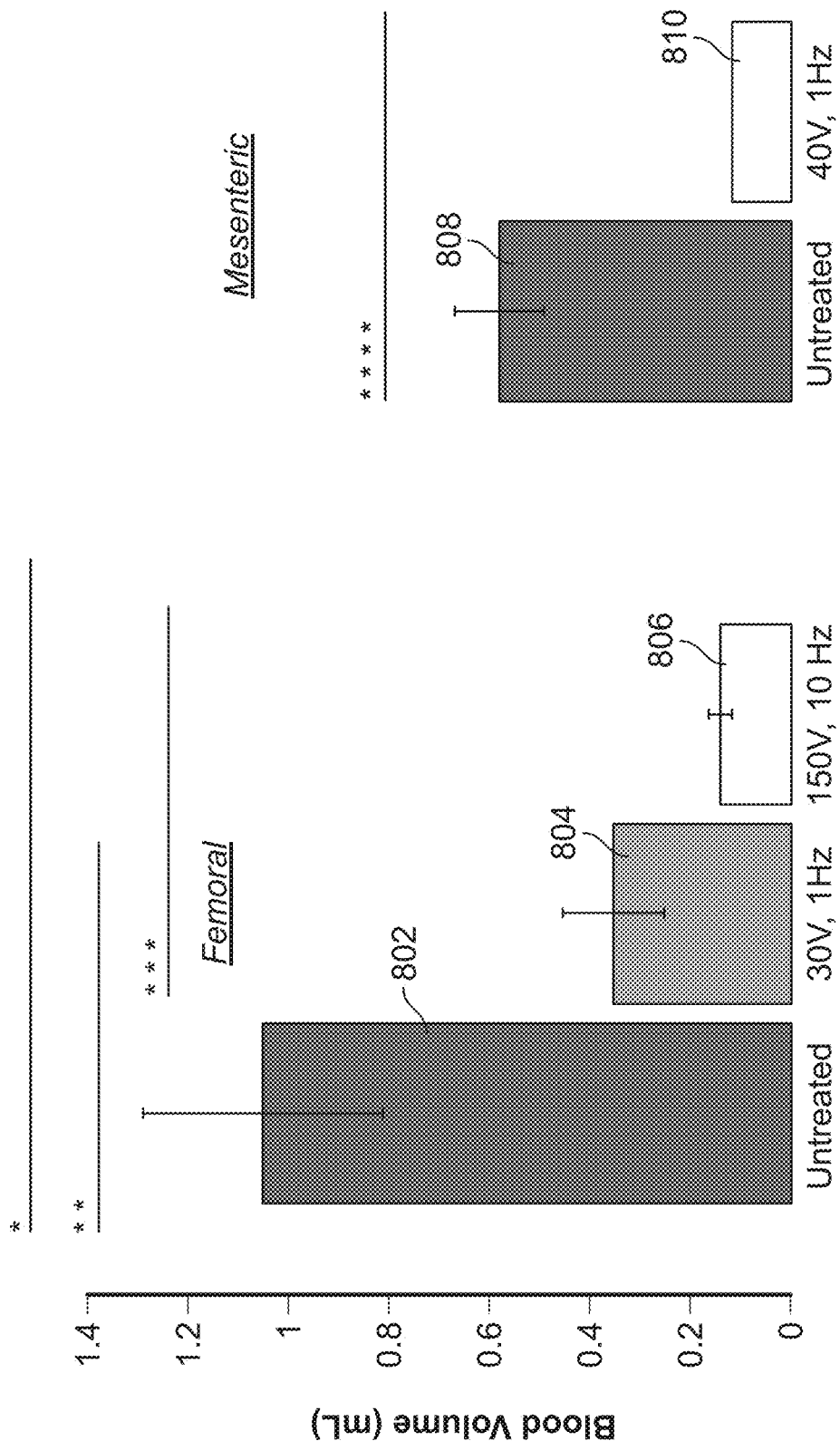

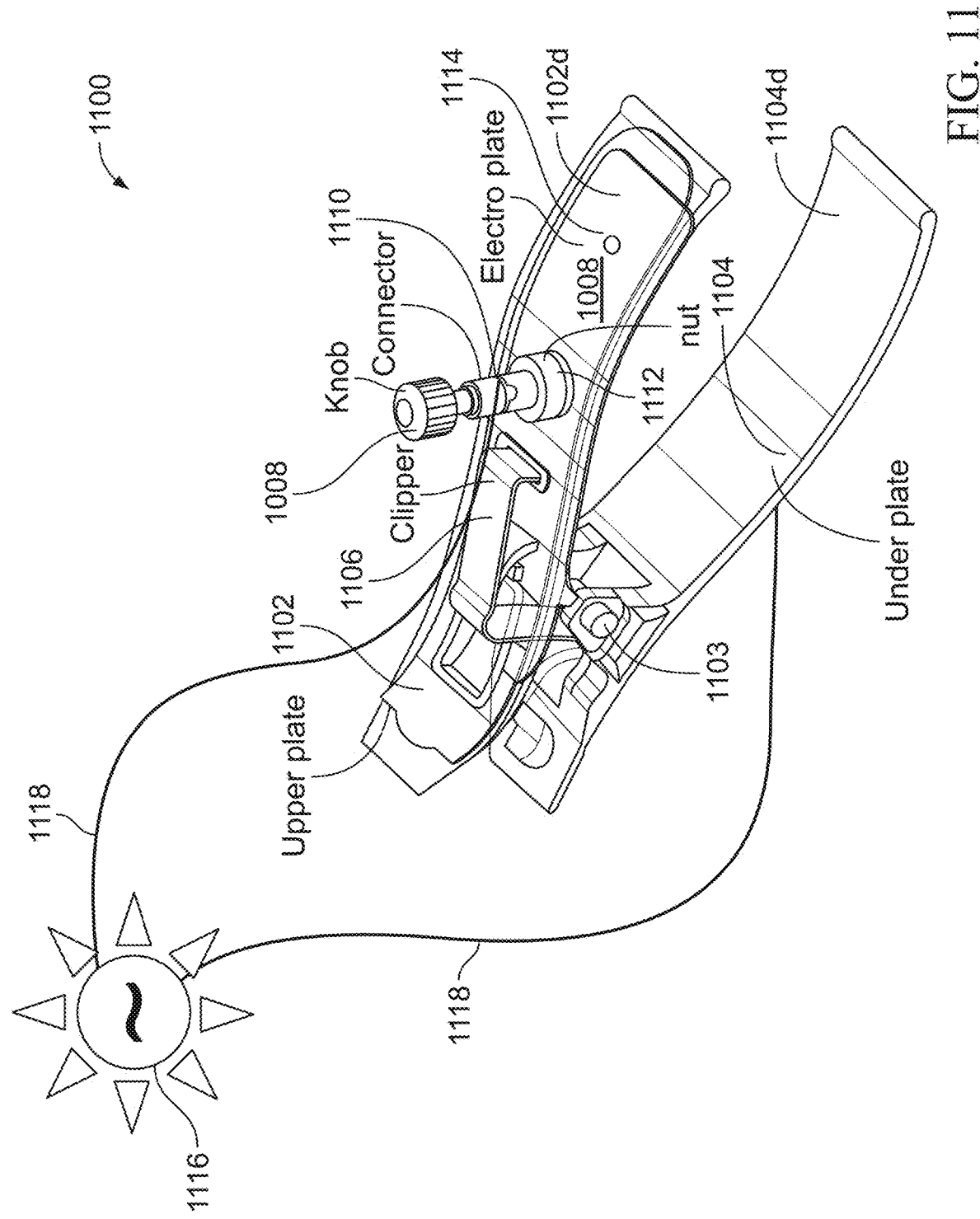

Electrodes

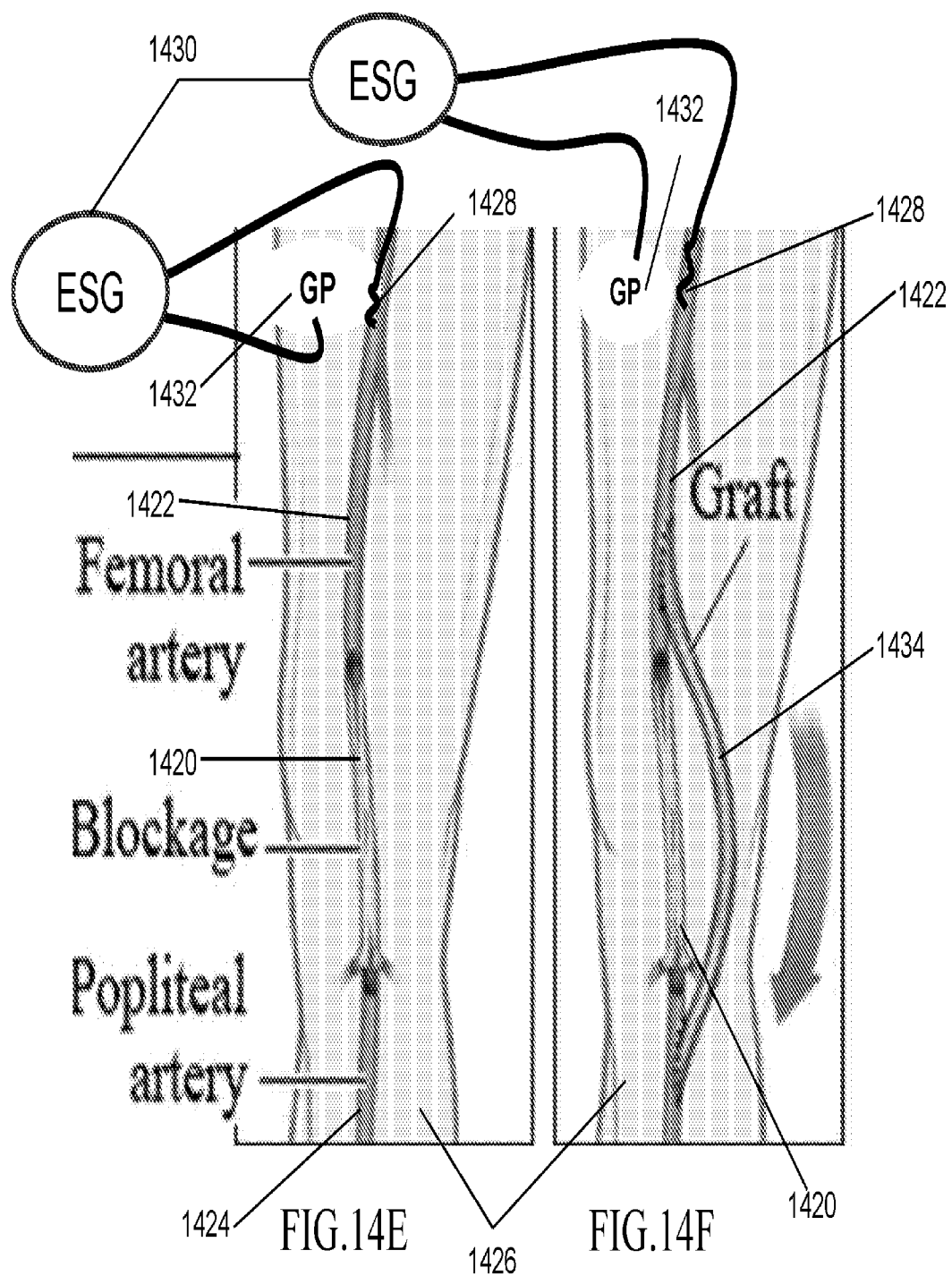

Anchor design with patch

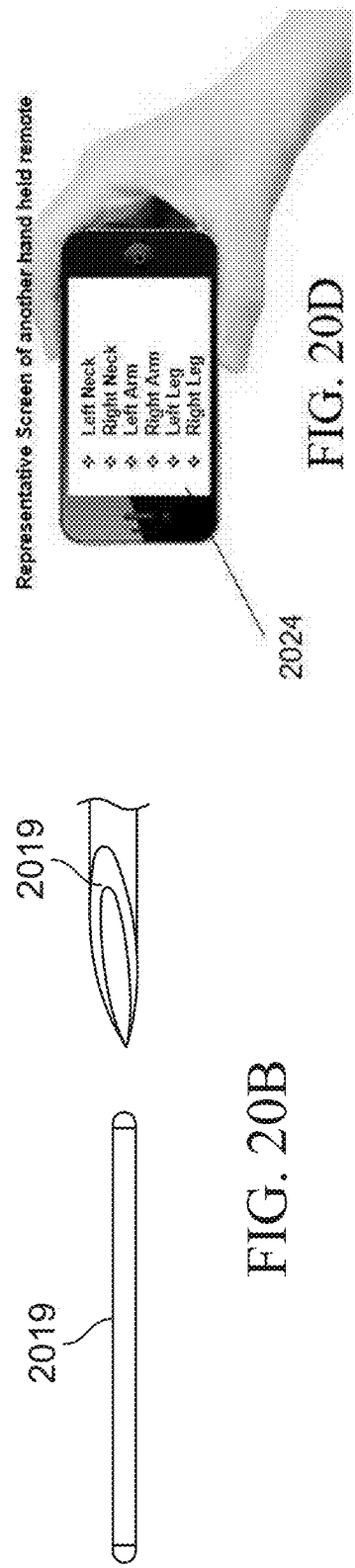

METHODS AND APPARATUSES FOR STIMULATING BLOOD VESSELS IN ORDER TO CONTROL, TREAT, AND/OR PREVENT A HEMORRHAGE

CROSS-REFERENCE

The present application is a division application of U.S. patent application Ser. No. 15/451,629, entitled "Methods and Apparatuses for Stimulating Blood Vessels in Order to Control, Treat, and/or Prevent a Hemorrhage" and filed on Mar. 7, 2017, which relies on U.S. Provisional Patent Application No. 62/328,303, entitled "Method and Apparatus for Stimulating Blood Vessels for Modulating Blood Flow" and filed on Apr. 27, 2016, and U.S. Provisional Patent Application No. 62/304,841, of the same title and filed on Mar. 7, 2016, for priority.

U.S. patent application Ser. No. 15/451,629 is also a continuation in part application of U.S. patent application Ser. No. 14/728,630, entitled "Method and Apparatus for Stimulating the Vascular System", filed on Jun. 2, 2015, and issued as U.S. Pat. No. 9,656,068 on May 23, 2017, which is a continuation application of U.S. patent application Ser. No. 12/575,713, of the same title, filed on Oct. 8, 2009, and issued as U.S. Pat. No. 9,079,028 on Jul. 14, 2015, which relies on U.S. Provisional Patent Application No. 61/104,054, of the same title and filed on Oct. 9, 2008, for priority.

All of the aforementioned applications are incorporated herein by reference in their entirety.

FIELD

The present specification is directed toward modulating blood flow using electrical stimulation and, more specifically, to preventing, controlling and/or treating a hemorrhage by stimulating arteries, veins or nerves supplying the arteries and veins of a patient.

BACKGROUND

Trauma is the leading cause of death among US individuals younger than 44 years.

Hemorrhagic shock accounts for 30-40 percent of traumatic mortality. Bleeding is also the most common preventable cause of death on the battlefield. Applications of tourniquets to compressible hemorrhages results in a marked decrease in limb exsanguinations. According to the US army, hemorrhage not amenable to truncal tourniquets (also called non-compressible hemorrhage) is now the leading cause of preventable death. Some of the non-compressible hemorrhages occur due to bleeding into body cavities (such as the abdomen or chest), while others are caused by wounds in the junction between the trunk and the limbs or neck.

Effective prevention of blood loss in the pre-hospital arena offers the best opportunity to save soldiers with non-compressible injuries, therefore major efforts are undertaken to develop technologies for this unmet need. It has been demonstrated that thrombosis can be induced in a clamped blood vessel by minutes-long application of direct electric current. However, associated thermal damage precluded the use of this technology in clinical practice.

In addition, hemorrhage is a leading cause of death in operating rooms across the world. Approximately 4 in every 10,000 surgical patients, and 6 in every 10,000 patients receiving anesthesia, suffer fatal cardiac arrest within 30 postoperative days. Hemorrhage is responsible for 33% of these cardiac arrests.

Hence, there is a need for a quick and efficient method of preventing or controlling hemorrhage conditions in an organ without causing tissue damage. Such hemorrhage control would be applicable all hemorrhage situations and particularly in combat and operating room scenarios.

SUMMARY

The present specification discloses a method of preventing an anticipated hemorrhage in an artery or vein of an upper limb of a patient using at least one electrode in electrical communication with a pulse generator, the method comprising: arranging the at least one electrode at a location proximate a surface of the patient's artery or vein, wherein said artery is at least one of a subclavian artery, an axillary artery, a deep brachial artery, a brachial artery, a radial artery, an ulnar artery, a deep palmar arch, and a superficial palmar arch or said vein is at least one of subclavian vein, axillary vein, cephalic vein, brachial vein, radial vein, ulnar vein, deep palmar arch, superficial palmar arch, basilic vein, median cubital vein, and median antebrachial vein and wherein said location is at least 1 cm upstream from a location of the anticipated hemorrhage; and causing the pulse generator to generate an electrical stimulus administered to the artery or the vein through the at least one electrode, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction in said artery or said vein and thereby prevent said anticipated hemorrhage.

Optionally, the pulse duration ranges from 1 μsec to 500 msec, the pulse amplitude ranges from 1 V to 250 V, and the pulse frequency ranges from 1 Hz to 100 kHz.

Optionally, the at least one electrode is at least one of a cuff electrode and a clamp electrode and arranging the at least one electrode comprises placing said cuff electrode or said clamp electrode in direct physical contact with said location.

Optionally, a radio-frequency (RF) receiver is coupled to said at least one electrode and a RF transmitter is coupled to said pulse generator and in wireless communication with said RF receiver and said method further comprises causing the pulse generator to generate, and wirelessly transmit, an electrical stimulus from the RF transmitter to the RF receiver to be administered by said at least one electrode.

The method may further comprise using a microprocessor operably connected to the pulse generator to selectively set said pulse duration, said pulse amplitude, and said pulse frequency.

The present specification also discloses a method of preventing an anticipated hemorrhage in an artery or vein of a lower limb of a patient using at least one electrode in electrical communication with a pulse generator, the method comprising: arranging the at least one electrode at a location proximate a surface of the patient's artery or vein, wherein said artery is at least one of a femoral artery, popliteal artery, anterior tibial artery, posterior tibial artery, peroneal artery, dorsalis pedis artery, and plantar arch or said vein is at least one of external iliac vein, femoral vein, perforating vein, great saphenous vein, small saphenous vein, anterior tibial vein, posterior tibial vein, and dorsal venous arch and wherein said location is at least 1 cm upstream from a location of an anticipated hemorrhage; and causing the pulse generator to generate an electrical stimulus administered to the artery or the vein through the at least one electrode, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction in said artery or said vein and thereby prevent said anticipated hemorrhage.

Optionally, the pulse duration ranges from 1 µsec to 500 msec, the pulse amplitude ranges from 1 V to 250 V, and the pulse frequency ranges from 1 Hz to 100 kHz.

Optionally, the at least one electrode is a cuff electrode or clamp electrode and arranging the at least one electrode comprises placing said cuff electrode or said clamp electrode in direct physical contact with said location.

Optionally, a radio-frequency (RF) receiver is coupled to said at least one electrode and a RF transmitter is coupled to said pulse generator and in wireless communication with said RF receiver, and said method further comprises causing the pulse generator to generate, and wirelessly send, an electrical stimulus from the RF transmitter to the RF receiver to be administered by said at least one electrode.

The method may further comprise using a microprocessor operably connected to the pulse generator to selectively set said pulse duration, said pulse amplitude, and said pulse frequency.

The present specification also discloses a method of controlling a hemorrhage in a patient in advance of a planned surgical procedure, the method comprising: initiating a surgery in an abdominal region of said patient; arranging at least one electrode of a stimulation apparatus at a location in electrical communication with a blood vessel upstream to, and supplying blood to, a blood vessel in said abdominal region before said hemorrhage develops; connecting said at least one electrode to an electrical pulse generator; identifying the hemorrhage during said surgical procedure; and causing the pulse generator to generate an electrical stimulus administered to the upstream blood vessel, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction of the upstream blood vessel and reduce blood flow to control the hemorrhage of the blood vessel in the abdominal region.

Optionally, the pulse duration ranges from 1 µsec to 500 msec, the pulse amplitude ranges from 1 V to 250 V, and the pulse frequency ranges from 1 Hz to 100 kHz.

Optionally, the at least one electrode is a cuff electrode or clamp electrode and arranging the at least one electrode comprises placing said cuff electrode or said clamp electrode in direct physical contact with said location.

Optionally, a radio-frequency (RF) receiver is coupled to said at least one electrode and a RF transmitter is coupled to said pulse generator and in wireless communication with said RF receiver, and said method further comprises causing the pulse generator to generate, and wirelessly send, an electrical stimulus from the RF transmitter to the RF receiver to be administered by said at least one electrode.

The method may further comprise using a microprocessor operably connected to the pulse generator to selectively set said pulse duration, said pulse amplitude, and said pulse frequency.

The present specification also discloses a method of preventing a hemorrhage in a patient in advance of a planned surgical procedure, the method comprising: initiating a surgery in an abdominal region of said patient, wherein initiating surgery is defined as exposing an area proximate a blood vessel in said abdominal region that is involved in said surgery; arranging at least one electrode of a stimulation apparatus at a location in electrical communication with a blood vessel upstream to, and supplying blood to, the blood vessel in said abdominal region before said hemorrhage develops; connecting said at least one electrode to an electrical pulse generator; proceeding with said surgery; prior to beginning a surgical technique in which an increased likelihood of the hemorrhage is anticipated, causing the pulse generator to generate an electrical stimulus administered to the upstream blood vessel for a predetermined period of time, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction of the upstream blood vessel and reduce blood flow to prevent the hemorrhage of the blood vessel in the abdominal region; and proceeding with said surgical technique.

Optionally, said predetermined period of time is equal to at least 30 seconds.

Optionally, said electrical stimulus is administered for at least 10 seconds during said surgical technique.

Optionally, said electrical stimulus is administered prior to beginning said surgical technique and during a remainder of the surgery.

Optionally, said at least one electrode is configured to remain within said abdominal region for a period of time ranging from 1 to 7 days and said electrical stimulus is administered post-operatively to treat a post-operative hemorrhage.

The present specification discloses a method of treating a hemorrhage in an artery or vein of an upper limb of a patient using at least one electrode in electrical communication with a pulse generator, the method comprising: arranging the at least one electrode at a location proximate a surface of the patient's artery or vein, wherein said artery is at least one of a subclavian artery, an axillary artery, a deep brachial artery, a brachial artery, a radial artery, an ulnar artery, a deep palmar arch, and a superficial palmar arch or said vein is at least one of subclavian vein, axillary vein, cephalic vein, brachial vein, radial vein, ulnar vein, deep palmar arch, superficial palmar arch, basilic vein, median cubital vein, and median antebrachial vein and wherein said location is at least 1 cm upstream from a location of the hemorrhage; and causing the pulse generator to generate an electrical stimulus administered to the artery or the vein through the at least one electrode, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction in said artery or said vein.

The pulse duration may range from 1 µsec to 500 msec, the pulse amplitude may range from 1 V to 250 V, and the pulse frequency may range from 1 Hz to 100 kHz.

Optionally, the at least one electrode is a cuff electrode or clamp electrode and arranging the at least one electrode comprises placing said cuff electrode or said clamp electrode in physical contact with said location.

Optionally, a radio-frequency (RF) receiver is coupled to said at least one electrode and a RF transmitter is coupled to said pulse generator and in wireless communication with said RF receiver and the method further comprises causing the pulse generator to generate, and wirelessly send, an electrical stimulus from the RF transmitter to the RF receiver to be administered by said at least one electrode.

Optionally, the method further comprises using a microprocessor operably connected to the pulse generator to selectively set said pulse duration, said pulse amplitude, and said pulse frequency.

The present specification also discloses a method of treating a hemorrhage in an artery or vein of a lower limb of a patient using at least one electrode in electrical communication with a pulse generator, the method comprising: arranging the at least one electrode at a location proximate a surface of the patient's artery or vein, wherein said artery is at least one of a femoral artery, popliteal artery, anterior tibial artery, posterior tibial artery, peroneal artery, dorsalis pedis artery, and plantar arch or said vein is at least one of external iliac vein, femoral vein, perforating vein, great saphenous vein, small saphenous vein, anterior tibial vein, posterior tibial vein, and dorsal venous arch and wherein said location is at least 1 cm upstream from a location of the hemorrhage; and causing the pulse generator to generate an electrical stimulus administered to the artery or the vein through the at least one electrode, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction in said artery or said vein.

The pulse duration may range from 1 μsec to 500 msec, the pulse amplitude may range from 1 V to 250 V, and the pulse frequency may range from 1 Hz to 100 kHz.

Optionally, the at least one electrode is a cuff electrode or clamp electrode and arranging the at least one electrode comprises placing said cuff electrode or said clamp electrode in physical contact with said location.

Optionally, a radio-frequency (RF) receiver is coupled to said at least one electrode and a RF transmitter is coupled to said pulse generator and in wireless communication with said RF receiver and the method further comprises causing the pulse generator to generate, and wirelessly send, an electrical stimulus from the RF transmitter to the RF receiver to be administered by said at least one electrode.

Optionally, the method further comprises using a microprocessor operably connected to the pulse generator to selectively set said pulse duration, said pulse amplitude, and said pulse frequency.

The present specification also discloses a method of preventing or treating a hemorrhage in a patient in advance of a planned surgical procedure, the method comprising: initiating a surgery in an abdominal region of said patient; arranging at least one electrode of a stimulation apparatus at a location in electrical communication with a blood vessel upstream to and supplying blood to a blood vessel in said abdominal region before a hemorrhage develops; connecting said at least one electrode to an electrical pulse generator; identifying a hemorrhage during said surgical procedure; and causing the pulse generator to generate an electrical stimulus administered to the upstream blood vessel, wherein the electrical stimulus has a pulse duration, a pulse amplitude, and a pulse frequency and wherein said pulse duration, said pulse amplitude, and said pulse frequency are selected such that the electrical stimulus is effective for causing vasoconstriction of the upstream blood vessel and reducing blood flow to prevent or control hemorrhage of the blood vessel involved in the abdominal region. The said pulse stimulus can be applied for at least 30 seconds before the onset of such hemorrhage, thus reducing the frequency or severity of such hemorrhage.

The pulse duration may range from 1 μsec to 500 msec, the pulse amplitude may range from 1 V to 250 V, and the pulse frequency may range from 1 Hz to 100 kHz.

Optionally, at least one electrode is a cuff electrode or clamp electrode and arranging the at least one electrode comprises placing said cuff electrode or said clamp electrode in physical contact with said location.

Optionally, a radio-frequency (RF) receiver is coupled to said at least one electrode and a RF transmitter is coupled to said pulse generator and in wireless communication with said RF receiver and said method further comprises causing the pulse generator to generate, and wirelessly send, an electrical stimulus from the RF transmitter to the RF receiver to be administered by said at least one electrode.

Optionally, the method further comprises using a microprocessor operably connected to the pulse generator to selectively set said pulse duration, said pulse amplitude, and said pulse frequency.

The present specification also discloses a method of treating a hemorrhage in a body organ of a patient, the method comprising: arranging at least one electrode of a stimulation apparatus proximate an artery supplying blood to the body organ, a vein supplying blood from the body organ, a nerve supplying said artery or said vein, or a wall of said body organ; connecting said at least one electrode to an electrical pulse generator; and causing the pulse generator to generate an electrical stimulus administered to the artery, vein, nerve, or wall of said body organ through the at least one electrode, wherein the electrical stimulus is effective for causing vasoconstriction and reducing blood flow to said body organ. Optionally, the electrode of the stimulation apparatus is in electrical communication with an artery supplying blood to the body organ, a vein supplying blood from the body organ, a nerve supplying said artery or said vein, or a wall of said body organ.

The electrical stimulus may have a pulse duration ranging from 1 μsec to 500 msec, a pulse amplitude ranging from 1 V to 250 V, and a pulse frequency ranging from 1 Hz to 100 kHz.

Optionally, the electrode is a cuff electrode or clamp electrode and arranging the at least one electrode proximate an artery, a vein, a nerve supplying an artery or vein, or a wall of said body organ comprises placing said cuff electrode or said clamp electrode in physical contact with said artery, vein, nerve, or wall.

Optionally, a radio-frequency (RF) receiver is coupled to said at least one electrode and a RF transmitter is coupled to said pulse generator and in wireless communication with said RF receiver, and said method further comprises the step of causing the pulse generator to generate and wirelessly send an electrical stimulus from the RF transmitter to the RF receiver to be administered by said at least one electrode.

Optionally, the apparatus further comprises a microprocessor operably connected to the pulse generator, wherein at least one parameter of the stimulus is controlled by the microprocessor and wherein said method further comprises using the microprocessor to control said pulse generator to generate an electrical stimulus.

The present specification also discloses a method of modulating blood flow to an organ of a patient, the method comprising: providing an apparatus comprising at least one electrode operably connected to a pulse generator; placing the at least one electrode in electrical communication with an artery supplying blood to the organ, a vein supplying blood from the organ, or a nerve supplying said artery or said vein; and causing the pulse generator to generate an electrical stimulus administered to the artery, vein, or nerve through the at least one electrode, wherein the electrical stimulus is effective for modulating blood flow to the organ.

The stimulus may be effective for constricting the artery or vein.

The electrical stimulus may have a pulse duration ranging from 1 μsec to 500 msec, a pulse amplitude ranging from 1 V to 250 V, and a pulse frequency ranging from 1 Hz to 100 kHz.

Optionally, the electrode is a cuff electrode or clamp electrode and arranging the at least one electrode proximate an artery, a vein, or nerve supplying an artery or vein comprises placing said cuff electrode or said clamp electrode in physical contact with said artery, vein, or nerve.

Optionally, a radio-frequency (RF) receiver is coupled to said at least one electrode and a RF transmitter is coupled to said pulse generator and in wireless communication with said RF receiver, and said method further comprises the step of causing the pulse generator to generate and wirelessly send an electrical stimulus from the RF transmitter to the RF receiver to be administered by said at least one electrode.

Optionally, the apparatus further comprises a microprocessor operably connected to the pulse generator, wherein at least one parameter of the stimulus is controlled by the microprocessor and wherein said method further comprises using the microprocessor to control said pulse generator to generate an electrical stimulus.

The present specification also discloses a method of modulating blood flow to an organ of a patient, the method comprising: providing an apparatus comprising at least one electrode operably connected to a pulse generator; placing the at least one electrode in electrical communication with a wall of the organ; and causing the stimulus generator to generate an electrical stimulus administered proximate the wall through the at least one electrode, wherein the electrical stimulus is effective for modulating blood flow to the organ.

The stimulus may be effective for constricting or dilating one or more blood vessels within the wall of the organ, thus altering the blood flow through the said blood vessel.

Optionally, a radio-frequency (RF) receiver is coupled to said at least one electrode and a RF transmitter is coupled to said pulse generator and in wireless communication with said RF receiver, and said method further comprises the step of causing the pulse generator to generate and wirelessly send an electrical stimulus from the RF transmitter to the RF receiver to be administered by said at least one electrode.

Optionally, the apparatus further comprises a microprocessor operably connected to the pulse generator, wherein at least one parameter of the stimulus is controlled by the microprocessor and wherein said method further comprises using the microprocessor to control said pulse generator to generate an electrical stimulus.

The present specification also discloses a method of controlling blood flow to an organ comprising the steps of: arranging at least one electrode proximate to an artery, a vein or a nerve supplying an artery and vein and activating said electrode to provide an electrical stimulus thereto, wherein said electrical stimulus is effective in controlling the blood flow to the organ.

The present specification also disclose a method of controlling blood flow to an organ comprising the steps of: arranging at least one electrode proximate to an artery supplying blood to the organ, a vein supplying blood from the organ, or a nerve supplying said artery or said vein and activating said electrode to provide a first electrical stimulus thereto, wherein said the first electrical stimulus is effective in decreasing the blood flow to the organ to prevent a hemorrhage and activating said electrode to provide a second electrical stimulus thereto, wherein said the second electrical stimulus is effective in decreasing the blood flow to the organ to treat a hemorrhage.

The present specification also discloses a method of preventing intraoperative bleeding comprising the steps of: arranging at least one electrode proximate or in electrical contact with an artery, a vein or a nerve supplying an artery and vein and activating said electrode to provide an electrical stimulus thereto, wherein said electrical stimulus is effective in controlling the blood flow in the artery or the vein.

The present specification also discloses a method of treating intraoperative bleeding comprising the steps of: arranging at least one electrode proximate to an artery, a vein or a nerve supplying an artery and vein and activating said electrode to provide an electrical stimulus thereto, wherein said electrical stimulus is effective in controlling the blood flow in the artery or the vein.

The present specification also discloses a method for generating an electrical signal for vascular stimulation, the method comprising: identifying a first electrical stimulation reaction threshold for vasoconstriction in a patient; identifying a second reaction threshold for thrombosis in the patient; and electrically stimulating a vascular structure with an electrical stimulation signal that is below said identified second reaction threshold for thrombosis and above said first reaction threshold for vasoconstriction such that the stimulus generates a predominance of vasoconstriction over thrombosis.

The present specification also discloses a method of controlling blood flow to an organ by arranging at least one electrode of a stimulation apparatus in electrical communication with an artery, a vein, a nerve supplying an artery or vein, or a wall of said body organ; connecting said at least one electrode to an electrical pulse generator; and causing the pulse generator to generate an electrical stimulus administered to the artery, vein, nerve, or wall of said body organ through the at least one electrode, wherein the electrical stimulus is effective for changing blood flow to said body organ where the change in the blood flow is maintained for at least 1 minute after the cessation of the electrical stimulation.

The above summary of the present invention is not intended to describe each disclosed embodiment or every implementation of the present invention. The description that follows more particularly exemplifies illustrative embodiments. However, embodiments other than those expressly described are possible and may be made, used, and/or practiced under circumstances and/or conditions that are the same or different from the circumstances and/or conditions described in connection with the illustrative embodiments. In several places throughout the application, guidance is provided through lists of examples, which examples can be used in various combinations. In each instance, the recited list serves only as a representative group and should not be interpreted as an exclusive list.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 8A illustrates a graph displaying blood loss from a femoral artery with and without application of electrical stimulation;

FIG. 8B illustrates a graph displaying blood loss from a mesenteric artery with and without application of electrical stimulation;

FIG. 11 illustrates an exemplary clamp electrode used for providing electrical simulation to blood vessels in various embodiments of the present specification;

FIG. 14E illustrates electrical stimulation being applied to a femoral artery having a blockage within a human leg, in accordance with an embodiment of the present specification;

FIG. 14F illustrates an arterial graft being applied after vasoconstriction of an artery in a human leg, in accordance with an embodiment of the present specification;

FIG. 20B illustrates an exemplary implantable microdevice used for delivering electrical stimulation to blood vessels, in accordance with an embodiment of the present specification;

FIG. 20C illustrates an exemplary hand held remote control device for activating an implanted microdevice for delivering electrical stimulation to blood vessels, in accordance with an embodiment of the present specification;

FIG. 20D illustrates another exemplary hand held remote control device for activating an implanted microdevice for delivering electrical stimulation to blood vessels, in accordance with another embodiment of the present specification;

DETAILED DESCRIPTION

Figure 1:
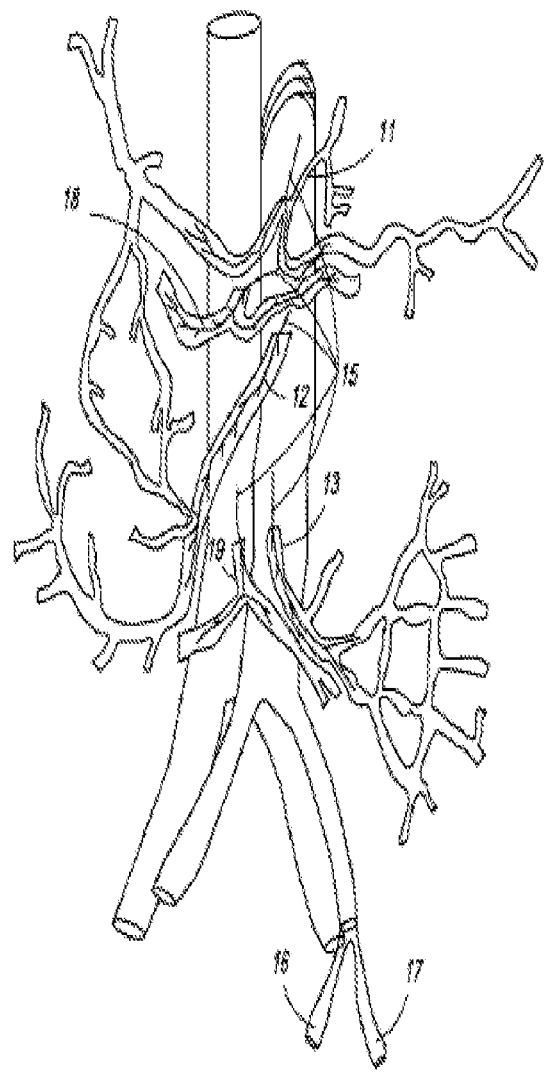
FIG. 1 is a schematic illustration of a portion of the mesenteric vascular system.

The present invention provides methods of treating a gastrointestinal (GI) disorder. Very generally, the treatment involves controlling the function of the gastrointestinal system by regulating the blood flow through the tissues and organs of the gastrointestinal tract. Generally, the control of blood flow through the GI tract is accomplished by administering a stimulus to either the vessels that supply blood to the GI tract or nerves that control those blood vessels.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Appetite Modulation

Mesenteric blood supply is important for proper functioning of the gastrointestinal system and is important for the digestion of all nutrients. Interrupting the mesenteric vascular supply may impair digestion of various nutrients, including fat digestion, and therefore can be helpful in managing conditions of over-nutrition including, for example, obesity.

Referring now to the various views of the accompanying drawings, FIG. 1 illustrates a portion of the gastro-intestinal (GI) tract including a celiac artery 11, a superior mesenteric artery 12, an inferior mesenteric artery 13, an internal iliac artery 16, an external iliac artery 17, a superior mesenteric vein 18, and an inferior mesenteric vein 19. As used herein, the term "mesenteric arteries" refers collectively to the celiac artery 11, superior mesenteric artery 12 and an inferior mesenteric artery 13. Also, the term "mesenteric veins" refers collectively to the superior mesenteric vein 18 and inferior mesenteric vein 19.

The mesenteric arteries constitute the major arterial blood supply of the gastrointestinal system and the mesenteric veins constitute the major system draining the blood from the gastrointestinal system. The flow of the blood to and from the gastrointestinal system is controlled by the tonic contraction and relaxation of the smooth muscle in the blood vessels of the mesenteric vascular system. The blood flow in the fasting state maintains the viability of the gastrointestinal tract. In the fed state, the work of the gastrointestinal tract increases and requires a corresponding increased need for oxygen and nutrients to the gastrointestinal system. The increased need for oxygen and nutrients is met by increasing the supply of blood to the gastrointestinal tract, accomplished by dilating the mesenteric arteries. This phenomenon of increasing the energy requirement of the gastrointestinal tract after a eating is known as the specific dynamic action of food. In situations of dehydration or hemorrhage, blood is shunted away from the gastrointestinal tract to other vital organs. This decrease in blood supply to the gastrointestinal tract is accomplished by the constriction of the mesenteric arteries. Subjects having a blockage in the mesenteric arteries due to, for example, atherosclerotic artery disease can have difficulty increasing the blood supply to the gastrointestinal tract that is required to process and digest food after a meal. These subjects can develop pain, loss of appetite, and weight loss.

The methods described herein involve controlling a subject's appetite, inducing satiety, and/or inducing weight loss by regulating the blood flow to the intestinal tract and more specifically by regulating the specific dynamic action of food—i.e., the meal-induced increase in the blood supply to the gastrointestinal tract—through stimulation of the mesenteric vasculature and/or nerves supplying the mesenteric vasculature.

The methods described herein can also be applied to treating certain cardiovascular conditions or indications, including angina, chest tightening, unstable angina, stable angina, coronary artery disease, atherosclerotic disease, heart failure or myocardial infarction. By reducing the blood flow to the intestinal tract and more specifically by minimizing the increase of blood flow to the gastrointestinal tract due to the specific dynamic action of food, the present invention can also help treat the aforementioned cardiovascular conditions. Specifically, reducing blood flow in the patient's mesenteric circulation or peripheral circulation increases blood flow in the coronary circulation or cerebral circulation, thereby reducing or eliminating symptoms related to the aforementioned disorders.

In order to reduce the meal-induced blood flow to the gastrointestinal tract, an electrical, chemical, or mechanical stimulus effective for treating a gastrointestinal condition is applied to one or more target locations in the celiac artery 11, superior mesenteric artery 12, inferior mesenteric artery 13, internal iliac artery 16, external iliac artery 17, superior mesenteric vein 18, or inferior mesenteric vein 19, or the nerves 15 supplying the celiac artery 11, superior mesenteric artery 12, inferior mesenteric artery 13, internal iliac artery 16, external iliac artery 17, superior mesenteric vein 18, or inferior mesenteric vein 19. As used herein, a stimulus "effective for treating a gastrointestinal condition" includes stimulation sufficient to result in, for example, contraction of at least one or more of the celiac artery 11, superior mesenteric artery 12, inferior mesenteric artery 13, internal iliac artery 16, external iliac artery 17, superior mesenteric vein 18, or inferior mesenteric vein 19, thus reducing the flow of blood into the gastrointestinal tract.

A reduction in the blood flow to the gastrointestinal tract can interrupt gastrointestinal function such as, for example, digestion and absorption of nutrients such as, for example, fat. The stimulation may result in curbing a subject's appetite and/or inducing satiety, anorexia, and/or weight loss in a subject due to discomfort incurred by a patient upon ingestion and, accordingly, stimulation of the target locations. Thus, in certain embodiments, a stimulus "effective for treating a gastrointestinal condition" can include stimulation that may, for example, curb a subject's appetite and/or induce satiety, anorexia, and/or weight loss in a subject. In other embodiments, a stimulus "effective for treating a gastrointestinal condition" can include a stimulus effective for treating a condition secondary to obesity such as, for example, diabetes, hypertension, heart attack, stroke, dyslipidemia, sleep apnea, Pickwick Ian Syndrome, asthma, lower back and disc disease, weight-bearing osteo-arthritis of the hips, knees, ankles and feet, thrombophlebitis and pulmonary emboli, intertriginous dermatitis, urinary stress incontinence, gastroesophageal reflux disease (GERD), gallstones, sclerosis, carcinoma of the liver, infertility, cancer of the uterus, and/or cancer of the breast.

In one embodiment, at least one electrode set is placed in the mesenteric circulation near one or more of the celiac artery 11, superior mesenteric artery 12, inferior mesenteric artery 13, internal iliac artery 16, external iliac artery 17, superior mesenteric vein 18 or inferior mesenteric vein 19 or a branch of the celiac artery 11, superior mesenteric artery 12, inferior mesenteric artery 13, internal iliac artery 16, external iliac artery 17, superior mesenteric vein 18 or inferior mesenteric vein 19. Each electrode set includes at least one active electrode and at least one ground electrode. The electrode set may be arranged in any pattern that produces the desired stimulation to the celiac artery 11, superior mesenteric artery 12, inferior mesenteric artery 13, internal iliac artery 16, external iliac artery 17, superior mesenteric vein 18 or inferior mesenteric vein 19, or a branch of the celiac artery 11, superior mesenteric artery 12, inferior mesenteric artery 13, internal iliac artery 16, external iliac artery 17, superior mesenteric vein 18 or inferior mesenteric vein 19 such as a circumferential pattern, along a longitudinal axis, an irregular pattern, or other placement.

In a preferred embodiment, the celiac artery or a branch of a celiac artery is stimulated by itself or in combination with at least one other vascular structure. In another preferred embodiment, the celiac artery or a branch of a celiac artery is stimulated in combination with the SMA or a branch of SMA. In yet another preferred embodiment, at least two vascular structures, such as arteries, veins, or nerves associated with the arteries or veins, are stimulated concurrently or in a predefined sequence, or a combination of both. The predefined sequence can be in rapid or slow succession.

Figure 2:
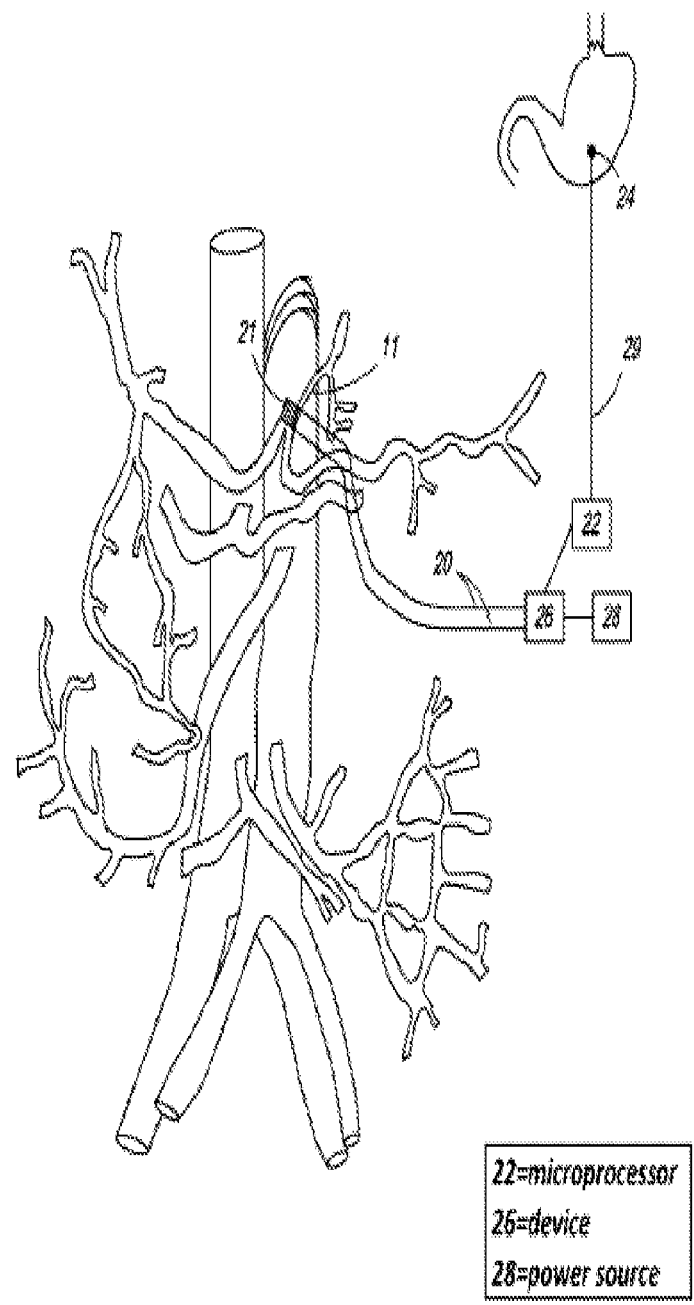
FIG. 2 is a schematic illustration of an exemplary electrode set implanted in the celiac artery.

FIG. 2 illustrates one embodiment where electrode set 21 is placed in a loose linear configuration in the celiac artery 11. A device comprising a pulse generator 26 transmits a signal that causes the electrode set 21 to deliver an electrical stimulation to the celiac artery 11. The device 26 is connected to a power source 28 for supplying a source of power. The device 26 is further connected to the electrode set 21 by wires 20 for transmitting an electrical stimulus signal to the electrode set 21. Alternatively, the electrode set 21 may be coupled to the device 26 in a wireless fashion using a radio frequency (RF) link, an ultrasonic link, a thermal link, a magnetic link, an electromagnetic link, or an optical link. Stimulation of the celiac artery 11 through the electrode set 21 can induce vasoconstriction of the celiac artery 11, which in turn can reduce blood supply to the upper gastrointestinal tract. The devices and control systems disclosed in U.S. patent application Ser. No. 12/359,317, filed on Jan. 25, 2009, which is incorporated herein by reference in its entirety, can be used for all embodiments of the inventions disclosed in this application.

In some embodiments, the stimulator device 26 could be triggered manually by, for example, a medical professional, a caregiver, or the subject. Alternatively, a set of sensing electrodes 24 can detect one of the physiological parameters associated with eating a meal and generate a signal to deliver an electrical stimulus to the celiac artery 11, which can result in meal-induced celiac vasoconstriction, thereby curbing a subject's appetite and/or inducing anorexia, satiety, and/or weight loss in the subject. Exemplary physiological parameters are identified below.

Figure 3:
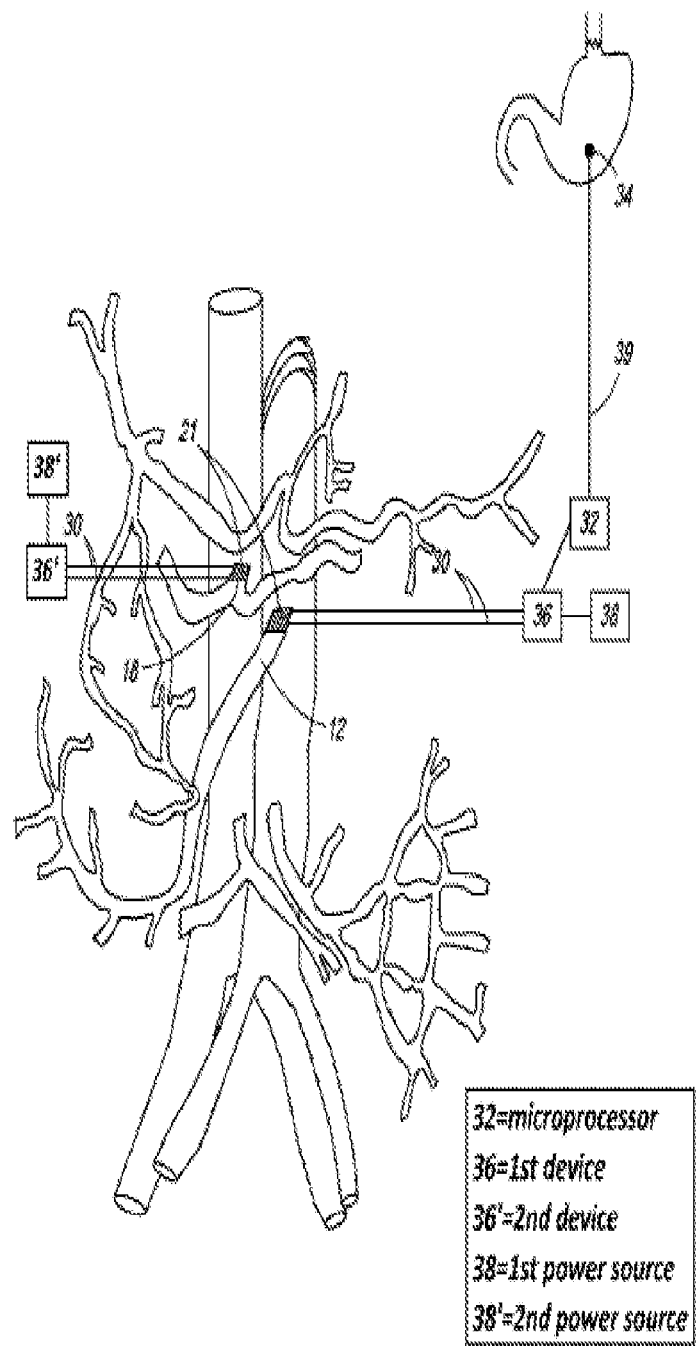
FIG. 3 is a schematic illustration of an exemplary electrode set implanted in the superior mesenteric vessels.

FIG. 3 shows another embodiment in which the electrode set 21 is placed on one of the superior mesenteric artery 12 or superior mesenteric vein 18. First and second devices comprising a pulse generator 36, 36' are connected to first and second power sources 38, 38' for supplying a source of power. The devices 36, 36' are further connected to the electrode sets 21 by wires 30, as previously described. Alternatively, the electrode sets 21 may be coupled to the device 36, 36' in a wireless fashion, as previously described. The stimulating electrode 21 can stimulate the superior mesenteric artery 12 to cause superior mesenteric artery 12 vasoconstriction or stimulate the superior mesenteric vein 18 to cause superior mesenteric vein 18 vasoconstriction, thereby decreasing blood supply to middle part of the gastrointestinal system.

In some embodiments, the stimulator devices 36, 36' can be triggered manually by, for example, a medical professional, a caregiver, or the subject. Alternatively, a set of sensing electrodes 34 can detect one of the physiological parameters associated with a meal and generate a signal to cause superior mesenteric artery 12 or superior mesenteric vein 18 vasoconstriction, and decrease blood supply to middle part of the gastrointestinal system. This can induce feelings of fullness, satiety and/or reduced appetite.

Figure 4:
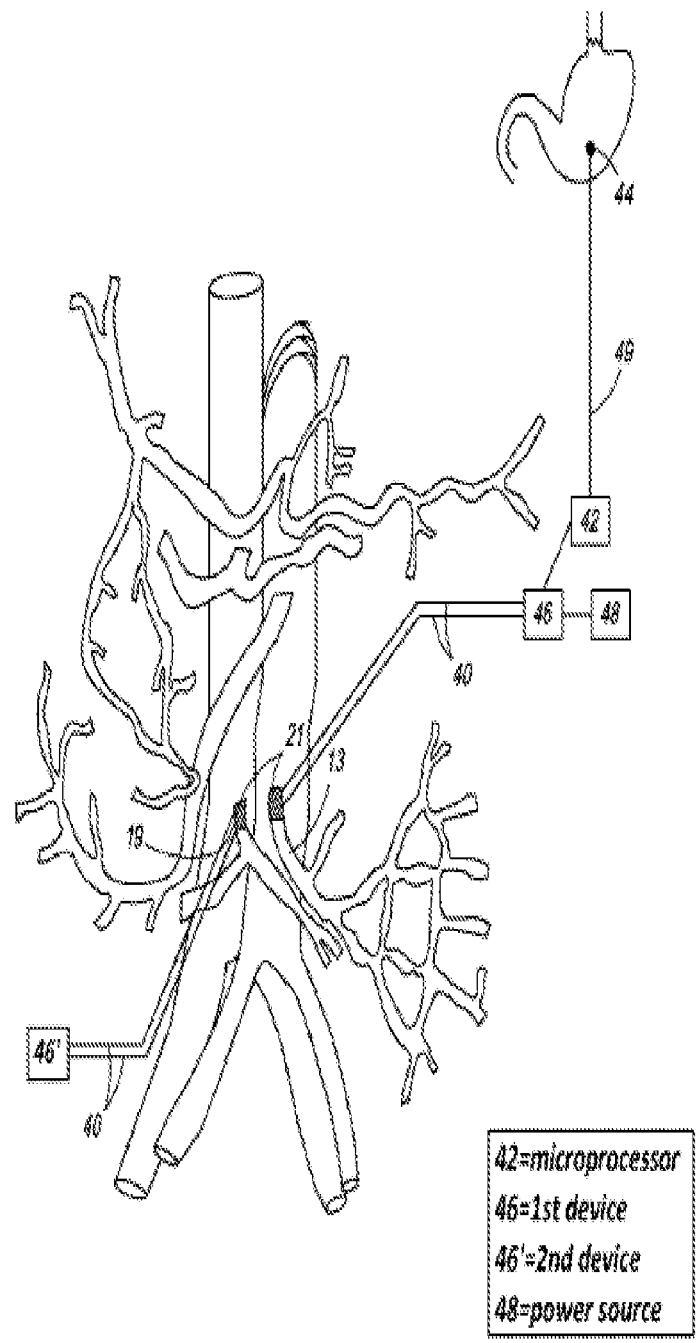
FIG. 4 is a schematic illustration of an exemplary electrode set implanted in the inferior mesenteric vessels.

FIG. 4 shows another embodiment in which the electrode set 21 is placed in one of the inferior mesenteric artery 13 or inferior mesenteric vein 19. A first device comprising a pulse generator 46 is connected to a power source 48 for supplying a source of power. The devices 46, 46' may be further connected to the electrode set 21 by wires 40, as previously described. Alternatively, the electrode set 21 may be coupled to the devices 46, 46' in a wireless fashion. One of the devices 46, 46' may control one electrode set 21. Alternatively, one of the devices 46, 46' may control more than one electrode set. The stimulating electrode 21 can stimulate the inferior mesenteric artery 13 or inferior mesenteric vein 19 causing vasoconstriction, and decrease blood supply to lower gastrointestinal system.

In some embodiments, the stimulator device 46, 46' can be triggered manually by, for example, a medical professional, a caregiver, or the subject. Alternatively, a set of sensing electrodes 44 can detect one of the physiological parameters associated with a meal and generate a signal to cause the delivery of an electrical stimulus which can cause inferior mesenteric artery 13 or inferior mesenteric vein 19 vasoconstriction, and decrease blood supply to the lower gastrointestinal system.

In each embodiment described above, the decrease in blood supply to the gastrointestinal (GI) system—whether to the upper GI system as depicted, for example, in FIG. 2, the middle GI system as depicted, for example, in FIG. 3, or the lower GI system as depicted, for example, in FIG. 4—can curb a subject's appetite and/or induce anorexia, satiety, and/or weight loss in the subject. In one embodiment, a subject's appetite is considered curbed or satiety is induced if, relative to a patient's historical average daily, weekly, monthly, quarterly, or yearly caloric intake, the patient is ingesting 5% or more (e.g. 10%, 20%, 30%, 40%, 50%, 60%, 70%, and on) fewer calories. In another embodiment, a subject's appetite is considered curbed or satiety is induced if, relative to a patient's historical average daily, weekly, monthly, quarterly, or yearly caloric intake, the patient is ingesting less than a threshold number of maximum calories, wherein the threshold number of maximum calories is defined based upon a patient's desired weight loss goal. In another embodiment, a subject incurs substantial weight loss if a subject has lost at least 30% of the subject's excess weight (calculated by subtracting a target weight from the subject's current weight). In another embodiment, a subject incurs substantial weight loss if a subject has lost at least 10% or more of the subject's excess weight (calculated by subtracting a target weight from the subject's current weight).

Also in each embodiment, the electrode set 21 can provide an electrical stimulus of from about 1 microampere (μAmp) up to about 100 Amp, although the methods described herein may be practiced by providing an electrical stimulation outside of this range. Typically, the amplitude of the electrical stimulus can be from about 1 milliamp (mAmp) to about 10 Amp. In some embodiments, the electrical stimulus can be less than about 10 amp such as, for example, less than 1 amp. In certain embodiments, the amplitude of the electrical stimulus can be from about 5 mAmp to about 100 mAmp such as, for example, 10 mAmp. Also, certain treatments may include multiple electrical stimuli having any combination of varying amplitudes.

An electrical stimulus "dose" can be provided continuously or intermittently. For example, an electrical stimulus may be provided one time, may be provided continuously for a prescribed period, or may be provided in a series of intermittent stimuli over a prescribed period. The prescribed period may be such as, for example, from about 1 millisecond (msec) to about one hour. Intermittent electrical stimuli may be provided at regular, prescribed intervals within the treatment period. For example, intermittent electrical stimuli, one second in length, may be provided for, for example, one hour. In other cases, intermittent electrical stimuli may be provided on an "as needed" basis. Also, certain treatments may include multiple electrical stimuli provided over any combination of varying treatment periods.

An electrical stimulus may have any pattern necessary to produce the desired result, including a square, rectangular, sinusoidal, or saw-tooth shape. Also, certain treatments may include multiple electrical stimuli including any combination of patterns.

The frequency of the electrical stimulus can be in the range of approximately 1 microHertz (μHz) to about 1 megaHertz (MHz), although the methods described herein may be practiced by administering electrical stimuli having a frequency outside of this range. Typically, an electrical stimulus may have a frequency of about 1 mHz to about 1 MHz such as, for example, a frequency of from about 0.1 Hz to about 10 Hz. In certain embodiments, an electrical stimulus may be administered at a frequency of about 1 Hz. Also, certain treatments may include multiple electrical stimuli including any combination of frequencies.

Electrodes of the electrode set 21 can be placed in the tunica intima, tunica media, tunica externa and/or adventitia of the celiac artery 11, superior mesenteric artery 12, inferior mesenteric artery 13, internal iliac artery 16, external iliac artery 17, superior mesenteric vein 18, and/or inferior mesenteric vein 19. Alternatively, electrodes of the electrode set 21 may be placed on nerves 15 supplying the celiac artery 11, superior mesenteric artery 12, inferior mesenteric artery 13, internal iliac artery 16, external iliac artery 17, superior mesenteric vein 18, and/or inferior mesenteric vein 19 or a branch of the celiac artery 11, superior mesenteric artery 12, inferior mesenteric artery 13, internal iliac artery 16, external iliac artery 17, superior mesenteric vein 18, and/or inferior mesenteric vein 19. Alternatively, electrodes of the electrode set 21 may be placed on nerves 15 supplying the celiac artery 11, superior mesenteric artery 12, inferior mesenteric artery 13, internal iliac artery 16, external iliac artery 17, superior mesenteric vein 18, and/or inferior mesenteric vein 19. The number of electrodes in a set, as well as the number of electrode sets, employed for treatment of a particular condition may be influenced by factors such as, for example, the size of the electrodes, the prescribed stimulus amplitude, frequency, and/or pattern, and the size of the desired placement area.

Figure 6:
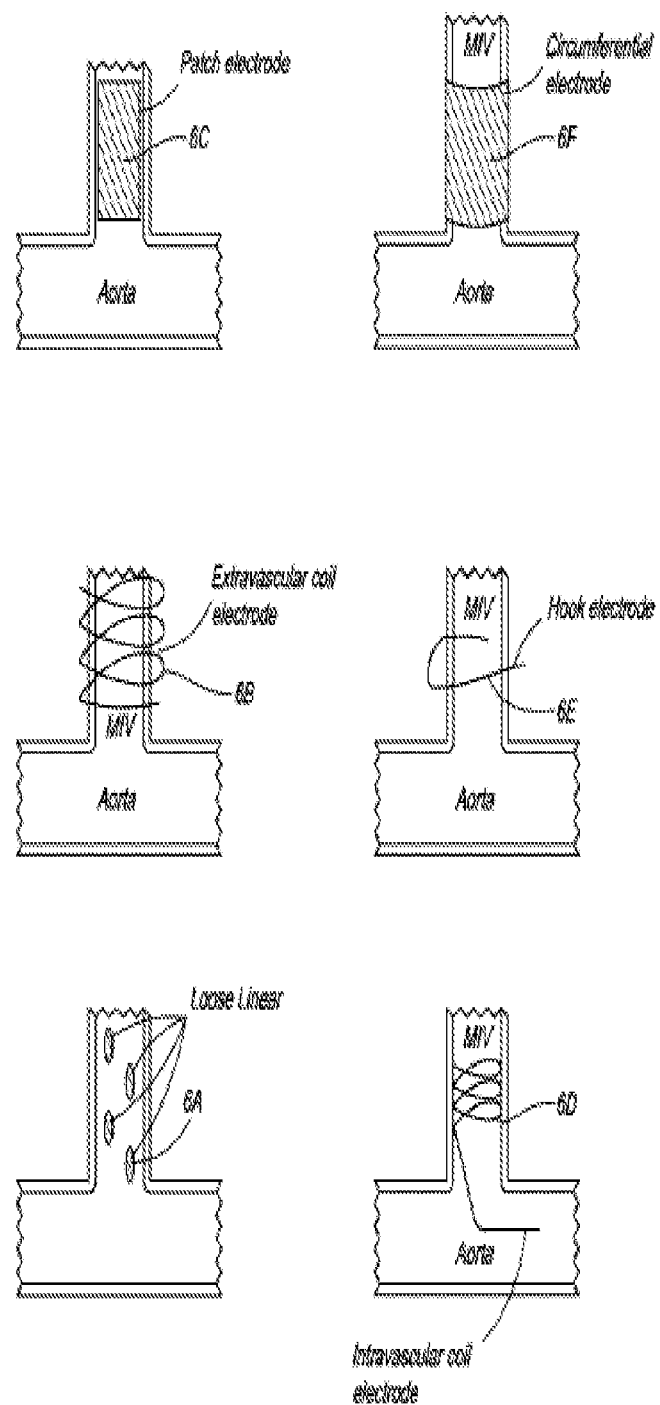
FIG. 6 illustrates exemplary forms and configurations of electrodes used in the methods disclosed herein.

FIG. 6 illustrates exemplary electrode designs, configurations, and arrangements including, for example, loose linear 6A, extravascular coil 6B, patch 6C, intravascular coil 6D, hook 6E, and circumferential 6F electrodes.

An electrical stimulus may be triggered by a transmitter external to the human body, similar to a remote transmitter for a cardiac pacemaker. With appropriate stimulus amplitude, frequency, and pattern, and appropriate treatment periods and duration, gastrointestinal diseases such as obesity can be treated without causing permanent injury to the surrounding tissue or organs.

Figure 5:
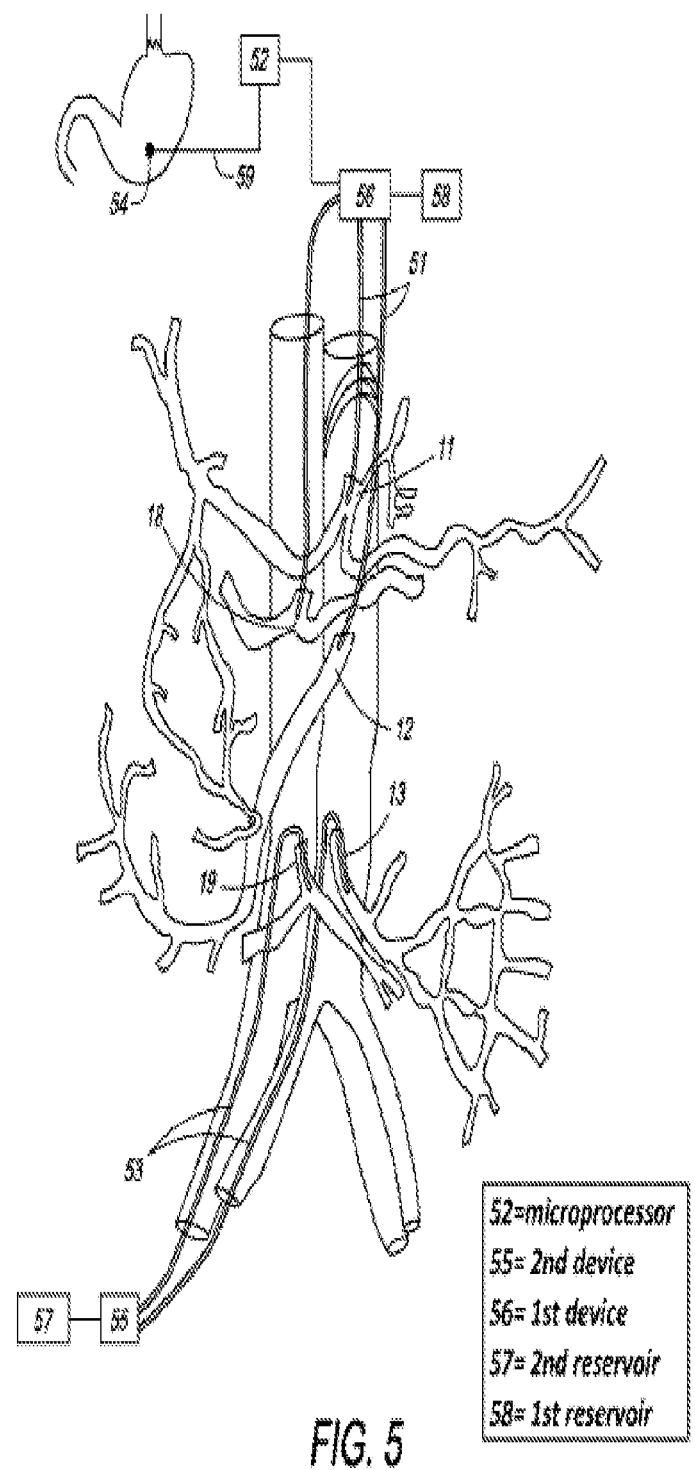
FIG. 5 is a schematic illustration of an exemplary infusion system implanted in the mesenteric circulation.

FIG. 5 shows another embodiment in which an infusion catheter 51 is placed in one or more of the celiac artery 11, superior mesenteric artery 12, or superior mesenteric vein 18 for delivery of a chemical stimulus rather than an electrical stimulus. A device comprising an infusion pump 56 is connected to a reservoir 58, which may supply a vasoactive or neuroactive chemical. The infusion catheter 51 can deliver a vasoactive or neuroactive chemical to one of the celiac artery 11, superior mesenteric artery 12, or superior mesenteric vein 18 or inferior mesenteric vein 19 to modify the blood flow to and/or from the gastrointestinal tract. This can result in gastrointestinal ischemia or congestion.

FIG. 5 also shows an embodiment in which an infusion catheter 53 is placed in one or more of the inferior mesenteric artery 13 or inferior mesenteric vein 19 for delivery of a chemical stimulus rather than an electrical stimulus. A device comprising an infusion pump 55 is connected to a reservoir 57, which may supply a vasoactive or neuroactive chemical. The infusion catheter 53 can deliver a vasoactive or neuroactive chemical to one of the inferior mesenteric artery 13 or inferior mesenteric vein 19 to modify the blood flow to and/or from the gastrointestinal tract. This can result in gastrointestinal ischemia or congestion.

A chemical stimulus "dose" can be provided continuously or intermittently. For example, a chemical stimulus may be provided one time, may be provided continuously for a prescribed period, or may be provided in a series of intermittent stimuli over a prescribed period. The prescribed period may be such as, for example, from about 0.1 μL/hr to about 1 L/min such as, for example, 0.1-10 μL/min. Intermittent chemical stimuli may be provided at regular, prescribed intervals within the treatment period. For example, intermittent chemical stimuli may be provided at a rate of 0.1 μL/min for 30 minutes. In other cases, intermittent chemical stimuli may be provided on an "as needed" basis. Also, certain treatments may include multiple chemical stimuli provided over any combination of varying treatment periods.

In some embodiments, a signal to deliver the vasoactive or neuroactive chemical may be triggered manually by, for example, a medical professional, a caregiver, or the subject. Alternatively, a set of sensing electrodes can detect one of the physiological parameters associated with a meal and generate a signal to cause the delivery of the chemical stimulus, which can affect blood supply to the gastrointestinal tract. However triggered, the signal to deliver the vasoactive or neuroactive chemical can regulate the volume, frequency, and/or pattern of vasoactive or neuroactive chemical delivered as well as the period and/or duration of the chemical stimulation. The prescribed chemical stimulus can curb a subject's appetite and/or induce anorexia, satiety, and/or weight loss in the subject.

A chemical stimulus may be triggered by a transmitter external to the human body, similar to a remote transmitter for a cardiac pacemaker. With appropriate dosing volume, frequency, and pattern, and appropriate treatment periods and duration, gastrointestinal diseases such as obesity can be treated without causing permanent injury to the surrounding tissue or organs.

Over time, stimulation, whether continuous or intermittent, whether electrical or chemical, may serve to tone the smooth muscle of the mesenteric vascular system. With sufficient tone, further stimulation may be reduced or eliminated. Thus, diseases of the gastrointestinal tract may be treated successfully using treatments of varying durations. For example, certain conditions may be treated successfully using a single treatment, while other conditions may require a more extended treatment such as, for example, one week, one month, six weeks, one year, or, in some cases, long term (including, e.g., life-long) treatment may be required.

Referring simultaneously to FIGS. 2 through 4, in some embodiments, the device 26, 36, 46, 56 may be controlled by a microprocessor 22, 32, 42, 52. In some embodiments, the microprocessor 22, 32, 42, 52 may be operably connected to the signal generator and may be programmed to control the length, power, and frequency of the electrical signals generated by the device 26, 36, 46, 56 over various treatments periods and/or durations. In other embodiments, the microprocessor 22, 32, 42, 52 may be operably connected to the pump and may be programmed to control the length, volume, and frequency of the chemical signals generated by the device 26, 36, 46, 56 over varying treatments periods and/or durations.

In one exemplary embodiment, a subject can signal the ingestion of a meal using a remote control RF signaling device. Based on subject's desired weight loss, a microprocessor in the implanted signal generating device can send multiple trains of pulses after a preset time delay. In the case of, for example, a male subject for which a 150 pound weight loss is desired and a 1000 calorie daily diet is suggested, the preset time to start mesenteric vascular stimulation may be 10 minutes from the initiation of eating. A typical stimulation parameter can have a burst of, for example, 6 rectangular pulses of, for example, 2 msec duration and pulse amplitude of, for example, 10 mAmp. The duration of each single burst of 6 impulses may be, for example, 200 msec and have a frequency of, for example, 1 burst per second. The pulse trains may be interrupted by a quiescent phase of, for example, 800 msec. A quiescent phase may, for example, allow the mesenteric vascular musculature to repolarize. The pulse trains can induce contraction of, for example, the celiac and superior mesenteric artery, resulting in physiological obstruction to the flow of blood to the stomach and intestine. This can cause discomfort and/or pain, resulting in early satiety and/or loss of appetite in the subject.

The stimulation may continue until subject stops eating, after which the stimulation stops. Alternatively, sensors can be implanted in the gastrointestinal tract that sense ingestion of food and trigger the microprocessor which, in turn, triggers the signal generator to deliver stimulations to the celiac and superior mesenteric artery. The sensors also may detect the end of ingestion and transmit a shut off signal to the microprocessor which, in turn, will shut off the stimulator.

Based on a subject's continuing caloric restriction, the stimulation patterns can be adjusted by the subject's physician using an external remote controller without requiring additional surgery. Upon achieving desired weight loss, the stimulator can be remotely shut down and, if the subject starts gaining the weight back, the stimulator can be remotely turned on.

In certain embodiments, the methods described herein may be practiced using a neurostimulation system having at least one electrode set, at least one power source, and an extension connecting the power source to the electrode set. The electrode can be integrated into a lead, where the lead is a small conductor with more than one electrode integrated therein. In one embodiment, surgically implanted leads may be used including, for example, a 3587A RESUME II Lead, 3986 RESUME TL Lead, 3998 SPECIFY Lead, 3999 Hinged SPECIFY Lead, 3982 SYMMIX Lead, and/or 3987 On-Point PNS Lead (all from Medtronic, Inc., Minneapolis, Minn.), or any other quadripolar leads with plate electrodes capable of creating multiple stimulation combinations over a broad area of paresthesia.

In one embodiment, device 26, 36, 36', 46, 56 may be an implantable battery-powered neurostimulator with non-invasive programmability, such as, for example, an ITREL 3, a SYNERGY, a SYNERGYPLUS+, or a SYNERGYCOMPACT+ (all from Medtronic, Inc., Minneapolis, Minn.). Alternatively, the device 26, 46', 55 comprises a radio-frequency (RF) system, which can include an implanted receiver that detects radio-frequency signals through the skin from an external power source or transmitter such as MATTRIX transmitters (Medtronic, Inc., Minneapolis, Minn.).

In another embodiment, the extension may be a small conductor that electrically connects the power source to the lead. Exemplary extensions include low profile, low impedance extensions and/or bifurcated, low profile, low impedance extensions.

As shown in FIGS. 2 through 4, the present invention can optionally include additional sensing electrodes 24, 34, 44, 54 that are placed in the gastrointestinal tract or proximate to nerves supplying the gastrointestinal tract or the vascular system. The sensing electrodes 24, 34, 44, 54 may be capable of sensing one or more physiological stimuli such as, for example, esophageal peristalsis, esophageal pH, esophageal impedance, esophageal pressure, esophageal electrical activity, lower esophageal sphincter (LES) pressure, LES electrical activity, gastric peristalsis, gastric electrical activity, gastric chemical activity, gastric hormonal activity, gastric temperature, gastric pressure, gastric impedance and gastric pH, duodenal peristalsis, duodenal electrical activity, duodenal chemical activity, duodenal hormonal activity, duodenal temperature, duodenal pressure, duodenal impedance and duodenal pH, blood chemical activity, blood hormonal activity, vagal or other gastrointestinal neural activity, salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, or biliary sphincter electrical activity, mesenteric vascular pressure, mesenteric vascular flow, and/or mesenteric vascular chemical contents.

Upon sensing an appropriate physiological stimulus, the sensing electrodes 24, 34, 44, 54 can transmit a signal to the device 26, 36, 46, 56, via wire or lead 29, 39, 49, 59 and processor 22, 32, 42, 52. The device 26, 36, 46, 56 may then begin, maintain, modulate, or stop electrical stimulation signal sent to the electrode set 21. Thus, the methods described herein can be more responsive to a subject's particular biological state and precisely modulate at least a portion of the mesenteric vasculature so that a part or the whole of the mesenteric system can contract or relax, thereby regulating the flow of blood into the gastrointestinal tract. Controlling the flow of blood into the gastrointestinal tract can also be achieved by turning off the transmitter of the external pacer. The stimulating electrode set 21 can be used in combination with additional pacing electrodes, as are known in the art, to treat disorders of gastrointestinal motility or function. It should be appreciated that the sensing electrodes can be implemented in any of the embodiments of this invention, including those depicted in FIGS. 3-5.

Any of the stimulating or sensing electrode sets can be placed by conventional surgical, laparoscopic, endoscopic, radiological, or other minimally invasive vascular and surgical techniques to place the desired device or devices on or adjacent to or in communication with the structure with which it is to be associated. Conventional electrode stimulation devices may be used to practice the methods described herein.

It should be appreciated that where a cardiovascular condition, such as angina, is being treated, periods of stimulation may last much longer than in treating conditions related to inducing satiety or curbing a subject's appetite. In one embodiment, the treatment of angina would be effectuated by stimulating both the celiac and SMA arteries, as described above, concurrently for a period of several hours, such as 2, 3, 4, 5, 6, or more, after a meal.

The present invention is illustrated by the following examples. It is to be understood that the particular examples, materials, amounts, and procedures are to be interpreted broadly in accordance with the scope and spirit of the invention as set forth herein.

Example 1

A mesenteric electrical stimulator is laparoscopically implanted into an adult male subject. The stimulator leads are implanted on the external surface of the celiac and superior mesenteric artery and the microcontroller is implanted in a pocket in the anterior abdominal wall.

Using remote control signals, the microcontroller sends multiple bursts of 10 rectangular pulses after a preset time delay of 10 minutes from the beginning of the meal. The microcontroller sends electrical stimuli having a pulse amplitude of 10 mAmp and a burst frequency of 2 bursts per second. The pulse trains are interrupted by a quiescent phase of 500 milliseconds (msec). The stimulation is carried out until patient stops eating after which the stimulation stops.

Example 2

In acute experiments, mesenteric vascular stimulation is implanted into the mesenteric vasculature of a pig. The stimulator leads are implanted on the external surface of the celiac and superior mesenteric artery and is controlled by an external microcontroller. A typical stimulation parameter can have a burst of 10 pulses with a pulse amplitude of 20 mAmp and a burst frequency of 0.5 bursts per second. The duration of each bursts of 10 pulses is 400 msec with quiescent phase of 1600 msec to allow for repolarization of the mesenteric vascular muscle. The pulse trains will induce contraction of the celiac and superior mesenteric artery resulting in physiological obstruction to the flow of blood to the stomach and intestine. The decrease in the blood flow can be measured using a Doppler flow meter.

Example 3

For chronic survival experiments, the stimulator is implanted into the mesenteric vasculature of the pig. The stimulator leads are implanted on the external surface of the celiac and superior mesenteric artery and the microcontroller is implanted in a pocket in the anterior abdominal wall or worn on a jacket or belt. A typical stimulation parameter can have a burst of 10 pulses with a pulse amplitude of 10 mAmp, duration of 400 msec and a burst frequency of 0.5 bursts per second. The burst trains are interrupted by a quiescent phase of 1600 msec to allow for repolarization of the mesenteric vascular muscle. The stimulator is turned on and off randomly and the food intake during on periods is compared to off period documenting lower food and calorie intake when the stimulator is on. In addition stimulator can be turned on continuously. The animal is allowed to free feed. Serial weight measures shows less weight gain or weight loss compared to free fed animals that do not have the stimulator turned on.

Preventing, Treating, and/or Controlling Hemorrhages

In various embodiments, the present specification provides a method for regulating blood flow for treating a hemorrhage or preventing an anticipated hemorrhage. Generally, the control of blood flow through arteries and veins is accomplished by administering a stimulus to either the vessels that supply blood or nerves that control those blood vessels. The vessel or the nerve can be stimulated directly or indirectly. In various embodiments, one or more electrodes of a stimulation apparatus is placed proximate, or in electrical communication with, an artery supplying blood to the body organ, a vein supplying blood from the body organ, a nerve supplying said artery or said vein, or a wall of said body organ. In various embodiments, proximate, or in electrical communication with, is defined as a location at a distance ranging from 0 to 5 cm from a target artery supplying blood to the body organ, a vein supplying blood from the body organ, a nerve supplying said artery or said vein, or a wall of said body organ. In various embodiments, the location is also at least 1 cm upstream from a hemorrhage or a position on a blood vessel where a hemorrhage is expected to occur. In other words, in various embodiments, the preferred stimulation site at least 1 cm proximal to, or upstream from, the site of injury or operation.

In an embodiment, the present specification provides a method of modulating blood flow to an organ by applying an electrode proximate to an artery, a vein, or a nerve supplying an artery and vein corresponding to the organ, and activating the electrode to provide an electrical stimulus constricting the artery or vein. In various embodiments, providing electrical stimulation may be used to treat hemorrhage, control/stop bleeding, and treat tumors.

In some embodiments, the presently disclosed methods for treating, controlling, or preventing a hemorrhage are only practiced in high risk patients, including patients with liver disease, patients having blood coagulation disorders, or patients on anticoagulant medications, such as aspirin, Plavix, Coumadin, and/or Xarelto. In some embodiments, the presently disclosed methods are practiced in certain surgeries where the risk of causing a hemorrhage is high, including hepatobiliary surgery, having a risk of a hemorrhage in the hepatic artery and/or portal vein, a splenectomy having a risk of a hemorrhage in the splenic vein, a vascular tumor resection having a risk of a hemorrhage in the feeding tumor artery, a Whipple procedure having a risk of hemorrhage in the pancreaticoduodenal artery, a femoral-popliteal bypass having a risk of hemorrhage in the femoral artery and an aortic dissection having a risk of hemorrhage in the aorta. The methods disclosed herein are practiced in order to minimize, prevent, control, or treat a hemorrhage occurring in each of the above listed artery or vein locations.

Microsecond or millisecond electrical pulses can induce vasoconstriction within a few seconds, in both arteries and veins. Upon termination of stimulation, the blood vessels dilate back to their original size within a few minutes. This reversible vasoconstriction may be repeated without causing any tissue damage. Upon stronger stimulation, a permanent blood clot may form, completely blocking the lumen of the blood vessel. Both the reversible vasoconstriction and irreversible clotting offer a powerful approach to hemorrhage prevention and/or control in non-compressible wounds. The extent of perfusion can be controlled by varying the amplitude, pulse duration, and pulse repetition rate.

The therapeutic basis of electro-surgery is the production of heat at the cellular level. A high frequency alternating current >100 KHz (~350K Hz) flowing through a tissue produces heat and the duty cycle of the current is used to create a desired tissue effect of cutting or coagulation. A temperature of 104° F. causes reversible cell trauma while a temperature of 120° F. causes irreversible cell trauma. Higher temperatures cause further changes in body tissues. For example, 158° F. causes coagulation, 212° F. causes a cutting effect and 392° F. causes carbonization fulguration. However, stimulating a tissue with a lower frequency (<100 KHz) electrical current produces neural stimulation without producing heat.

Conventional thermal coagulation of blood vessels typically requires tens of watts of power delivered by electro-cautery or RF coagulator. Such techniques cause significant tissue injury and are not efficient in coagulation of large vessels. Typically, large vessels require mechanical ligation under direct visualization. Newer techniques, such as Ligasure, can thermally seal larger arteries, but they require bulky power supply, good visualization of the vessel and access to the vessel from all sides for accurate positioning of the surgical probe, all of which prevent the use of this technology in the field. Additionally, there is significant delay in hemorrhage control due to limitations of these technologies, resulting in significant blood loss before adequate hemorrhage control can be achieved, in turn resulting in a need for blood transfusion and associated risks.

In contrast, low-power (few mW) electrical vasoconstriction helps reduce blood flow without thermal damage to the tissue, and may not require good visualization of the injured vessel for positioning of the tool. Since very low power is required for such stimulation, a small disposable device, such as a device having electrodes as described with reference to FIG. 6, may be placed in the wounded area to reduce or stop local bleeding. The device can be placed prior to a hemorrhage or during a hemorrhage to either prevent or treat a hemorrhage. Additionally, blood is a good conductor of electricity and hence a perfect contact between the electrode and blood vessel may not be necessary for adequate hemorrhage control. Additionally, an artery, vein or nerve distant from the site of injury can be stimulated to achieve hemorrhage control. A temporary decrease in blood perfusion can be achieved in seconds using the reversible vasoconstriction regime, with vessels dilating back to their original size within minutes after termination of stimulation. This modality could be used for non-damaging hemorrhage control in surgery and during trauma care. Permanent blockage of bleeding is achieved upon vasoconstriction followed by initiation of clotting. Additionally, the therapy could be repeated multiple times to treat delayed hemorrhage from a site.

Figure 7A:
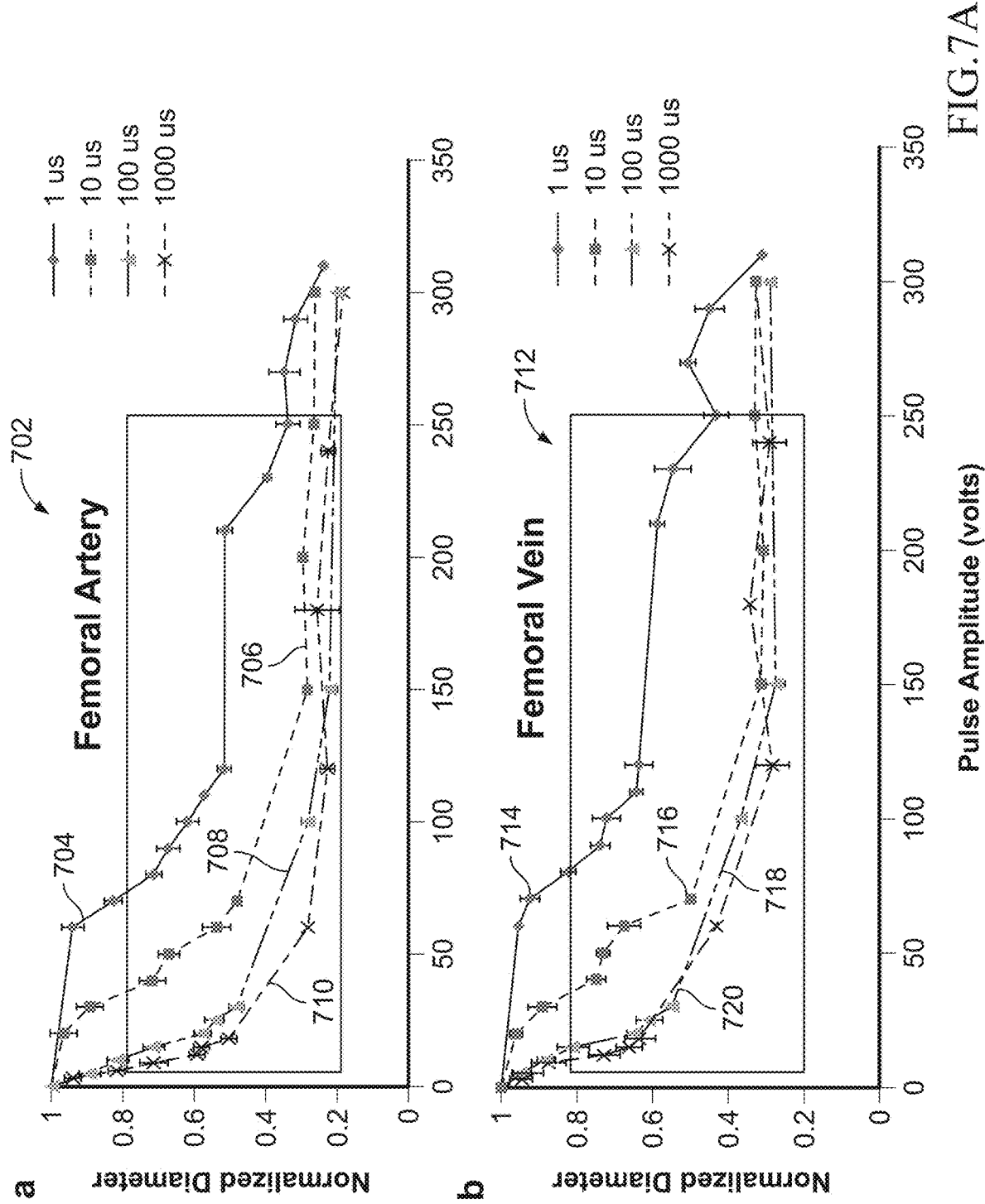
FIG. 7A depicts graphs illustrating constriction of femoral vessels in response to stimulation as a function of normalized diameter and pulse amplitude.

Stimulating blood vessels with pulses of electric current causes a local constriction of both femoral and mesenteric arteries and veins as described in the preceding sections of the present specification. It has been observed that biphasic (symmetric, anodic-first square) pulses of electric current with duration of 1 millisecond per phase, having an amplitude of 250 V and a repetition rate of 10 Hz cause, within seconds, a very pronounced local constriction of both femoral and mesenteric arteries and veins. FIG. 7A illustrates the extent of the constriction of femoral vessels in response to 10 second long stimulation at a 1 Hz repetition rate as a function of stimulus amplitude and vessel diameter. Graph 702 illustrates the constriction of a femoral artery, wherein: plot 704 represents constriction when the stimulation is provided for one microsecond, plot 706 represents constriction when the stimulation is provided for 10 microseconds, plot 708 represents constriction when the stimulation is provided for 100 microseconds, and plot 710 represents constriction when the stimulation is provided for 1000 microseconds. Similarly, graph 712 illustrates the constriction of a femoral vein, wherein: plot 714 represents constriction when the stimulation is provided for one microsecond, plot 716 represents constriction when the stimulation is provided for 10 microseconds, plot 718 represents constriction when the stimulation is provided for 100 microseconds, and plot 720 represents constriction when the stimulation is provided for 1000 microseconds.

Figure 7B:
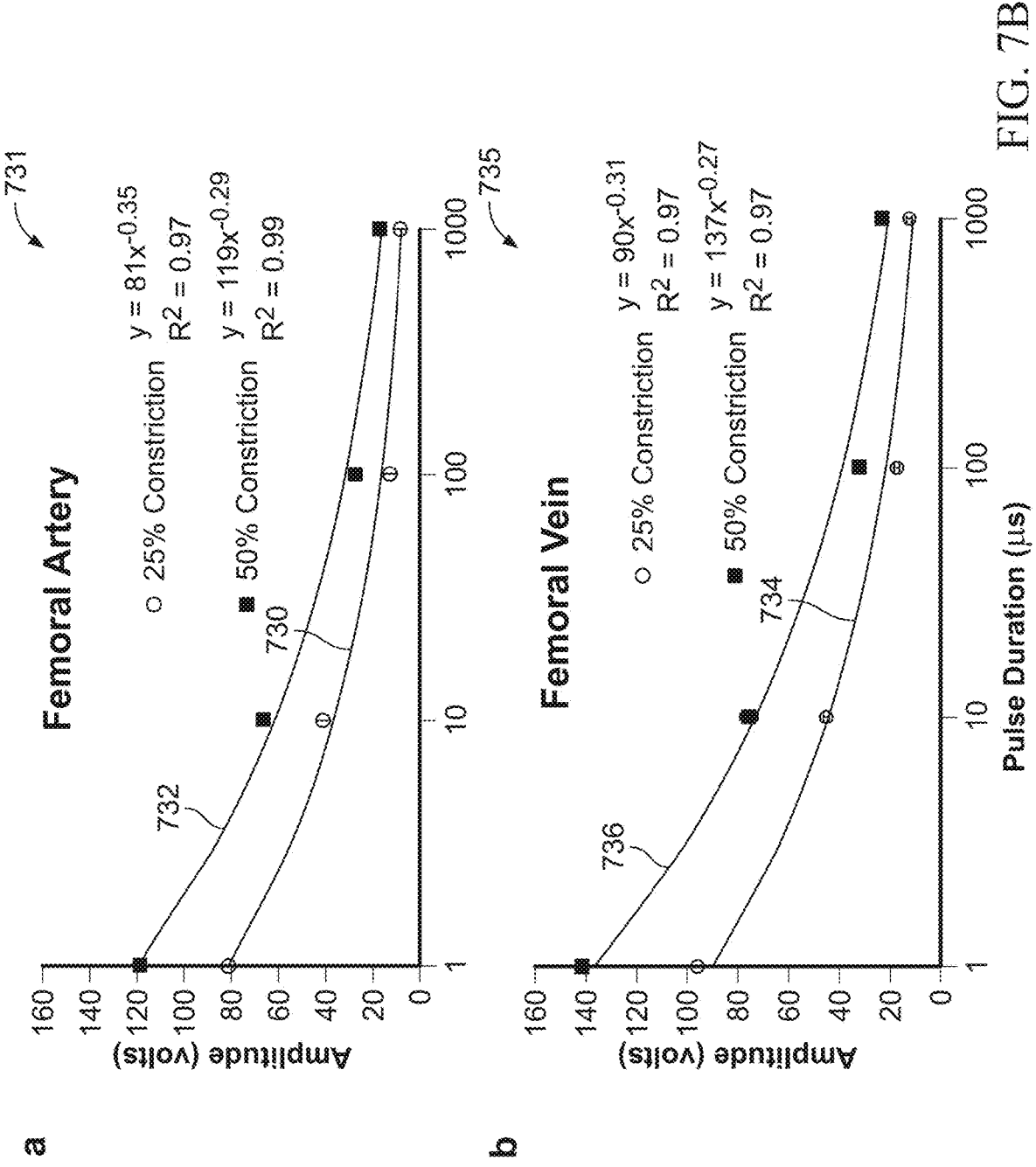
FIG. 7B depicts graphs illustrating constriction of femoral vessels in response to stimulation as a function of pulse amplitude and pulse duration.

As can be observed from FIG. 7A, vasoconstriction increases with higher pulse amplitude and longer duration for both arteries and veins. Further FIG. 7A illustrates that vessel diameter decreases with increasing pulse amplitudes along a sigmoid curve, having a response threshold on the lower end, and reaches a minimum size of about 20-25% of the original diameter on the high end. FIG. 7B illustrates the extent of the constriction of femoral vessels as a function of stimulus pulse amplitude and pulse duration. Plots 730 and 732 of graph 731 correspond to 25% and 50% constriction, respectively, in a femoral artery. Plots 734 and 736 of graph 735 correspond to 25% and 50% constriction, respectively, in a femoral artery. In various embodiments, a percentage of vasoconstriction of a blood vessel such as an artery or a vein may be defined as the percent of closure achieved, calculated by subtracting the stimulated, constricted diameter from the unstimulated, unconstructed diameter and dividing that difference by the unstimulated, unconstricted diameter and may be measured by using a Doppler study or an angiogram or any other method known in the art.

As is demonstrated by FIG. 7B, strength-duration dependence of the 25% and 50% constriction thresholds may be approximated by a power dependence 't2a', where the value of 'a' is approximately 0.3 for femoral arteries and veins. Further, as is illustrated in FIGS. 7A and 7B, for all pulse durations, lower voltage is required to reach similar constriction in arteries, compared to veins, although the difference decreases when the stimulation is applied for longer durations.

Figure 7C:
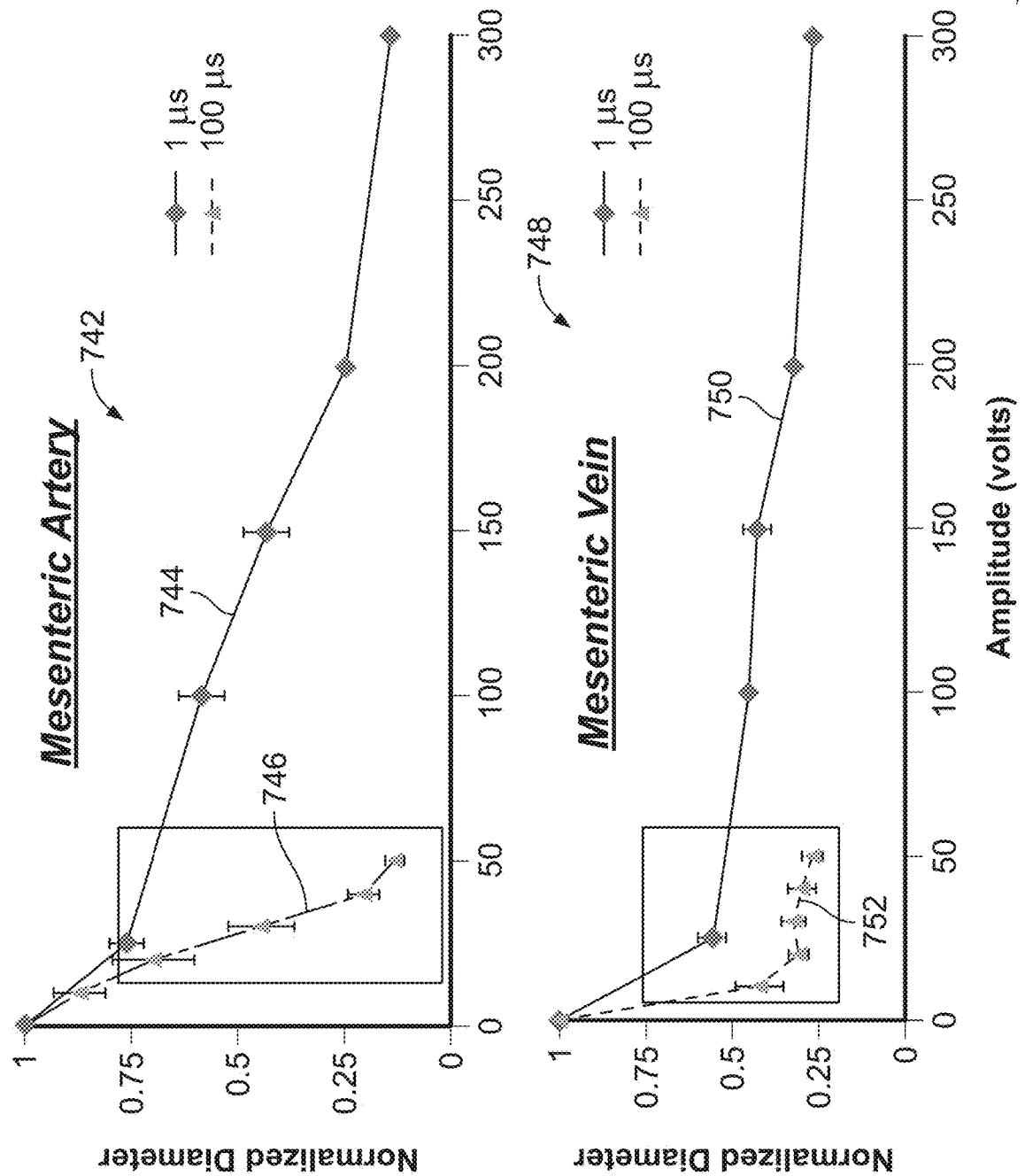
FIG. 7C depicts graphs illustrating constriction of mesenteric vessels in response to stimulation as a function of pulse amplitude and pulse duration.

FIG. 7C illustrates the extent of the constriction of mesenteric vessels in response to 10 second long stimulation at a 1 Hz repetition rate as a function of stimulus amplitude and vessel diameter. Graph 742 illustrates the constriction of a mesenteric artery, wherein plot 744 represents constriction when the stimulation is provided for one microsecond and plot 746 represents constriction when the stimulation is provided for 100 microseconds. Similarly, graph 748 illustrates the constriction of a mesenteric vein, wherein plot 750 represents constriction when the stimulation is provided for one microsecond and plot 752 represents constriction when the stimulation is provided for 100 microseconds. Mesenteric blood vessels display a similar kind of response as that of the femoral arteries and veins. For the same pulse parameters, the extent of vasoconstriction in mesenteric arteries is higher than in femoral arteries, and the difference increases with larger amplitudes. For example, with 1 μs pulses at 200 V, mesenteric arteries constrict by 76%, as compared to 49% reduction in femoral arteries. Mesenteric veins constrict more than the femoral veins at low amplitudes, while this ratio reverses at higher amplitudes.

In an experimental setup, femoral and mesenteric arteries of test subjects were cut and then some of these were subjected to electrical stimulation. The experiment illustrated that the blood loss from the cut arteries that were subjected to electrical stimulations of pre-defined amplitude for a pre-defined period was far less than the blood loss from the cut arteries that were left untreated. FIG. 8A illustrates a graph displaying blood loss from a femoral artery with and without application of electrical stimulation. Plot 802 represents blood loss when a cut femoral artery was not treated with electric stimulation. Plot 804 represents a cut femoral artery stimulated for 30 seconds with 100 microsecond pulses of 30 V at 1 Hz and plot 806 represents a cut femoral artery stimulated for 30 seconds with 100 microsecond pulses of 150 V at 10 Hz. FIG. 8B illustrates a graph displaying blood loss from a mesenteric artery with and without application of electrical stimulation. Plot 808 represents blood loss when a cut mesenteric artery was not treated with electric stimulation and plot 810 represents a cut mesenteric artery stimulated for 30 seconds with 100 microsecond pulses of 40 V at 1 Hz. In both the blood vessels types, treatment caused decrease or even complete stoppage of bleeding after stimulation, while continuous bleeding was observed in the untreated arteries.

Figure 8C:
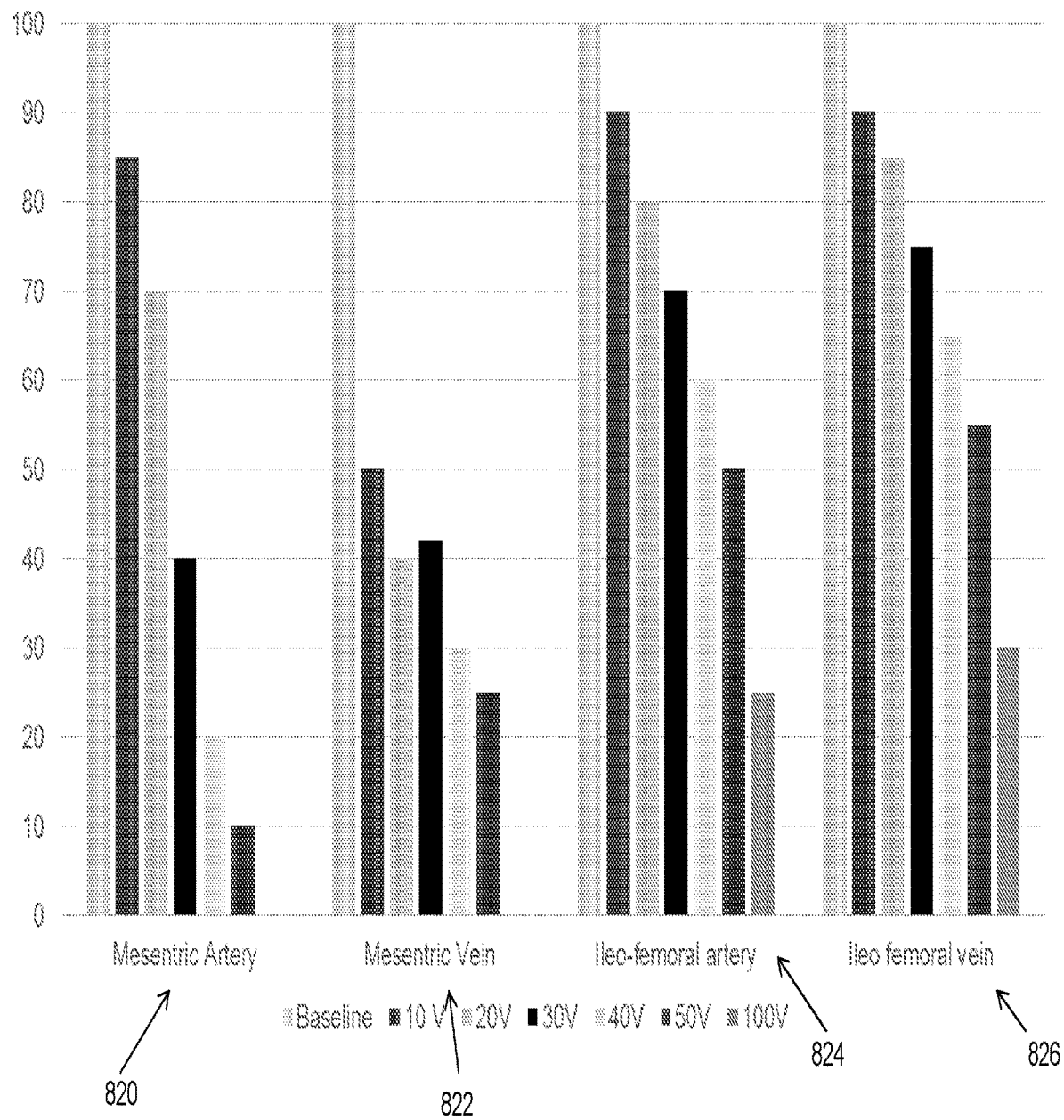
FIG. 8C illustrates a graph displaying constriction of blood vessels upon application of electrical stimulation for 100 μsec at a frequency of 10 Hz.

FIG. 8C illustrates a series of graphs displaying constriction of blood vessels upon application of electrical stimulation for 200 microseconds at a frequency of 10 Hz. Plot sets 820, 822, 824 and 826 illustrate the constriction of a mesenteric artery, mesenteric vein, ileo-femoral artery and ileo-femoral vein respectively. As shown, upon application of no voltage, i.e. baseline voltage, there is no constriction in any of the blood vessels and they are 100% open. Upon increasing the applied voltage in intervals of 10V-50V over a range of 0 V to 100 V, the blood vessels steadily constrict. Hence, the graphs illustrates that upon increasing the applied voltage, the constriction of blood vessels increases. Also, it can be seen from FIG. 8C that the application of voltage causes a larger degree of constriction in the mesenteric artery and veins 820, 822 as compared to the ileo-femoral artery and vein 824, 826.

Figure 8D:
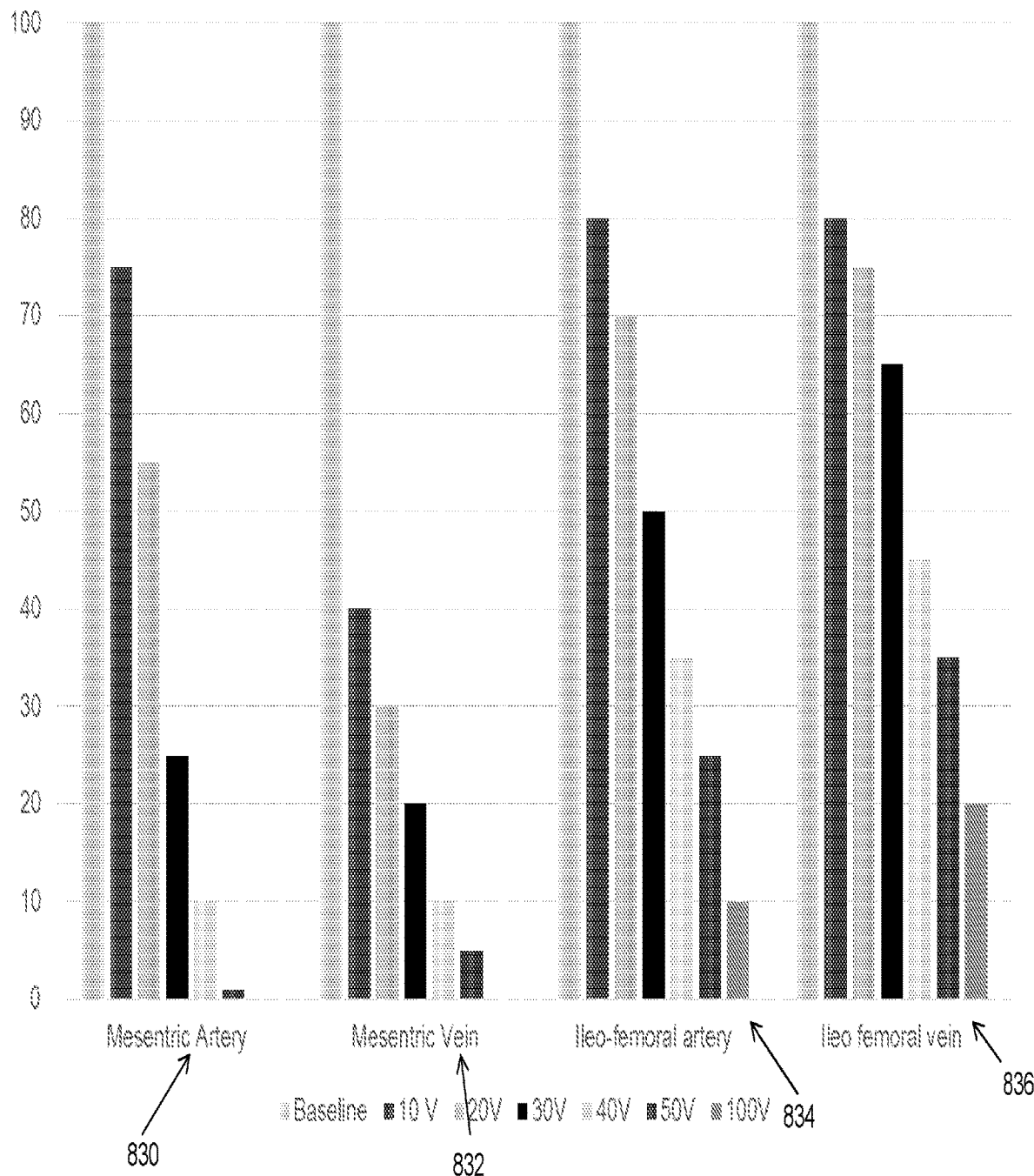
FIG. 8D illustrates a graph displaying constriction of blood vessels upon application of electrical stimulation for 1 msec at a frequency of 10 Hz.

FIG. 8D illustrates a series of graphs displaying the constriction of blood vessels upon application of electrical stimulation for 1 ms at a frequency of 10 Hz. Plot sets 830, 832, 834 and 836 illustrate the constriction of a mesenteric artery, mesenteric vein, ileo-femoral artery and ileo-femoral vein respectively. As shown, upon application of no voltage, i.e. baseline voltage, there is no constriction in any of the blood vessels and they are 100% open. Upon increasing the applied voltage in intervals of 10V-50V over a range of 0 V to 100 V, the blood vessels steadily constrict more and more. Hence, the graphs illustrates that upon increasing the applied voltage, the constriction of the blood vessels increases. Also, it can be seen from FIG. 8D that the application of voltage causes a larger degree of constriction in the mesenteric artery and veins 830, 832 as compared to the ileo-femoral artery and vein 834, 836. Similar results can be achieved from stimulation of a carotid artery or its branch, a subclavian artery or vein or their branches, a jugular vein or its branch, or any other artery or vein or nerve supplying an artery or a vein.

In various embodiments, electrodes, such as but not limited to those described with reference to FIG. 6, may be used to provide stimulation to blood vessels for treating hemorrhage conditions. Electrodes may also be used for the application of electric stimulation to control blood loss while body organs are being operated upon. In various embodiments, the electrical stimulus provided to blood vessels, nerves, or organ walls has a pulse duration ranging from 1 μsec to 500 msec, a pulse amplitude ranging from 1 V to 250 V, and a pulse frequency ranging from 1 Hz to 100 kHz. In various embodiments, a system for treating hemorrhage includes at least one electrode in communication (wired or wirelessly) with a pulse generator. Optionally, the system further includes a microprocessor operably connected to the IPG which controls stimulation parameters generated by the IPG and administered by the at least one electrode.

Figure 9A:
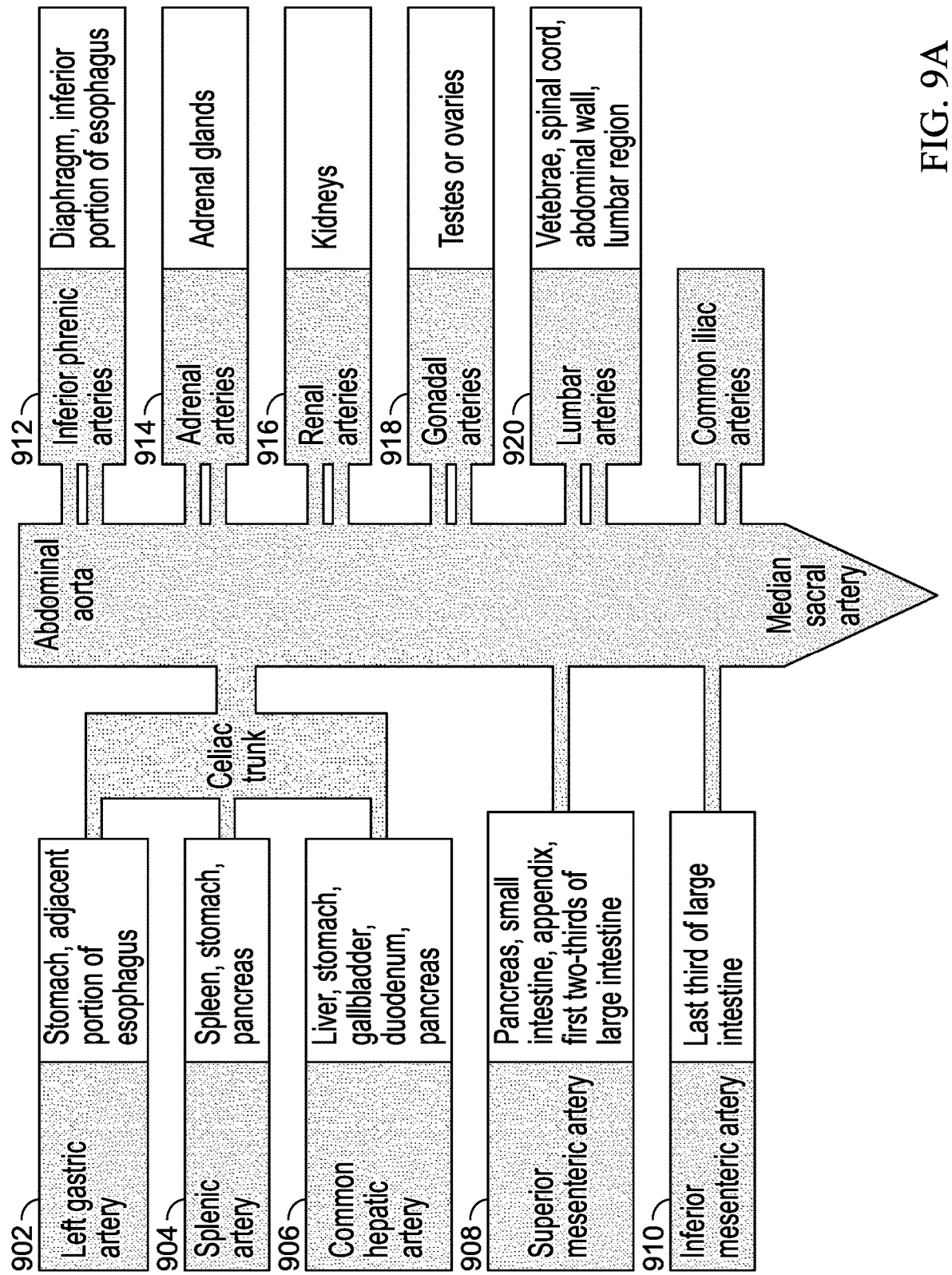
FIG. 9A illustrates arterial sites of application of electrodes corresponding to organs being operated upon.

FIG. 9A illustrates arterial sites of application of electrodes corresponding to organs being operated upon. Blood is supplied to a stomach, duodenum, gallbladder and liver via a celiac artery or a branch of a celiac artery; to a pancreatic head via a celiac artery and a superior mesenteric artery or a branch of a celiac or superior mesenteric artery; to a jejunum and ileum and a vermiform appendix via a superior mesenteric artery or a branch of a superior mesenteric artery; to a colon via a superior mesenteric artery, inferior mesenteric artery or a branch of a superior or inferior mesenteric artery; to a spleen via a splenic artery or a branch of a splenic artery; to a genitourinary system via a renal artery, common iliac, internal iliac artery or a branch of a renal artery, common iliac, and internal iliac artery. Hence, an electrode may be placed in a left gastric artery 902 for providing electrical stimulation to constrict blood vessels and modulate blood flow to a stomach and adjacent portion of an esophagus; in a splenic artery 904 for providing electrical stimulation to constrict blood vessels and modulate blood flow to a spleen, stomach, and pancreas; in a common hepatic artery 906 for providing electrical stimulation to constrict blood vessels and modulate blood flow to a liver, gallbladder, duodenum and pancreas; in a superior mesenteric artery 908 for providing electrical stimulation to constrict blood vessels and modulate blood flow to a pancreas, small intestine, appendix, and first two thirds of a large intestine; in an inferior mesenteric artery 910 for providing electrical stimulation to constrict blood vessels and modulate blood flow to a last third of a large intestine; in inferior phrenic arteries 912 for providing electrical stimulation to constrict blood vessels and modulate blood flow to a diaphragm and inferior portion of an esophagus; in adrenal arteries 914 for providing electrical stimulation to constrict blood vessels and modulate blood flow to adrenal glands; in renal arteries 916 for providing electrical stimulation to constrict blood vessels and modulate blood flow to kidneys; in gonadal arteries 918 for providing electrical stimulation to constrict blood vessels and modulate blood flow to testes or ovaries; and in lumbar arteries 920 for providing electrical stimulation to constrict blood vessels and modulate blood flow to vertebrae, spinal cord, abdominal wall, and lumbar region.

Figure 9B:
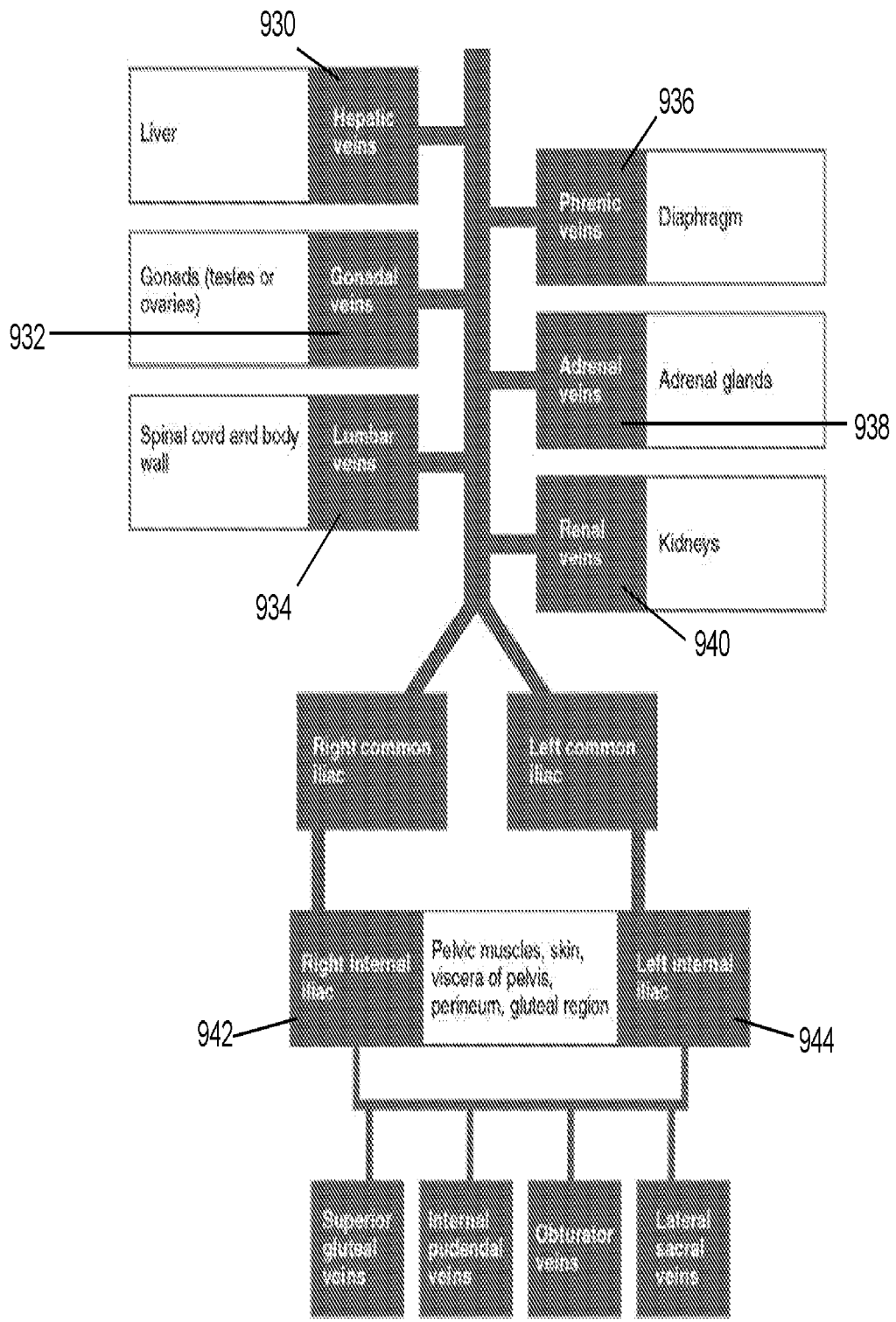
FIG. 9B illustrates venous sites of application of electrodes corresponding to organs being operated upon.

FIG. 9B illustrates venal sites of application of electrodes corresponding to organs being operated upon. Blood is directed from a stomach, duodenum, gallbladder and liver and pancreatic head via a portal vein, superior mesenteric vein or a branch thereof; from a jejunum and ileum and vermiform appendix via a superior mesenteric vein or a branch thereof; from a colon via a superior mesenteric vein, inferior mesenteric vein or a branch thereof; from a spleen via a splenic vein or a branch thereof; and from a genitourinary system via a renal vein, gonadal vein interior iliac vein or a branch thereof. Hence, an electrode may be placed in hepatic veins 930 for providing electrical stimulation to constrict blood vessels and modulate blood flow from a liver; in gonadal veins 932 for providing electrical stimulation to constrict blood vessels and modulate blood flow from gonads; in lumbar veins 934 for providing electrical stimulation to constrict blood vessels and modulate blood flow from a spinal cord and body wall; in phrenic veins 936 for providing electrical stimulation to constrict blood vessels and modulate blood flow from a diaphragm; in adrenal veins 938 for providing electrical stimulation to constrict blood vessels and modulate blood flow from adrenal glands; in renal veins 940 for providing electrical stimulation to constrict blood vessels and modulate blood flow from kidneys; and in a right 942 or left 944 internal iliac vein for providing electrical stimulation to constrict blood vessels and modulate blood flow from pelvic muscles, skin, viscera of pelvis, perineum and gluteal region.

Figure 10A:
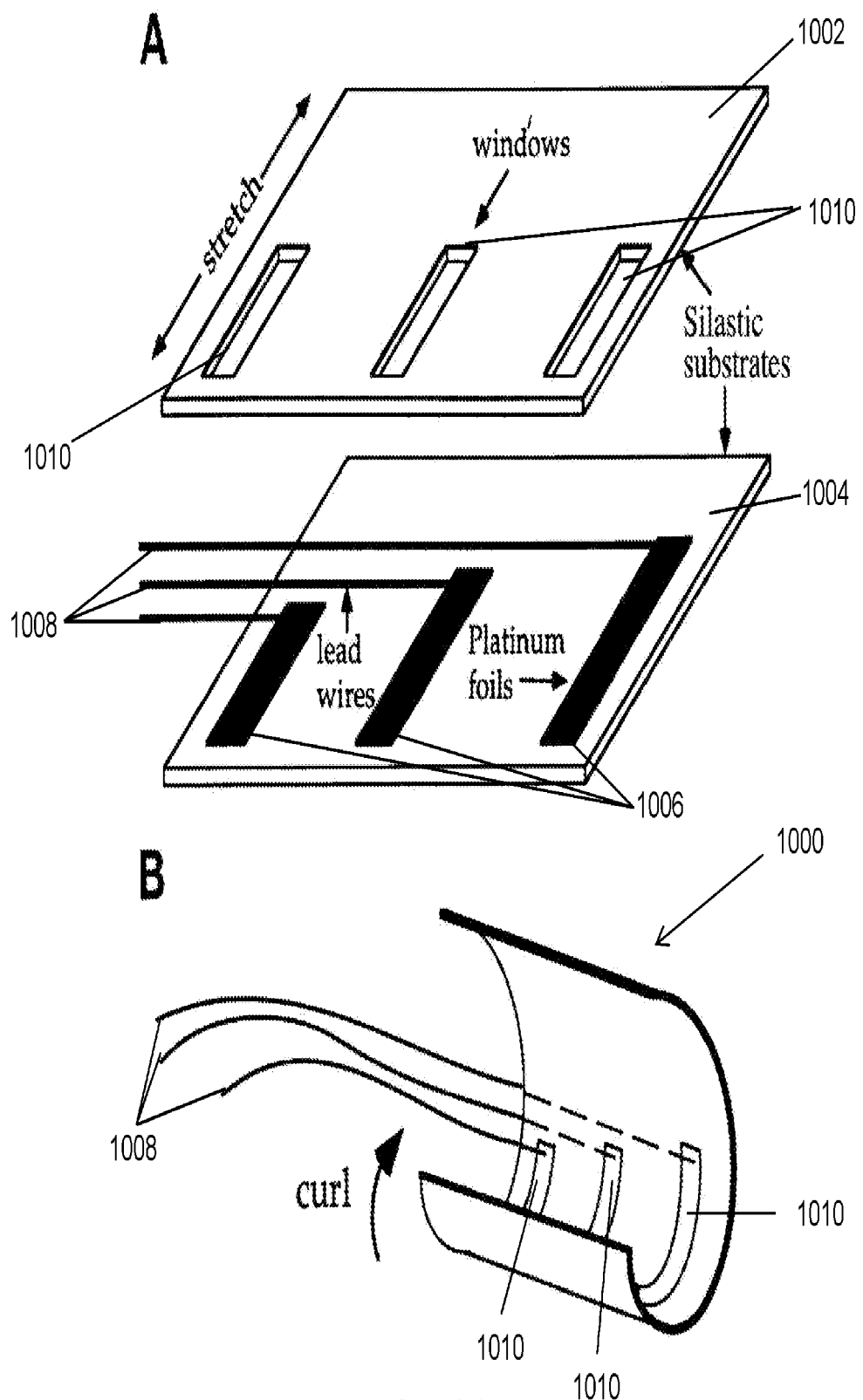
FIG. 10A illustrates an exemplary cuff electrode used for providing electrical stimulation in accordance with various embodiments of the present specification.

In an embodiment, a cuff electrode is used to provide the desired stimulation to blood vessels. FIG. 10A illustrates an exemplary cuff electrode. The spiral cuff electrode 1000 wraps around a blood vessel and, because of its self-coiling property, adjusts its diameter to the size of the blood vessel. In some embodiments, the spiral cuff electrode 1000 consists of two layers of silicone, plastic, or Silastic® substrate sheets 1002, 1004 bound together. Metal bands 1006, such as platinum-foil bands, are placed between the layers 1002, 1004 to provide electrical contact with a blood vessel (not shown in the figure). The bands 1006 are welded to lead wires 1008, for example, Teflon-insulated multi strand stainless steel lead wires, for electrical connection. Windows 1010 which, in some embodiments, are approximately 1 mm wide, are cut inside the cylinder over the platinum bands 1006 to make electrical contacts with the blood vessels.

Figure 10B:
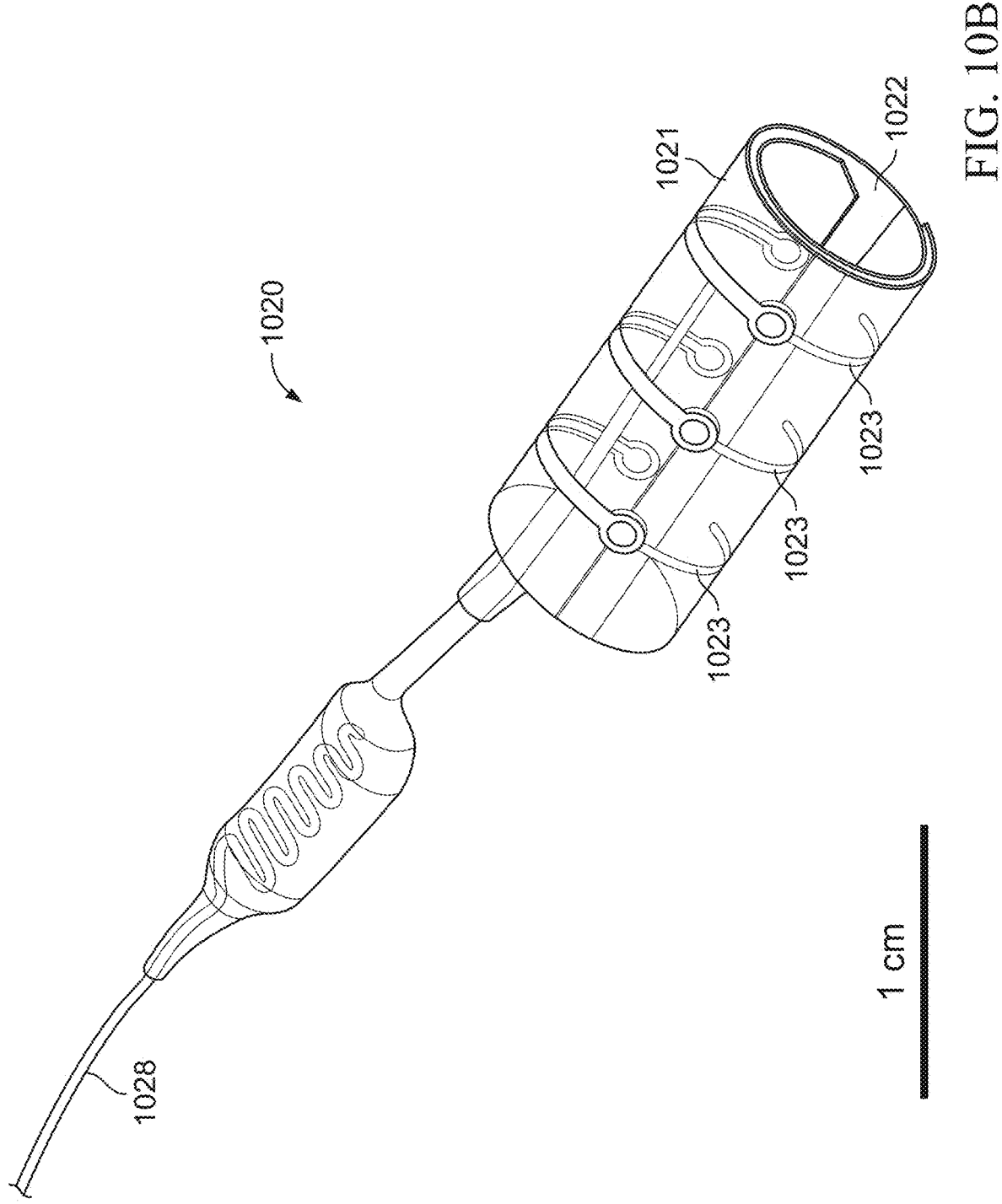
FIG. 10B illustrates another exemplary cuff electrode used for providing electrical stimulation in various embodiments of the present specification.
Figures 10C, 10D:
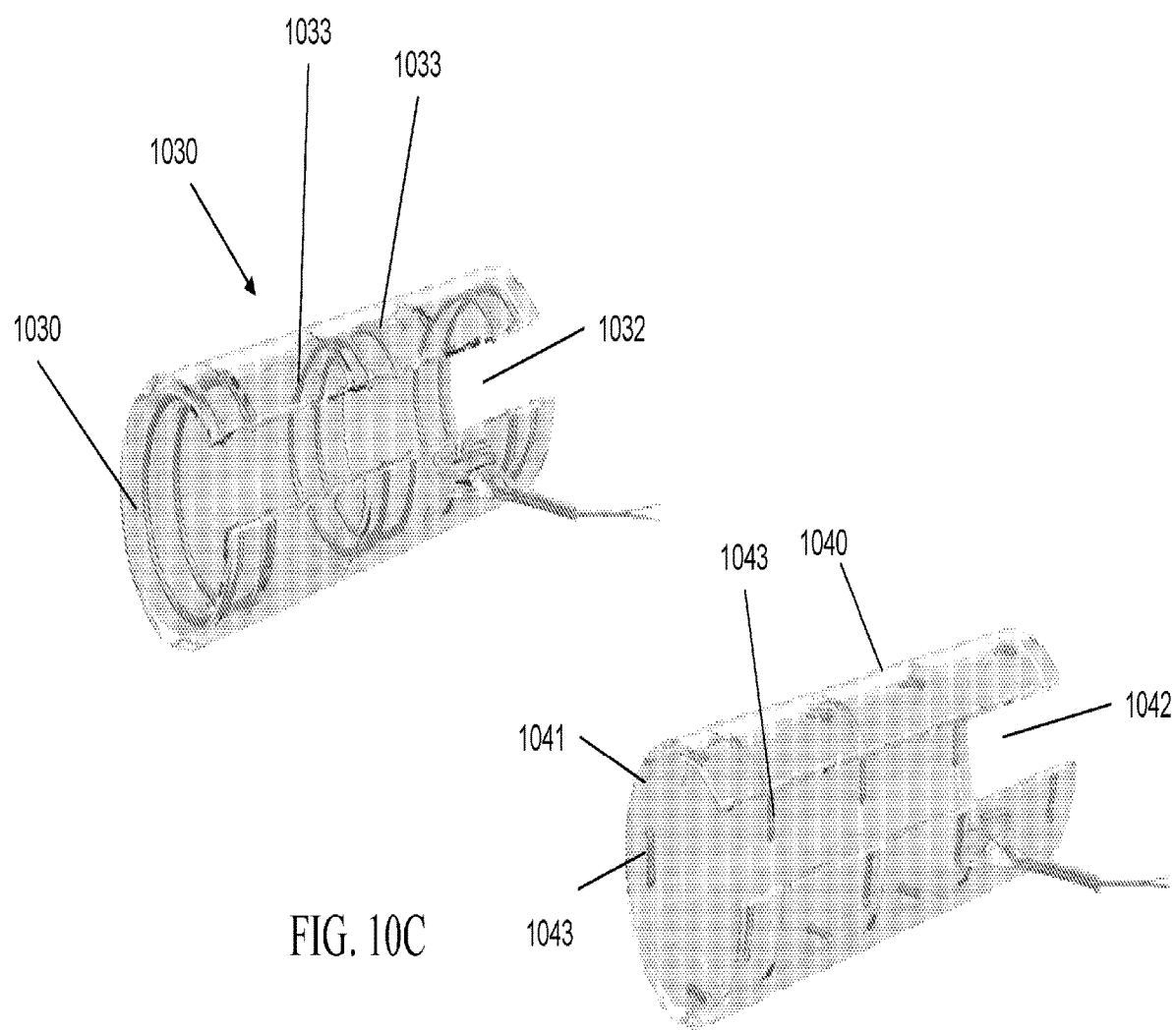
FIG. 10C illustrates another exemplary cuff electrode used for providing electrical stimulation in various embodiments of the present specification.
FIG. 10D illustrates yet another exemplary cuff electrode used for providing electrical stimulation in various embodiments of the present specification.

FIG. 10B illustrates another exemplary cuff electrode design that may be used for providing electrical stimulation in an embodiment of the present specification. In some embodiments, cuff electrode 1020 is made out of polydimethylsiloxane (PDMS) or polyimide, and encircles a blood vessel nearly completely during operation. The cuff electrode 1020 includes a cylindrical portion 1021 configured to wrap about a blood vessel with a cut-out 1022 for placing the cuff electrode 1020 about the vessel. A plurality of electrodes 1023 are positioned in the cylindrical portion 1021 for contact with the blood vessel during operation. In various embodiments, the cuff electrodes 1000, 1020 of FIGS. 10A and 10B respectively, are provided with electrical stimulation energy through connecting with a pulse generator by means of connecting wires 1008, 1028. In other embodiments, the cuff electrodes 1000, 1020 are coupled wirelessly to a pulse generator using a radio frequency (RF) link, an ultrasonic link, a thermal link, a magnetic link, an electromagnetic link, or an optical link. FIG. 10C illustrates another exemplary cuff electrode 1030 known in the art used for providing electrical stimulation in an embodiment of the present specification. Cuff electrode 1030 encircles a blood vessel during operation. The cuff electrode 1030 includes a cylindrical portion 1031 having a cut-out 1032 for placing the cuff electrode 1030 about a blood vessel and electrodes 1033 positioned in pairs along the length of the cylindrical portion 1031. FIG. 10D illustrates yet another exemplary cuff electrode 1040 used for providing electrical stimulation in an embodiment of the present specification. Cuff electrode 1040 encircles a blood vessel during operation. The cuff electrode 1040 includes a cylindrical portion 1041 having a cut-out 1042 for placing the cuff electrode 1040 about a blood vessel and electrodes 1043 positioned in short, separated exposed cylindrical segments distributed longitudinal along the length of the cylindrical portion 1041.

In various embodiments, the cuff electrodes of the present specification are configured to apply a pressure of less than 100 mm Hg on a blood vessel in order to place the electrode in physical contact with the vessel wall without significantly occluding blood flow mechanically.

In another embodiment, a clamp electrode is used to provide the desired stimulation to blood vessels. FIG. 11 illustrates an exemplary clamp electrode for providing electrical simulation to blood vessels. The clamp electrode 1100 comprises an upper plate 1102, an under plate 1104, a clipper 1106, a knob 1108, a connector 1110, a nut 1112, and an electro plate 1114. An additional connector (not shown) is positioned on the underside of under plate 1104. In an embodiment, the clamp electrode 1100 is used to provide electrical stimulation by connecting with a pulse generator 1116 by means of connecting wires 1118. In another embodiment, the clamp electrode 1100 is coupled wirelessly to the pulse generator 1116 using a radio frequency (RF) link, an ultrasonic link, a thermal link, a magnetic link, an electromagnetic link, or an optical link. The clamp electrode 1100 is spring actuated about a pivot point 1103 coupling the upper plate 1102 and under plate 1104. A user presses on the back surfaces of the upper plate 1102 and under plate 1104 to open the clamp electrode 1100 about the pivot point 1103. The front or distal ends 1102d, 1104d of the upper plate 1102 and under plate 1104 are positioned about a blood vessel and the user removes pressure from the back surfaces, allowing the distal ends 1102d, 1104d to close upon the blood vessel by spring actuated movement about the pivot point 1103.

Figure 12:
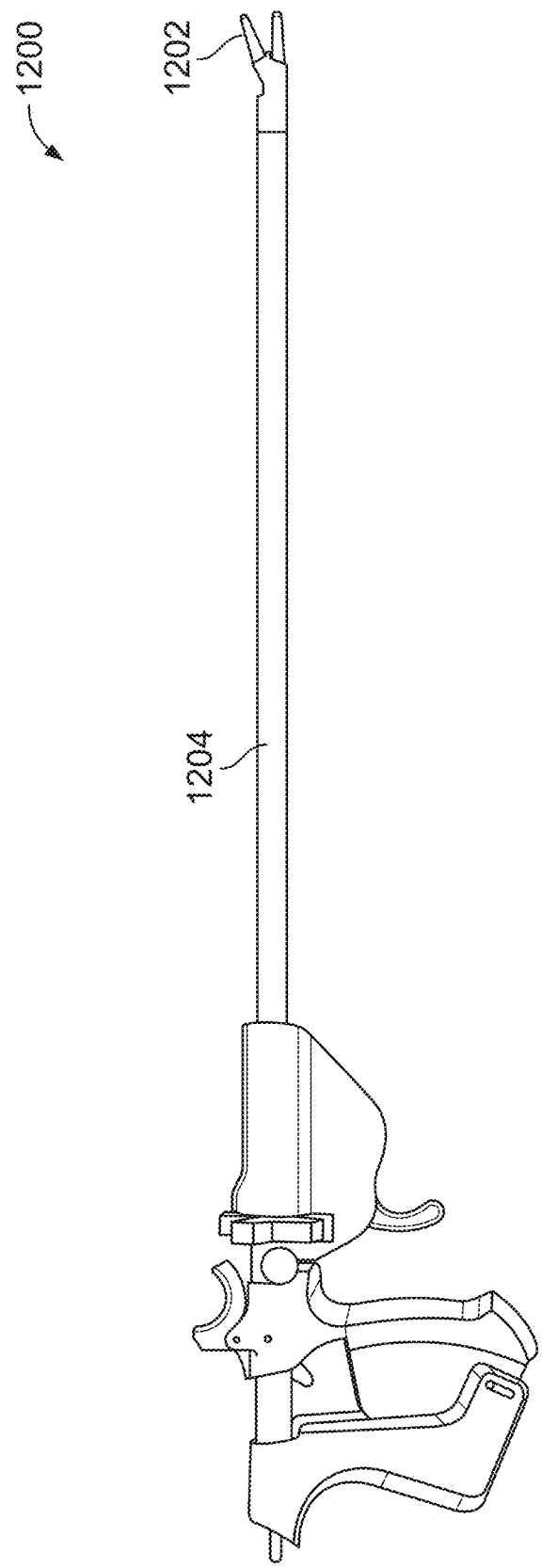
FIG. 12 illustrates laparoscopic forceps used to apply a clamp electrode to a blood vessel, in accordance with an embodiment of the present specification.

FIG. 12 illustrates a laparoscopic forceps 1200 used to place a clamp electrode 1202 on a blood vessel, in accordance with an embodiment of the present specification. In other embodiments, any suitable means for placing a clamp electrode within a blood vessel may be used. Laparoscopic forceps 1200 comprises a shaft portion 1204 and a grasper 1202 used to apply medical devices, such as clamp electrodes, at a desired location within a body. As is known, forceps similar to laparoscopic forceps 1200 may be inserted into a body through a mouth, nose or other body orifices, such as but not limited to an anal orifice or may be inserted through a laparoscopic trocar. In other embodiments, laparoscopic forceps 1200 is used to implant an expandable electrode within a blood vessel.

Figure 13A:
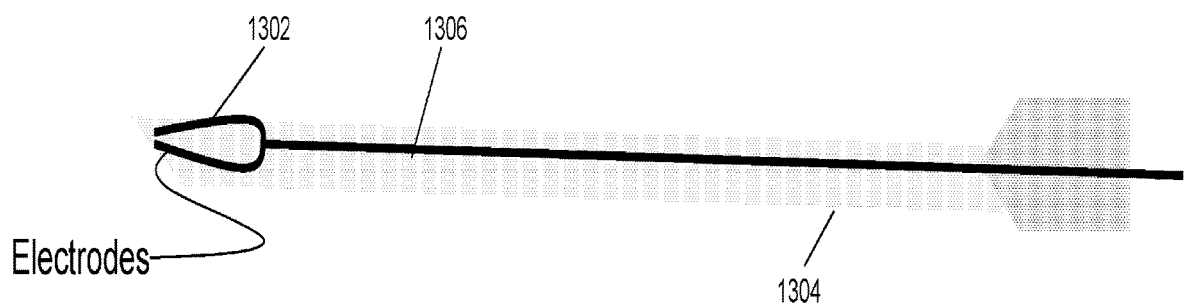
FIG. 13A illustrates an electrode within a catheter of a laparoscope for placement within a blood vessel, in accordance with an embodiment of the present specification.
Figure 13B:
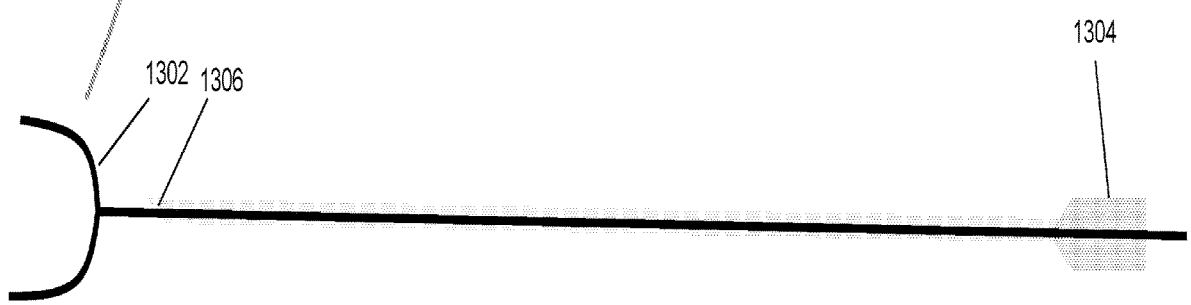
FIG. 13B illustrates an expanded electrode extending out of a catheter of a laparoscope for placement within a blood vessel, in accordance with an embodiment of the present specification.

FIG. 13A illustrates an expandable electrode 1302 with a lead 1306 within a catheter 1304 for placement within a blood vessel. As shown, an expandable electrode 1302 coupled with a lead 1306 is inserted within a catheter 1304, for placing the electrode 1302 within a blood vessel. FIG. 13B illustrates the electrode 1302 of FIG. 13A in an expanded configuration and extending out of the catheter 1304 for placement within a blood vessel. The lead 1306 is also extended out of the catheter 1304 and electrode 1302 has expanded in order to contact walls of a blood vessel. The catheter 1304 is similar to catheters known in the art that are used for accessing vascular systems or placing cardiac pacemaker leads.

Figure 14A:
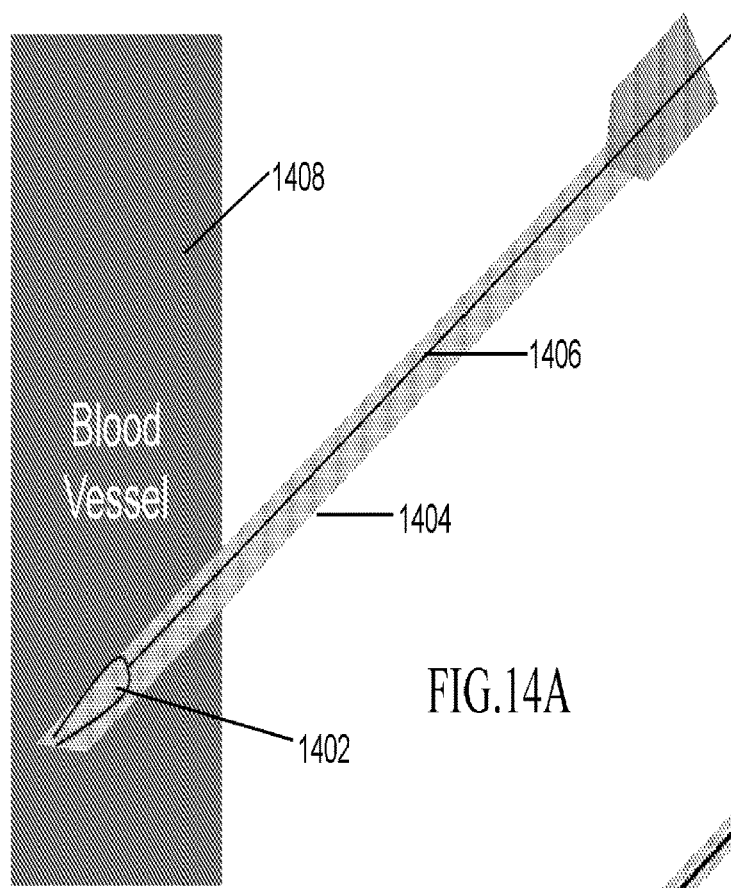
FIG. 14A illustrates a blood vessel punctured by a catheter having a stimulating electrode disposed within, in accordance with an embodiment of the present specification.
Figure 14B:
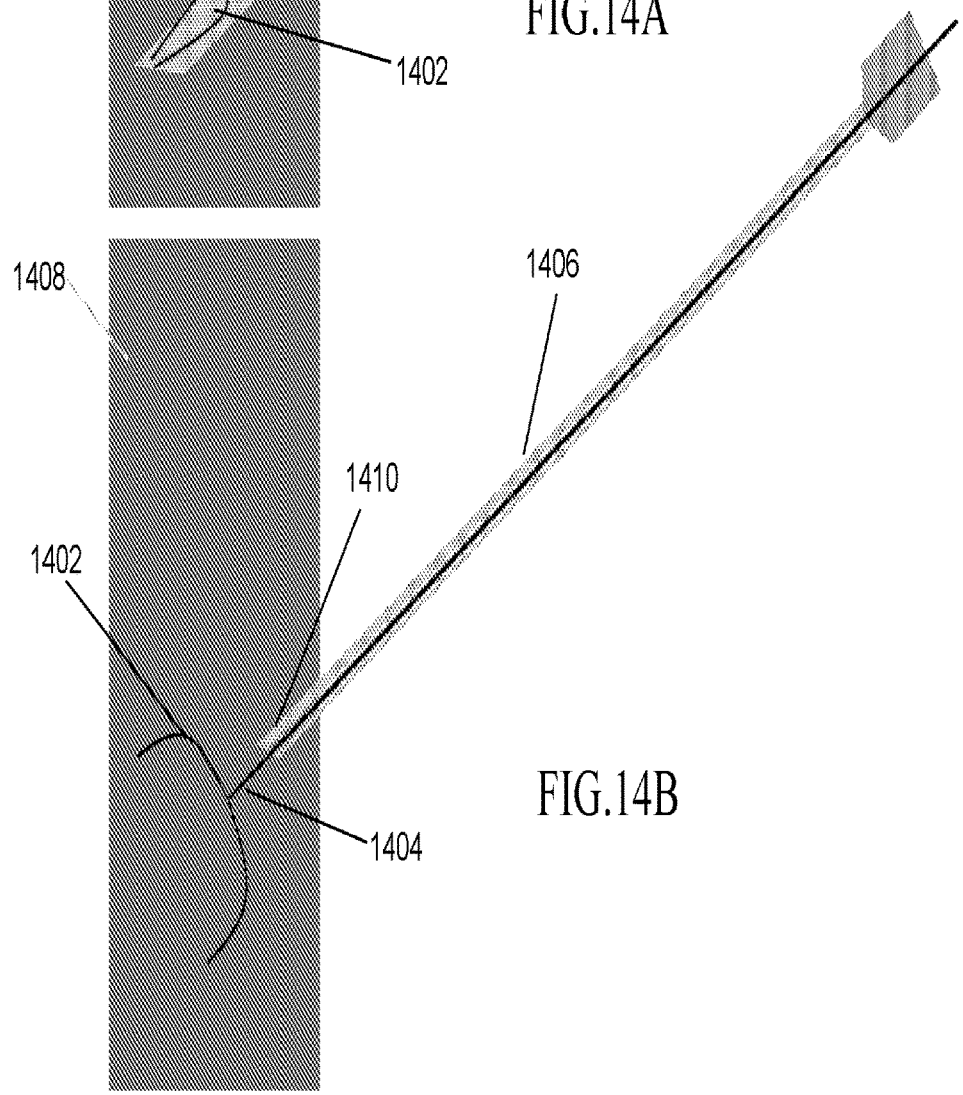
FIG. 14B illustrates the catheter of FIG. 14A with the electrode extended from the catheter.
Figure 14C:
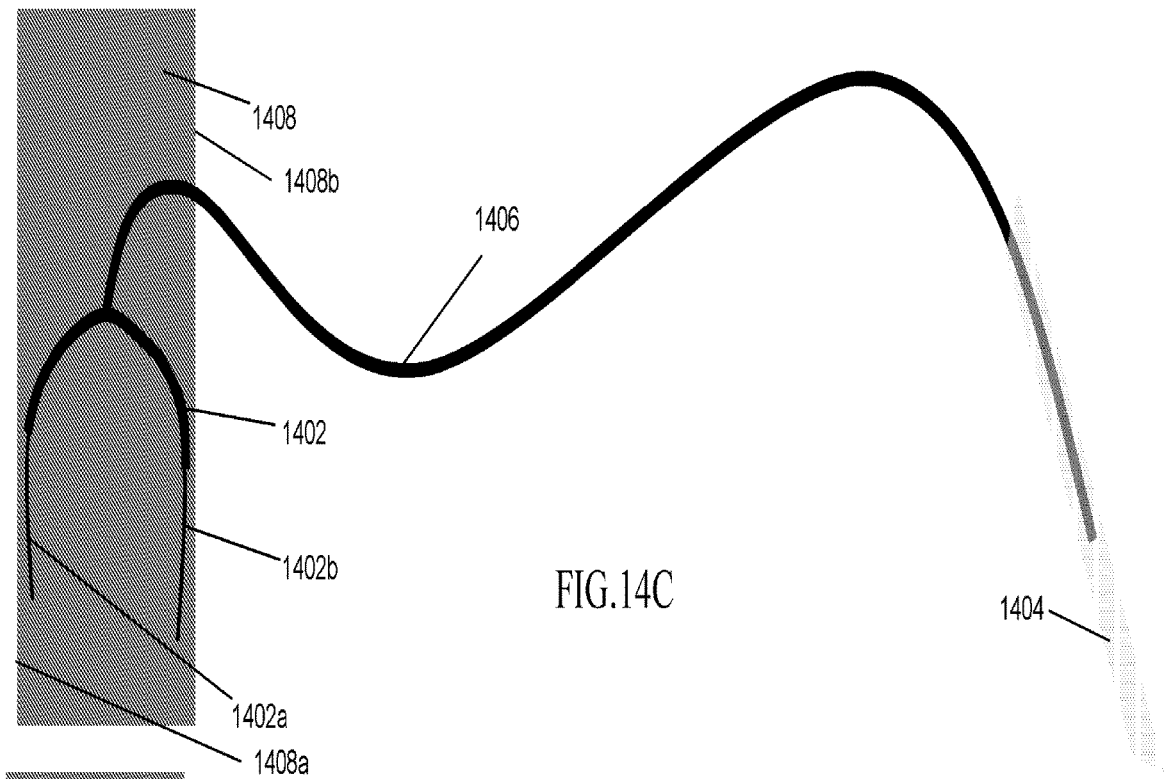
FIG. 14C illustrates the electrode of FIG. 14A in contact with the inner walls of the blood vessel.

FIG. 14A illustrates a catheter 1404 with expandable electrode 1402 positioned within a blood vessel 1408, in accordance with an embodiment of the present specification. As shown, an expandable electrode 1402 coupled with a lead 1406 is inserted within a catheter 1404, for placing the electrode 1402 within a blood vessel 1408. The catheter 1404 is used to puncture the blood vessel 1408 for placing the electrode 1402 within. In various embodiments, blood vessel 1408 may be any artery or vein requiring hemorrhage treatment. FIG. 14B illustrates the electrode 1402 of FIG. 14A extended from catheter 1404 and expanded within blood vessel 1408. As shown in FIG. 14B, electrode 1402 is extended out of a distal end 1410 of catheter 1404 and expanded. FIG. 14C illustrates an electrode 1402 positioned within a blood vessel 1408 in accordance with an embodiment of the present specification. Prongs 1402a and 1402b of electrode 1402 expand to contact walls 1408a, 1408b of the blood vessel 1408 and catheter 1404 is removed from the body cavity containing the blood vessel 1408, leaving lead 1406 for connecting electrode 1402 to a pulse generator.

Figure 14D:
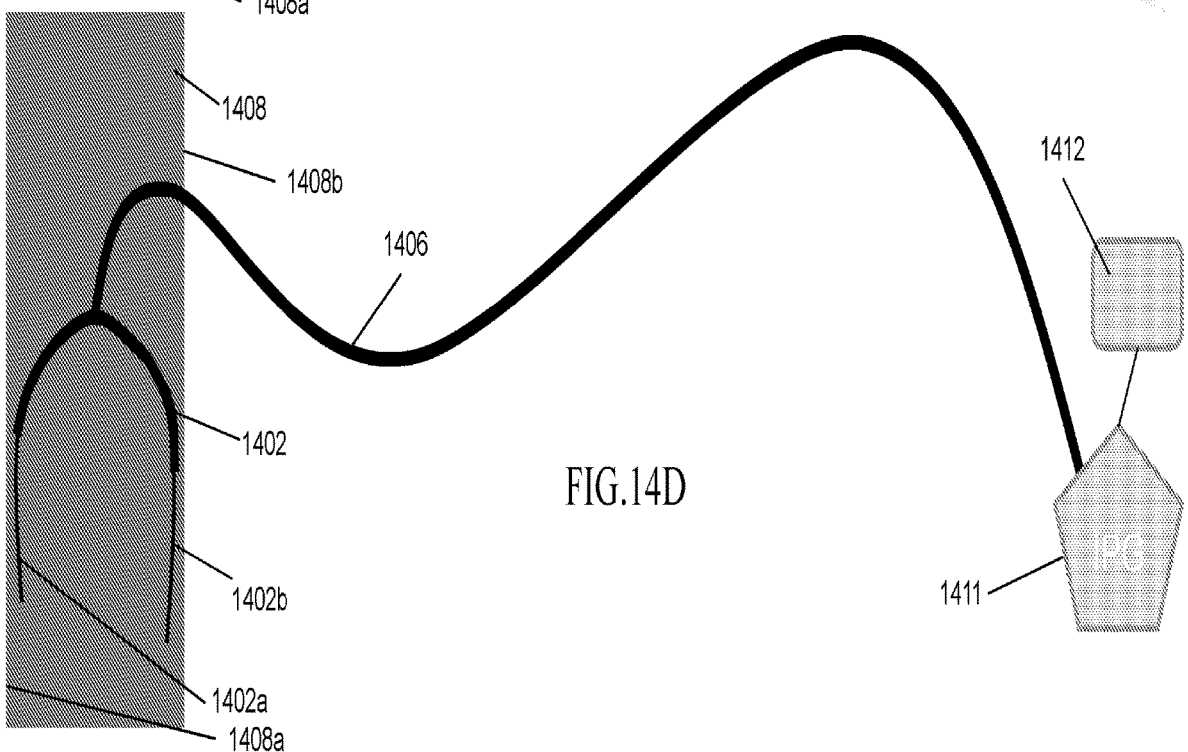
FIG. 14D illustrates the electrode of FIG. 14A connected to an implantable pulse generator by a lead.

FIG. 14D illustrates the electrode 1402 of FIG. 14C connected via lead 1406 to an implantable pulse generator (IPG) 1411. Once the electrode 1402 has been positioned such that prongs 1402a and 1402b of electrode 1402 contact walls 1408a, 1408b of the blood vessel 1408, the lead 1404 is connected to the IPG 1411. Hence, the electrode 1402 may be used to provide electrical stimulation of a desired frequency/amplitude to blood vessel 1408 at desired intervals for desired periods of time. In some embodiments, a microprocessor 1412 is operably connected to the IPG 1411 and controls stimulation parameters generated by the IPG and administered by the electrode 1402.

In an embodiment, electrical stimulation may be used for causing vasoconstriction in a blood vessel (such as an artery) before an arterial graft is performed. FIG. 14E illustrates electrical stimulation being applied to a femoral artery having a blockage within a human leg. As shown, a blockage 1420 is present in the femoral artery 1422 proximal to the popliteal artery 1424 in a human leg 1426. An electrode 1428 is placed within the femoral artery 1422 and is supplied with electrical current of a desired amplitude and frequency for desired intervals of time via an electrical signal generator (ESG) 1430, which is also connected to a grounding pad 1432 applied to the skin proximate the femoral artery 1422. The grounding pad provides a return pathway for electrical current applied through the electrode 1402, eliminating the need for placing a second electrode inside the artery. The electrical stimulation applied to the femoral artery 1422 via the electrode 1428 causes vasoconstriction of the femoral artery 1422 and prevents hemorrhage from the femoral artery 1422 as it is cut into to apply the skin graft. FIG. 14F illustrates an arterial graft 1434 applied after vasoconstriction of the femoral artery 1422 in a human leg 1426 as described with reference to FIG. 14E. Vasoconstriction is achieved via electrical stimulation to the femoral artery 1422 provided by an electrode 1428 connected to an ESG 1430 also having a grounding pad 1432. Once vasoconstriction occurs, an arterial graft 1434 connecting the femoral artery 1422 and popliteal artery 1424 is applied to bypass the blockage 1420 without allowing significant blood loss from the femoral artery 1422. At the conclusion of the surgery, the electrical stimulation is stopped and the blood supply down the vascular pathway is restored.

Figure 14G:
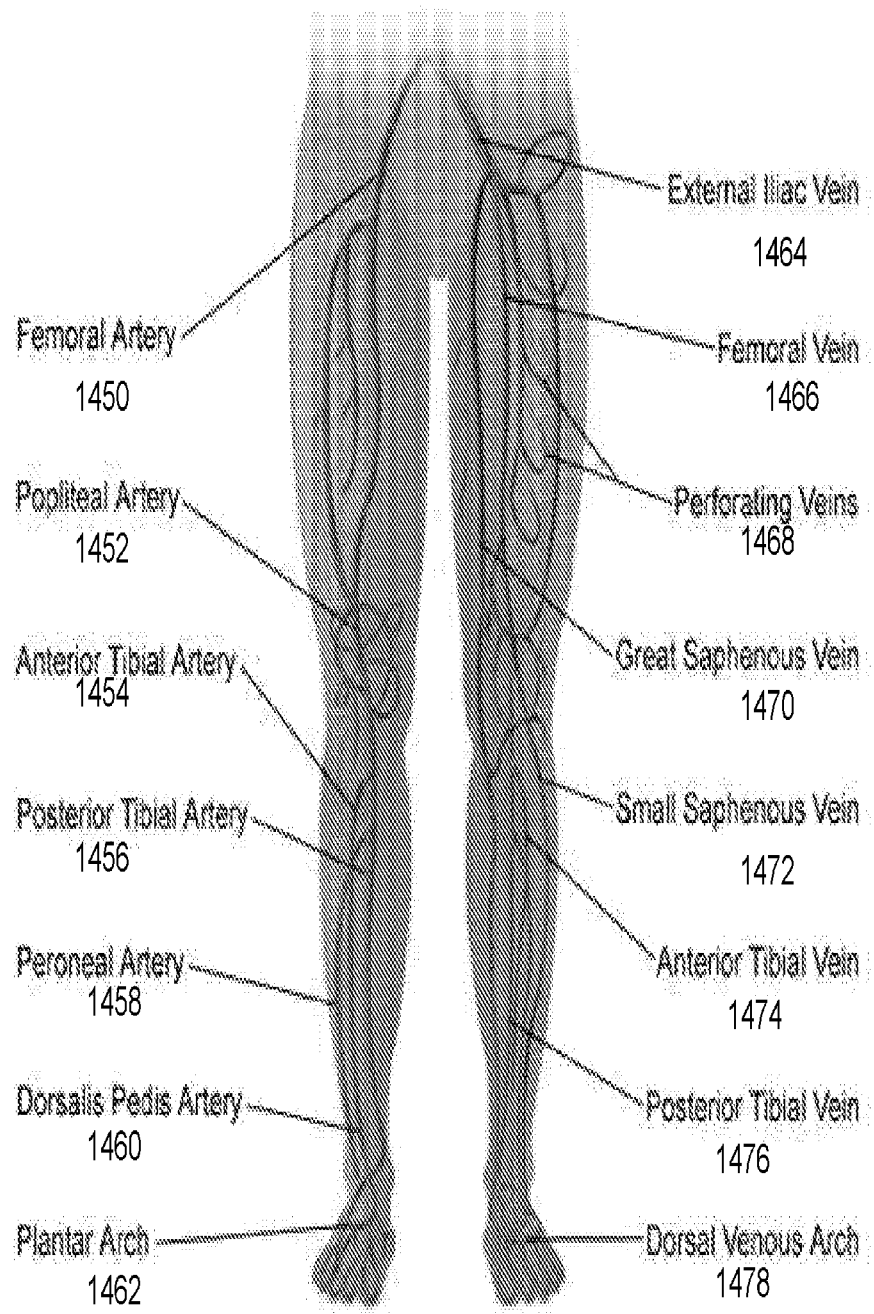
FIG. 14G illustrates the arterial and venous structure of blood vessels within a human leg.

FIG. 14G illustrates the arterial and venous structure of blood vessels within a human leg. As shown, a human leg comprises a femoral artery 1450, a popliteal artery 1452, an anterior tibial artery 1454, a posterior tibial artery 1456, a peroneal artery 1458, a dorsalis pedis artery 1460 and a plantar arch 1462. The human leg also comprises an external iliac vein 1464, a femoral vein 1466, perforating veins 1468, a great saphenous vein 1470, a small saphenous vein 1472, an anterior tibial vein 1474, a posterior tibial vein 1476, and a dorsal venous arch 1478. As described with reference to FIGS. 14A through 14F, electrical stimulation may be applied by placing an electrode proximate (or within) any of the arteries and veins shown in FIG. 14G for causing vasoconstriction and preventing blood loss from the vascular structures.

Figure 14H:
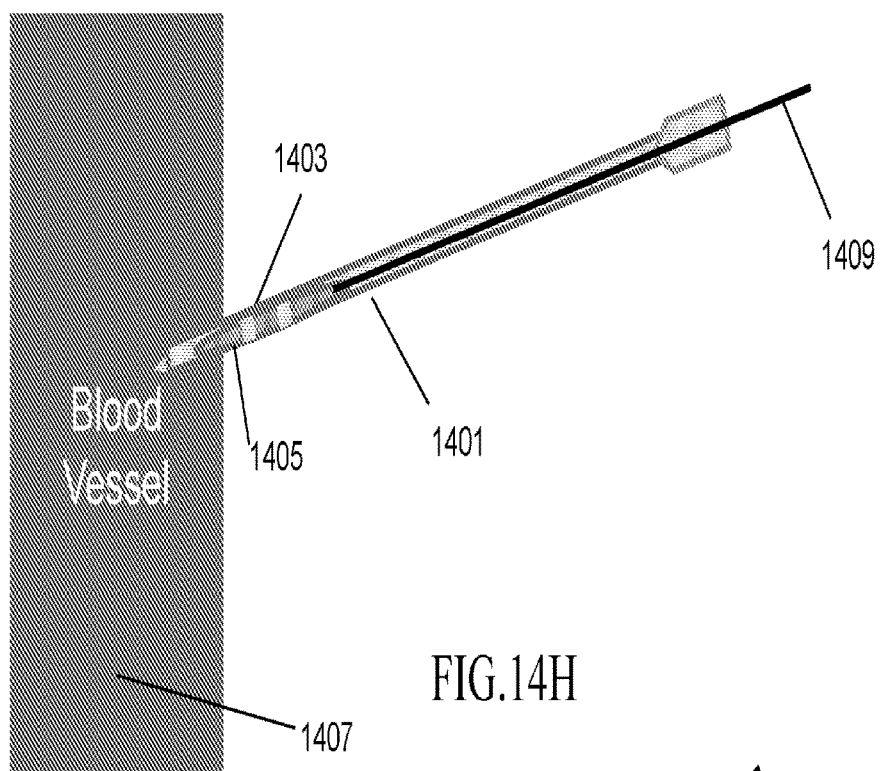
FIG. 14H illustrates a catheter with expandable electrode covering an expandable balloon positioned within a blood vessel, in accordance with an embodiment of the present specification.

In another embodiment electrical stimulation can be applied by placing an electrode proximate (or within) any of the arteries and veins shown in FIG. 14G for causing vasodilation and increasing blood flow in these vascular structures to treat diseases of low blood flow such as peripheral vascular disease. FIG. 14H illustrates a catheter 1401 with expandable electrodes 1403 covering an expandable balloon 1405 positioned within a blood vessel 1407, in accordance with an embodiment of the present specification. As shown, expandable electrodes 1403 coupled with a lead 1409 are inserted via catheter 1401 with a balloon 1405, such that when the balloon 1405 is in a deflated state (as shown in FIG. 14H), the electrodes 1403 are unexpanded, to allow for placement of the electrodes 1403 and balloon 1405 within the blood vessel 1407. The catheter 1401 is used to puncture the blood vessel 1407 for placing the electrodes 1403 and balloon 1405 within the blood vessel 1407. In various embodiments, blood vessel 1407 may be any artery or vein requiring hemorrhage treatment.

Figure 14I:
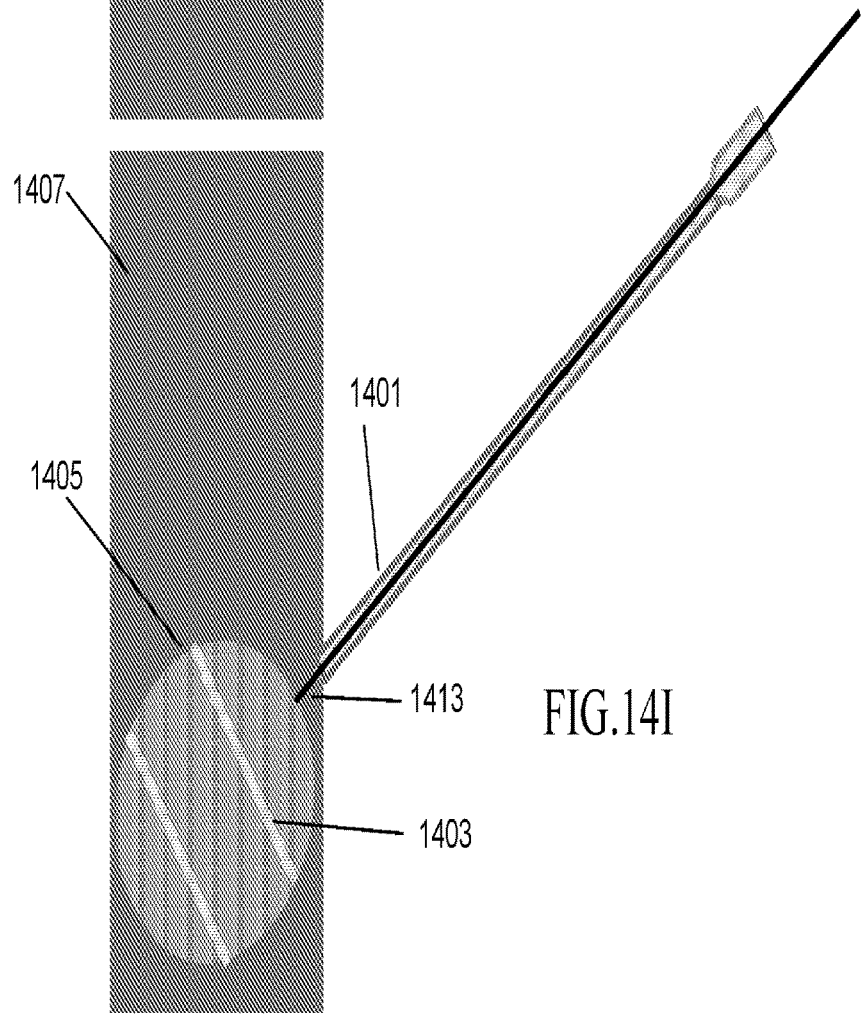
FIG. 14I illustrates the electrode and balloon of FIG. 14H extended from the catheter and expanded due to expansion/inflation of the balloon within the blood vessel.
Figure 14J:
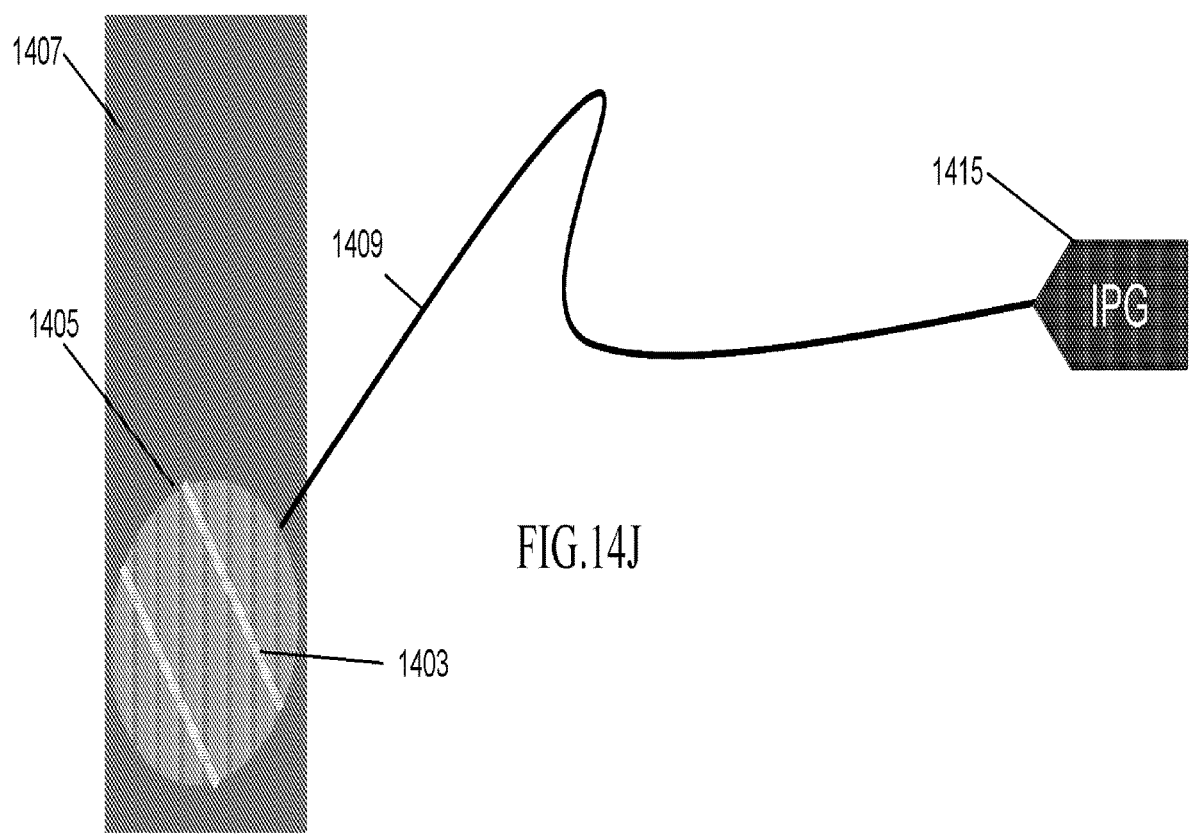
FIG. 14J illustrates the electrode of FIG. 14H connected to an implantable pulse generator by a lead.

FIG. 14I illustrates the electrodes 1403 of FIG. 14H extended from catheter 1401 and expanded due to expansion/inflation of balloon 1405 within blood vessel 1407. As shown in FIG. 14I, balloon 1405 is extended out of a distal end 1413 of catheter 1401 and expanded/inflated, causing the electrodes 1403 to also expand as well about the balloon 1405. FIG. 14J illustrates electrodes 1403, in an expanded state and covering an expanded balloon 1405, positioned within a blood vessel 1407 in accordance with an embodiment of the present specification. The expanded balloon 1405 positions the electrodes 1403 covering the balloon 1405 into contact with the walls of the blood vessel 1407 for delivery of electrical stimulation. Once the balloon 1405 and the electrodes 1403 expand within blood vessel 1407, the catheter 1401 is removed from the body cavity containing the blood vessel 1407, leaving lead 1409 for connecting electrodes 1403 to an implantable pulse generator (IPG) 1415. As can be seen in FIGS. 14I and 14J, expansion of balloon 1405 within the blood vessel 1407 restricts the flow of blood therein, providing a mechanical means of arresting a hemorrhage in the blood vessel 1407. Also, the expanded electrodes 1403 are used to provide electrical stimulation of a desired frequency/amplitude to blood vessel 1407 at desired intervals for desired periods of time, thereby further arresting the blood flow.

Abnormal uterine bleeding (formerly, dysfunctional uterine bleeding, or DUB) is irregular uterine bleeding that occurs in the absence of recognizable pelvic pathology, general medical disease, or pregnancy. It reflects a disruption in the normal cyclic pattern of ovulatory hormonal stimulation to the endometrial lining. The bleeding is unpredictable in many ways. It may be excessively heavy or light and may be prolonged, frequent, or random.

Figure 15A:
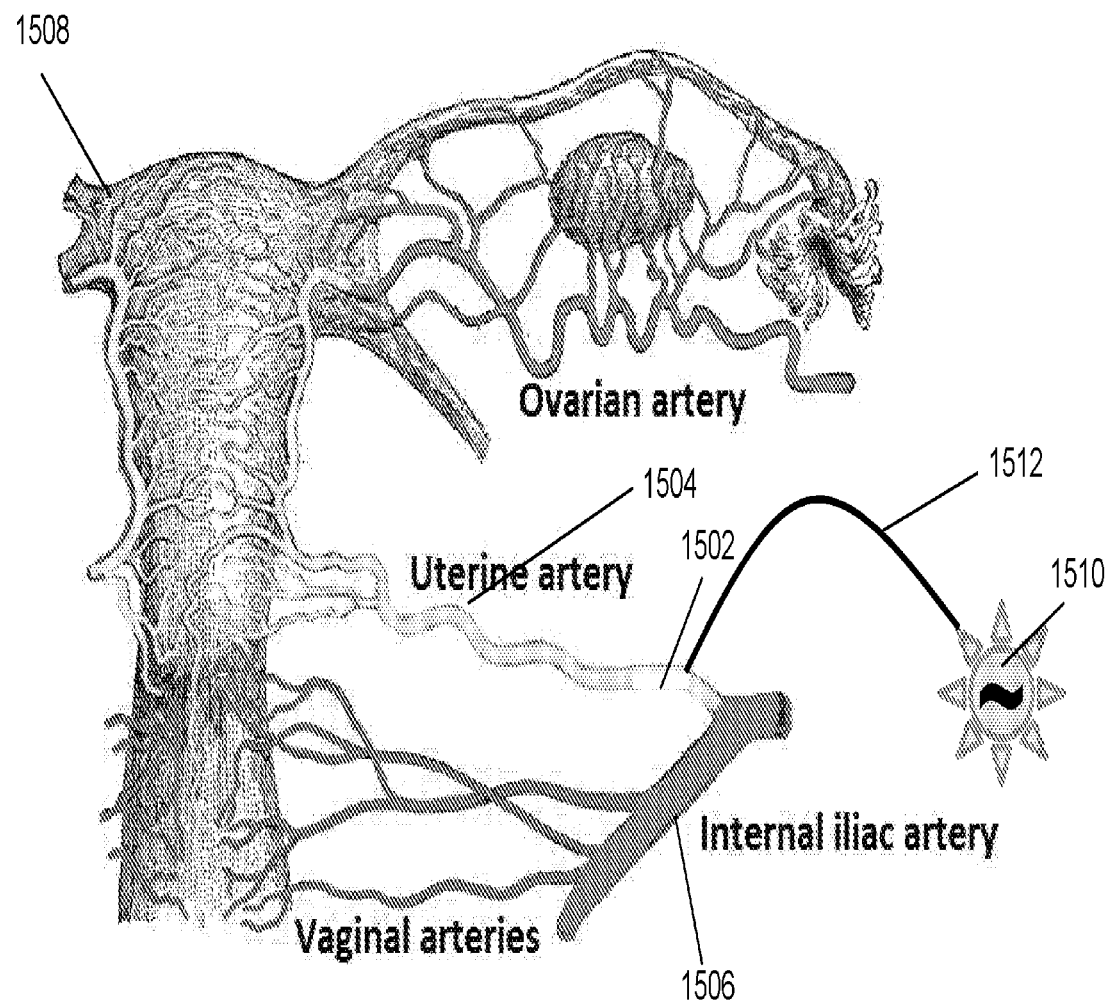
FIG. 15A illustrates application of electrical stimulation to a uterine artery to prevent a uterine bleed, in accordance with an embodiment of the present specification.

The blood supply of the uterus is derived chiefly from the uterine arteries. These arteries arise from the hypogastric artery and swing toward the uterus where these uterine arteries divide into a descending limb and an ascending limb. The descending limb courses downward along the cervix and lateral wall of the vagina. The ascending limb passes upward alongside the uterus and continues below the fallopian tube. Frequent anterior and posterior branches go to the vagina, cervix, and uterus. In an embodiment, the present specification provides a method for treating uterine bleeding by applying electrical stimulation proximate a hypogastric artery, a uterine artery or a branch of a uterine artery or to a nerve supplying a hypogastric artery or a uterine artery to prevent uterine bleeding. In various embodiments, continuous or intermittent stimulation may be applied. In an embodiment, the applied stimulation is controlled by an algorithm that predicts the onset of menstrual bleed and applies the stimulation prior to or during the menstrual bleed to prevent a uterine bleed. FIG. 15A illustrates application of electrical stimulation to a uterine artery 1504 to prevent a uterine bleed. As shown, an electrode 1502 is applied to a uterine artery 1504 which is connected to an internal ileac artery 1506 and supplies blood to a uterus 1508. The electrode 1502 is connected to a pulse generator 1510 by means of connecting leads 1512 to provide electrical stimulation for causing a constriction of the uterine artery 1504. In some embodiments, a patient uses her menstrual cycle chart to trigger the stimulation. In other embodiments, an external device or a software application running on a mobile device, such as a smartphone, predicts the patient's onset of menstrual cycle and triggers the start of stimulation. In still other embodiments, any of a patient's premenstrual symptoms or the first onset of bleeding can be used to trigger stimulation. Since most DUB occurs around the time of a patient's normal menstrual bleeding, such timed stimulation will eliminate the need for stimulation during non-"at-risk" periods.

Figure 15B:
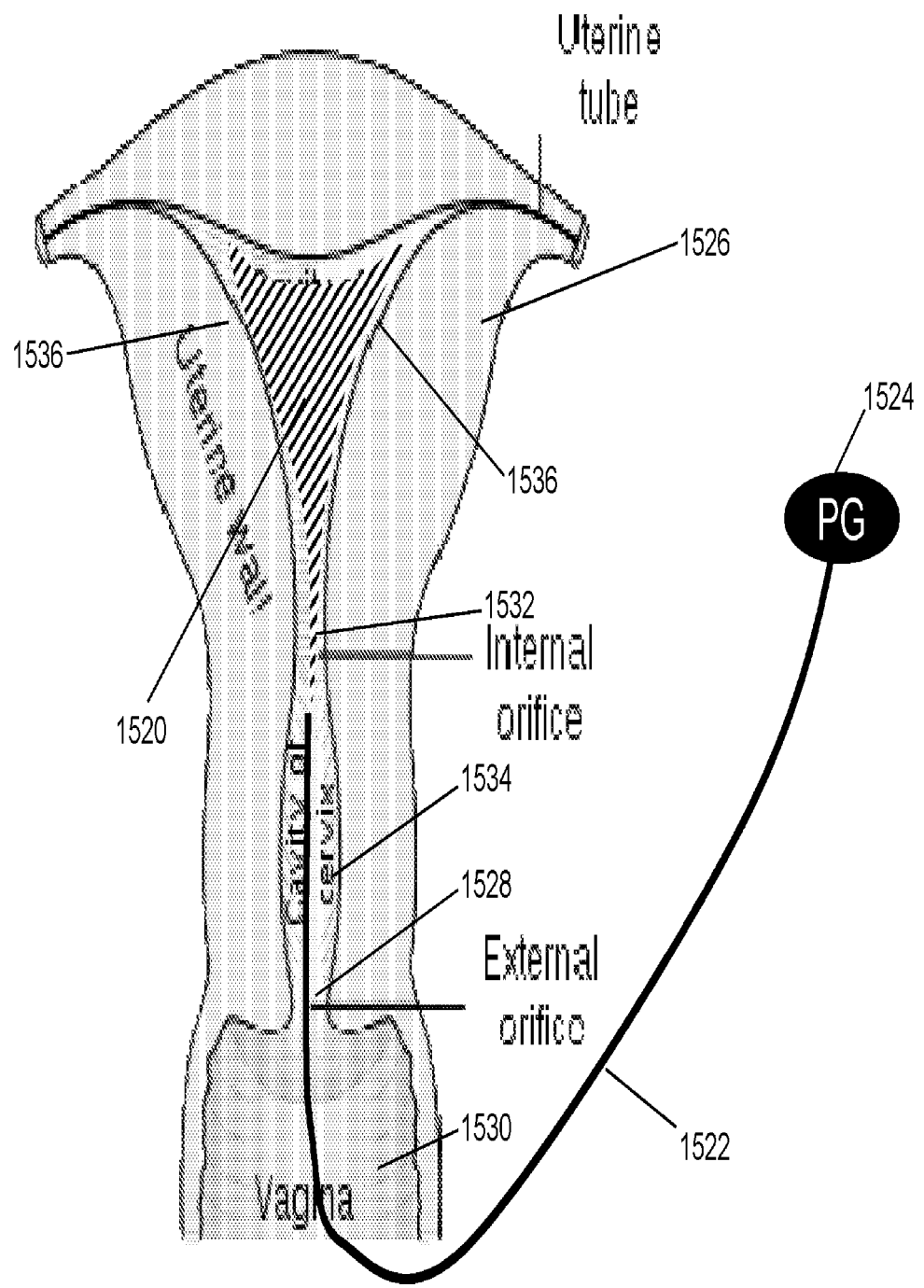
FIG. 15B illustrates application of electrical stimulation to a uterine wall to prevent a uterine bleed, in accordance with an embodiment of the present specification.

In another embodiment, a uterine hemorrhage is controlled by applying electrical stimulation to the uterine wall. FIG. 15B illustrates application of electrical stimulation to a uterine wall 1536 to prevent a uterine bleed. An electrode 1520 coupled with a lead 1522 which, in turn, is coupled with a pulse generator 1524 for providing electrical stimulation, is inserted into a uterus 1526 through a vagina 1530, an external orifice 1528 of a cervical os, a cervix 1534, and an internal orifice 1532 of a cervical os. Within the uterus 1526, electrode 1520 is expanded to be in contact with the uterine walls 1536 to provide electrical stimulation to the walls 1536 for controlling a uterine bleed. The same electrode can then be used at a later time to provide thermal therapy to the uterine cavity without the need for removing the electrode.

Figure 15C:
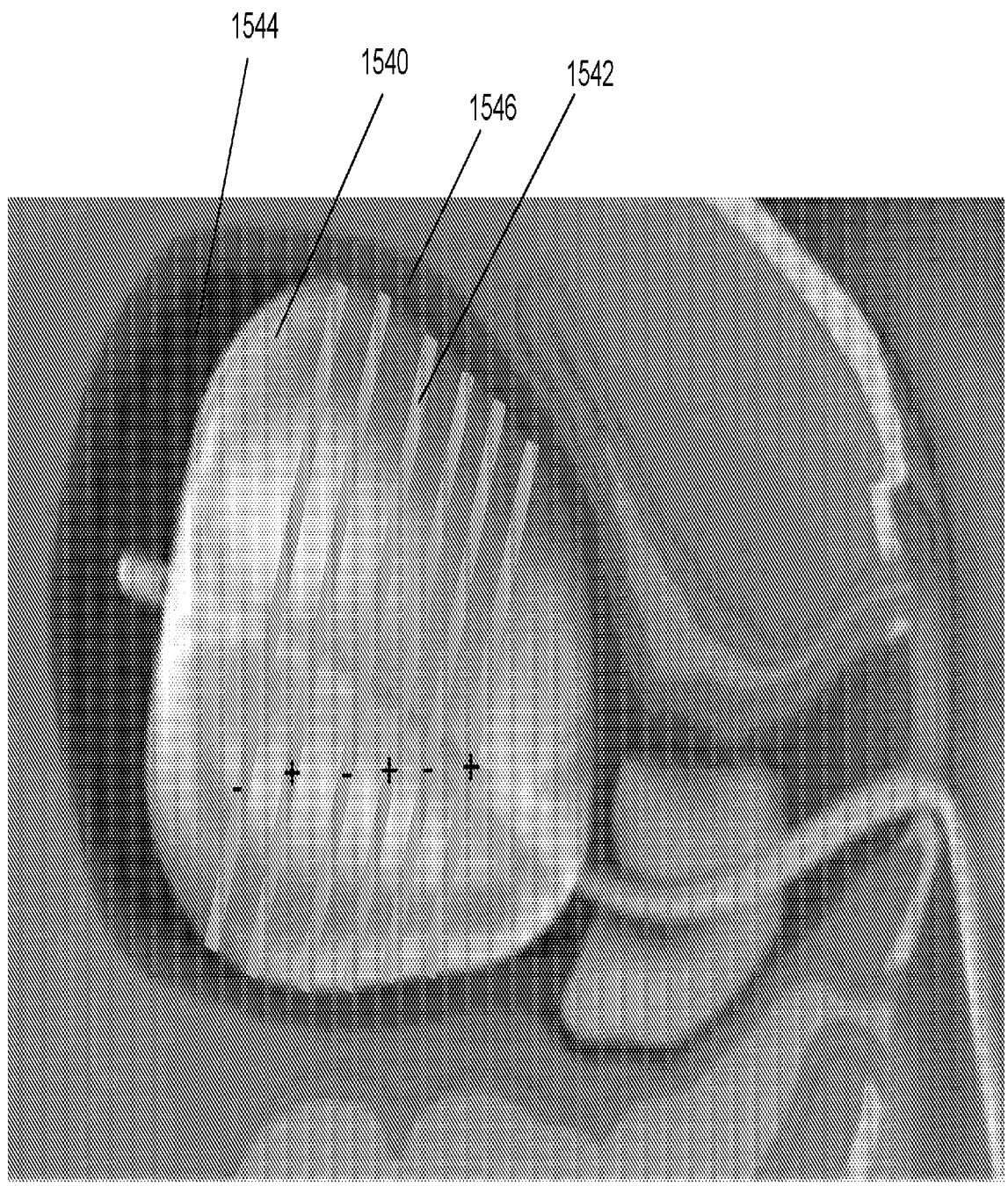
FIG. 15C illustrates application of electrical stimulation to the walls of a uterine cavity to prevent a uterine bleed, in accordance with another embodiment of the present specification.

In an embodiment, an inflatable balloon catheter having surface electrodes, as is known in the art, is inserted within a uterine cavity and then inflated so that the electrodes are in contact with the uterine walls. Electric stimulation is applied to the uterine walls via the surface electrodes in order to arrest a uterine bleed. FIG. 15C illustrates application of electrical stimulation to walls 1546 of a uterine cavity using a balloon catheter 1540 to prevent a uterine bleed. As shown, a balloon catheter 1540 having a plurality of surface electrodes 1542 is placed in a uterine cavity 1544 and the balloon 1540 is expanded so that the electrodes 1542 are in contact with the uterine wall 1546. In an embodiment, a non-thermal, electrical current is applied to the electrodes 1542 to cause vasoconstriction without coagulation resulting in hemostasis or a decrease in blood flow. Additional coagulation current can be applied through the same electrodes 1542 to further aid with hemostasis. In some embodiments, the balloon is expanded to a pressure where it causes a tamponade of the uterine bleeding in addition to electrical vasoconstriction and hemostasis. The same electrode can then be used at a later time to provide thermal therapy to the uterine cavity without the need for removing the electrode.

Figure 15D:
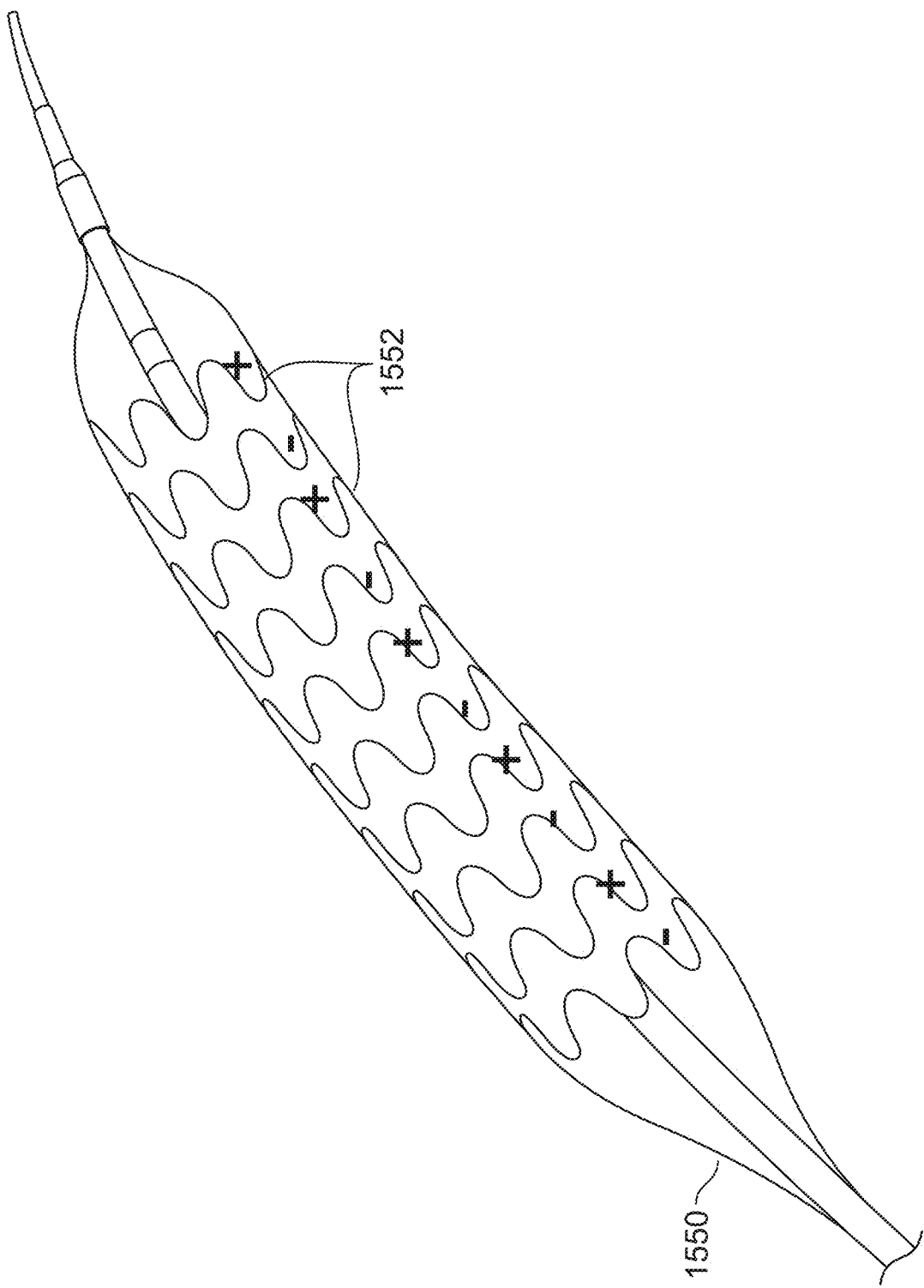
FIG. 15D illustrates an expandable balloon catheter with expandable electrodes used for controlling a hemorrhage, in accordance with an embodiment of the present specification.

FIG. 15D illustrates an expandable balloon catheter 1550 with expandable electrodes 1552 used for controlling a hemorrhage, in accordance with an embodiment of the present specification. The balloon 1550 comprises bipolar electrodes 1552 which expand when the balloon 1550 expands to contact a body surface. The balloon 1550 is shown in an unexpanded state in FIG. 15D. Once inserted within a body cavity by any suitable means, such as via an endoscope, the balloon 1550 is expanded to fill the cavity, thereby bringing the electrodes 1552 into physical contact with walls of the body cavity, for example, as shown in FIG. 15C. In various embodiments, the balloon is composed of latex, silicone, flexible polyvinyl chloride (PVC), PTFE, ePTFE, polyester (PET) polyethylene terephthalate, cross-linked polyethylene, nylon or PET or another material known in the field. In various embodiments, the electrodes are composed of gold, platinum, iridium, titanium, stainless steel, cobalt based alloys or a combination thereof or any other electrode material known in the field. In various embodiments, the volume of the balloon is between 1 cc and 500 cc.

In an embodiment, the present specification provides a method of treating a tumor by modulating blood flow to the tumor. A condition known as ischemia reperfusion leads to injury in normal organs, especially those with high metabolic rates. It is reasonable to assume that ischemia reperfusion can also lead to injury to cancerous cells which have a very high metabolic rate. However it is hard to produce reversible ischemia followed by reperfusion using standard embolization therapies which are usually irreversible. Hence, it is desirable to reversibly control blood flow to a tumor causing ischemia followed by reperfusion to produce tumor cell injury and cell death. Also, the higher metabolic rate of the cancerous cells compared to surrounding normal tissue may allow for selective damage to the cancerous cells with less damage to the surrounding noncancerous cells supplied by the same blood vessel. Intermittent mechanical clamping has shown to protect a tumor against accelerated tumor growth. Intermittent mechanical clamping has also led to protection against hepatic injury resulting from ischemia or reperfusion. However, the process of intermittent mechanical clamping is cumbersome and time consuming during a surgery. Electrical stimulation of a vascular structure by reliably and reversibly controlling the blood flow to an organ can achieve reversible electrically mediated clamping of the blood vessel. In an embodiment, the present specification provides a method of regulating blood flow to an organ during an oncological surgery by applying an electrical stimulus to a blood vessel of an organ to cause a change in the tone of the blood vessel. In an embodiment, the present specification also provides a method of regulating blood flow to the liver during a hepatobiliary surgery by applying an electrical stimulus to a hepatic artery to cause a change in the tone of the hepatic artery.

Figure 16:
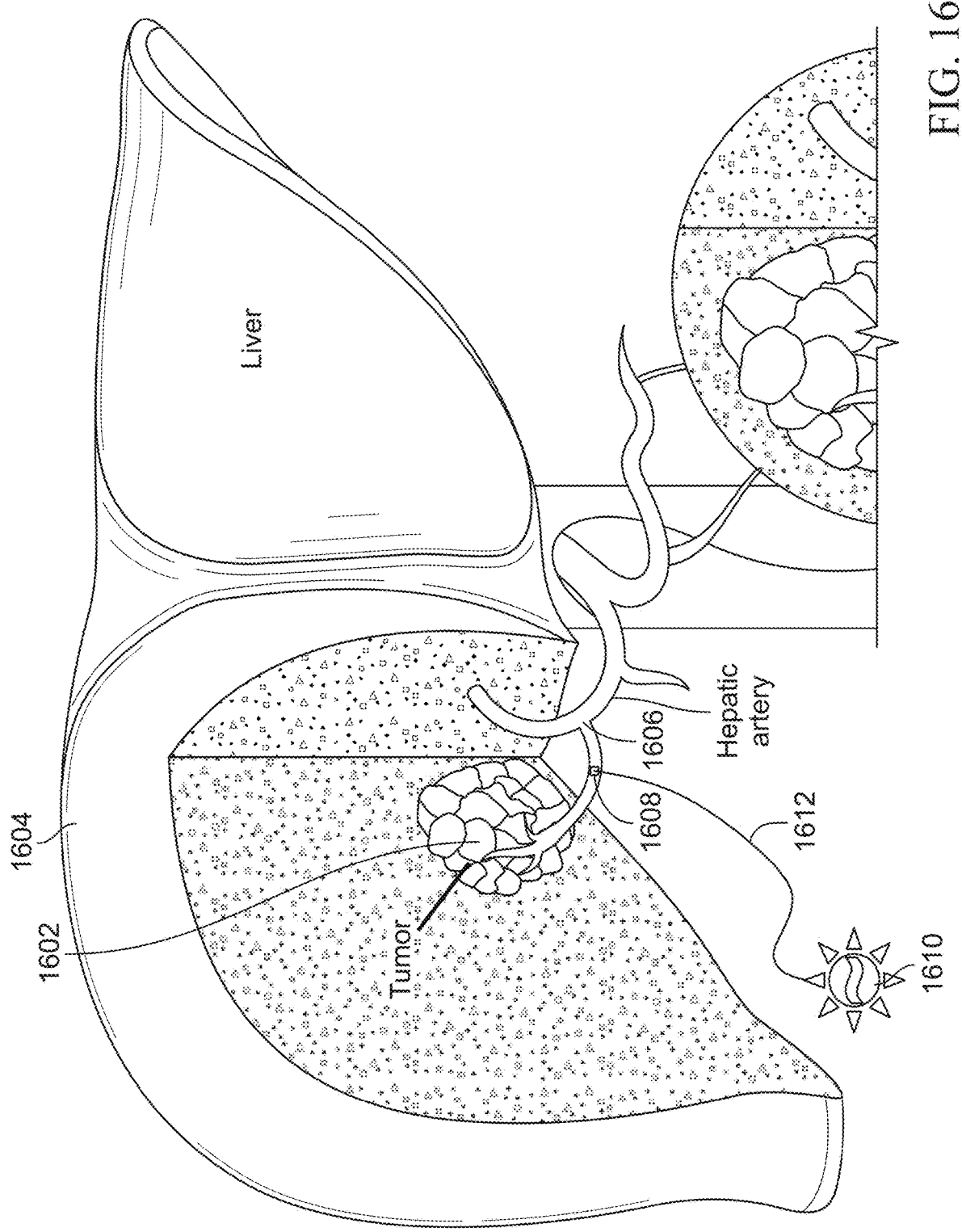
FIG. 16 illustrates a method of treating a tumor by applying electrical stimulation, in accordance with an embodiment of the present specification.

The blood flow may be modulated or changed by applying electrical stimulation to a blood vessel supplying blood to the tumor or to a nerve innervating the blood vessel supplying blood to the tumor. In case of cancerous cells, the blood supply can be changed for variable durations followed by allowing for normal blood flow resulting in reperfusion of the tumor and injury to the cancerous cells. The duration is selected by defining the duration of ischemia or altered blood flow required to cause damage to cancerous cells and the duration of ischemia or altered blood flow required to cause damage to noncancerous cells and stimulating the blood vessel for a duration lying within the two determined durations to selectively damage the cancerous cells. FIG. 16 illustrates treating a tumor in a liver by applying electrical stimulation, in accordance with an embodiment of the present specification. A tumor 1602 in a liver 1604 may be treated by applying electrical stimulation to a hepatic artery 1606 that supplies blood to the liver 1604. An electrode 1608 is connected to a pulse generator 1610 via a connecting lead 1612 in order to provide the electrical stimulation. In various embodiments, the electrode is placed inside the hepatic artery in electrical contact with the intima or on the hepatic artery in electrical contact with the adventitia or one of the branches of hepatic artery or a nerve supplying the hepatic artery. In various embodiments, the electrode is placed using standard laparoscopic, radiological, endoscopic or stereotactic techniques. In various embodiments, electrical stimulation therapy is combined with any one or combination of chemotherapy, radiation therapy, arterial embolization, chemo-embolization or radio-embolization. The concomitant use of electrical stimulation with embolization may help alter the size of the embolization particles needed for improved efficacy.

Figures 17A, 17B:
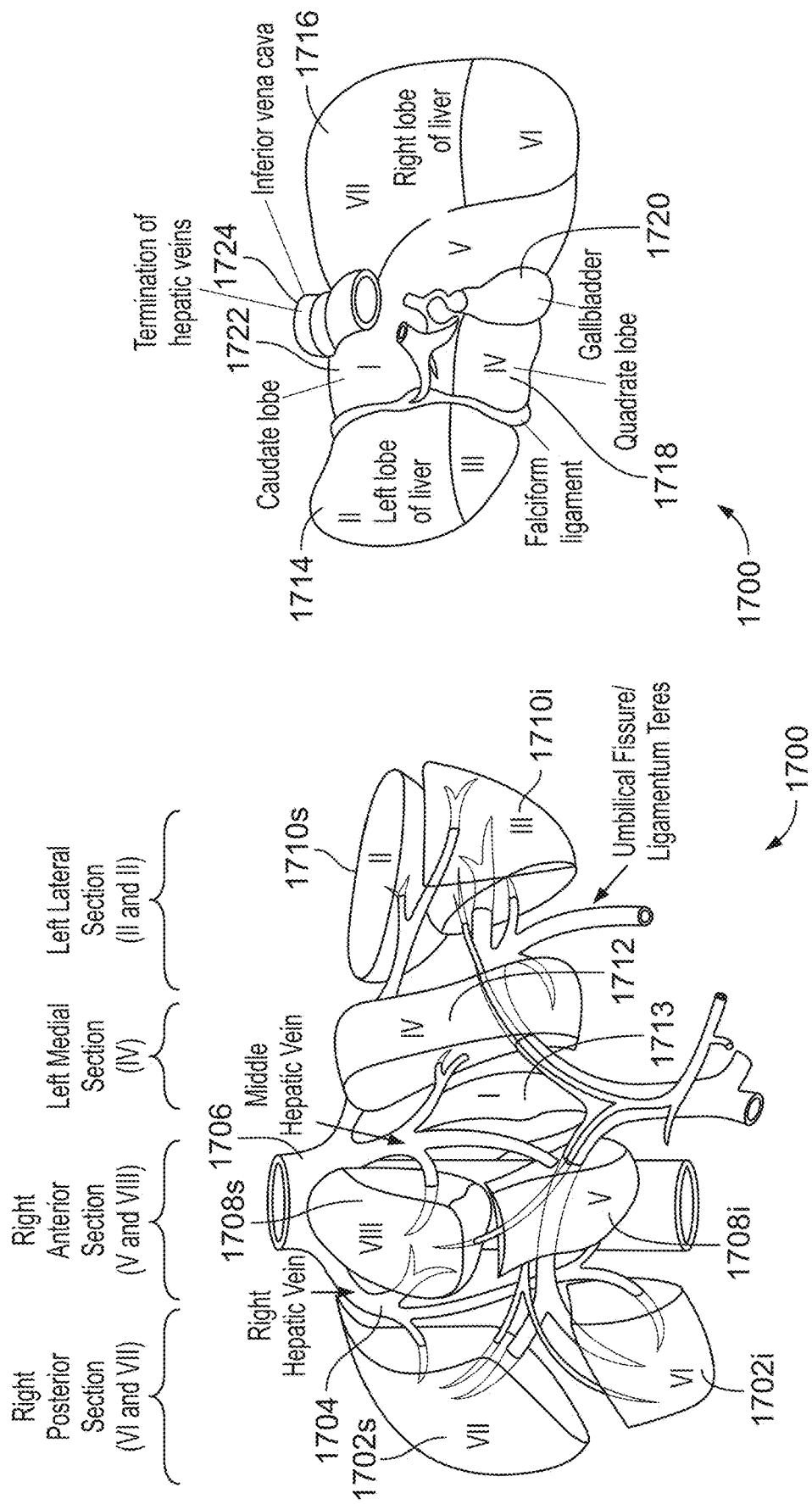
FIG. 17A illustrates the segments of a human liver.
FIG. 17B illustrates the lobes of a human liver.

For purposes of study and providing medical treatment, the liver is segmented into a plurality of segments. FIG. 17A illustrates the segments of a human liver. The liver 1700 comprises right anterior superior and inferior sections 1708s, 1708i lying between a right hepatic vein 1704 and a middle hepatic vein 1706 and corresponding right posterior superior and inferior sections 1702s, 1702i. Further, the liver 1700 is segmented into left lateral superior and inferior sections 1710s, 1710i, medial section 1712, and caudate process 1713. The liver may also be treated by defining various sections or lobes. FIG. 17B illustrates the lobes of a human liver. Liver 1700 comprises a left lobe 1714 and a right lobe 1716, a quadrate lobe 1718 proximate a gallbladder 1720, and a caudate lobe 1722 proximate an inferior vena cava 1724.

Figure 17C:
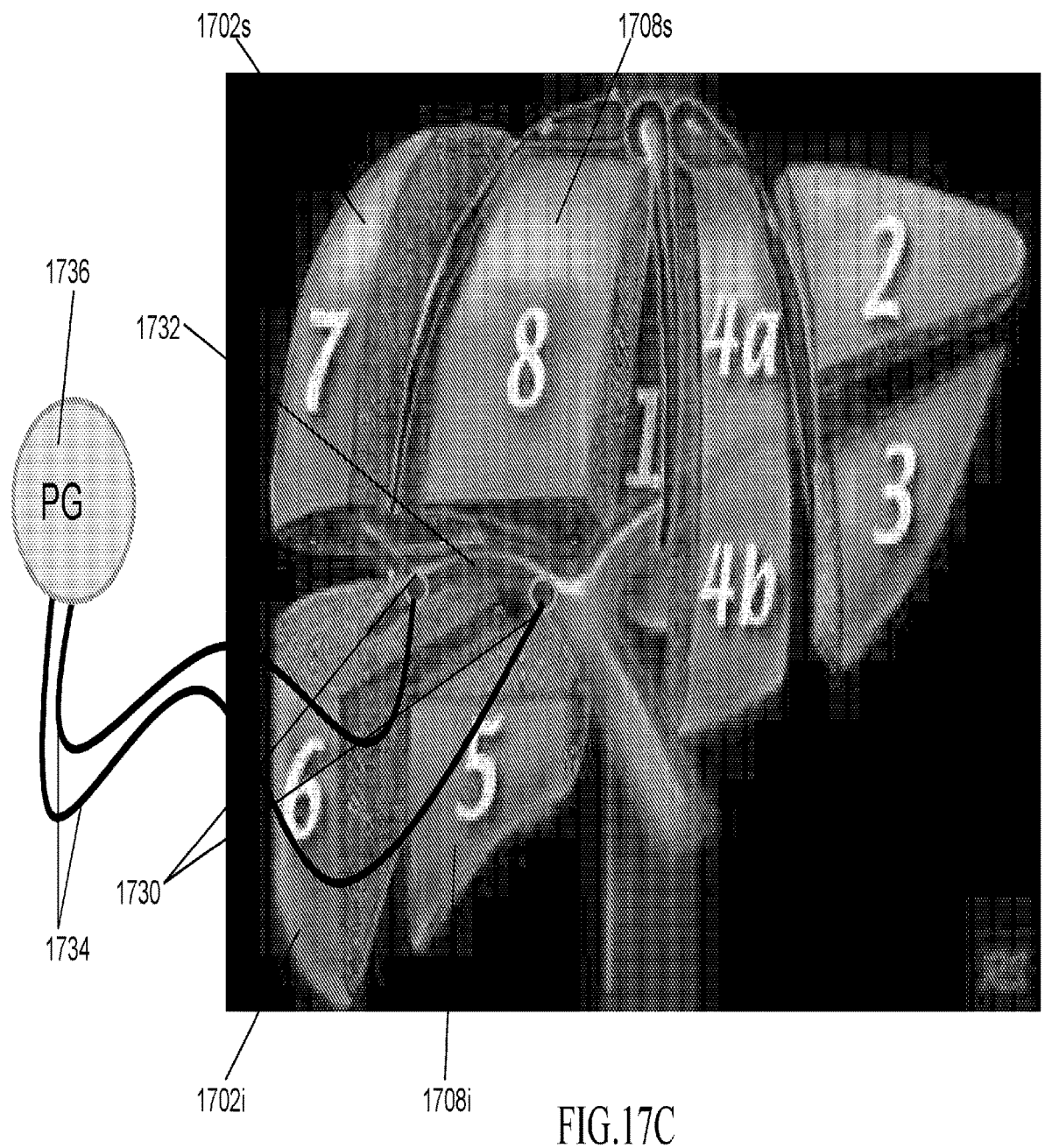
FIG. 17C illustrates controlling liver hemorrhage by application of electrical stimulation in accordance with an embodiment of the present specification.

In an embodiment, a hemorrhage in a liver segment may be controlled by applying electrical stimulation to one or more blood vessels supplying blood to the segment, thereby stopping the bleeding. FIG. 17C illustrates controlling liver hemorrhage by application of electrical stimulation in accordance with an embodiment of the present specification. As shown in FIG. 17C, a pair of electrodes 1730 are placed proximate to blood vessels 1732 supplying blood to segments 1702s, 1702i, 1708s and 1708i. The electrodes 1730 are placed proximate bleeding segments and blood vessels 1732 supplying them and are coupled via leads 1734 to a pulse generator 1736 for applying electrical stimulation to the blood vessels 1734, thereby controlling the bleeding in the liver segments.

Figure 17D:
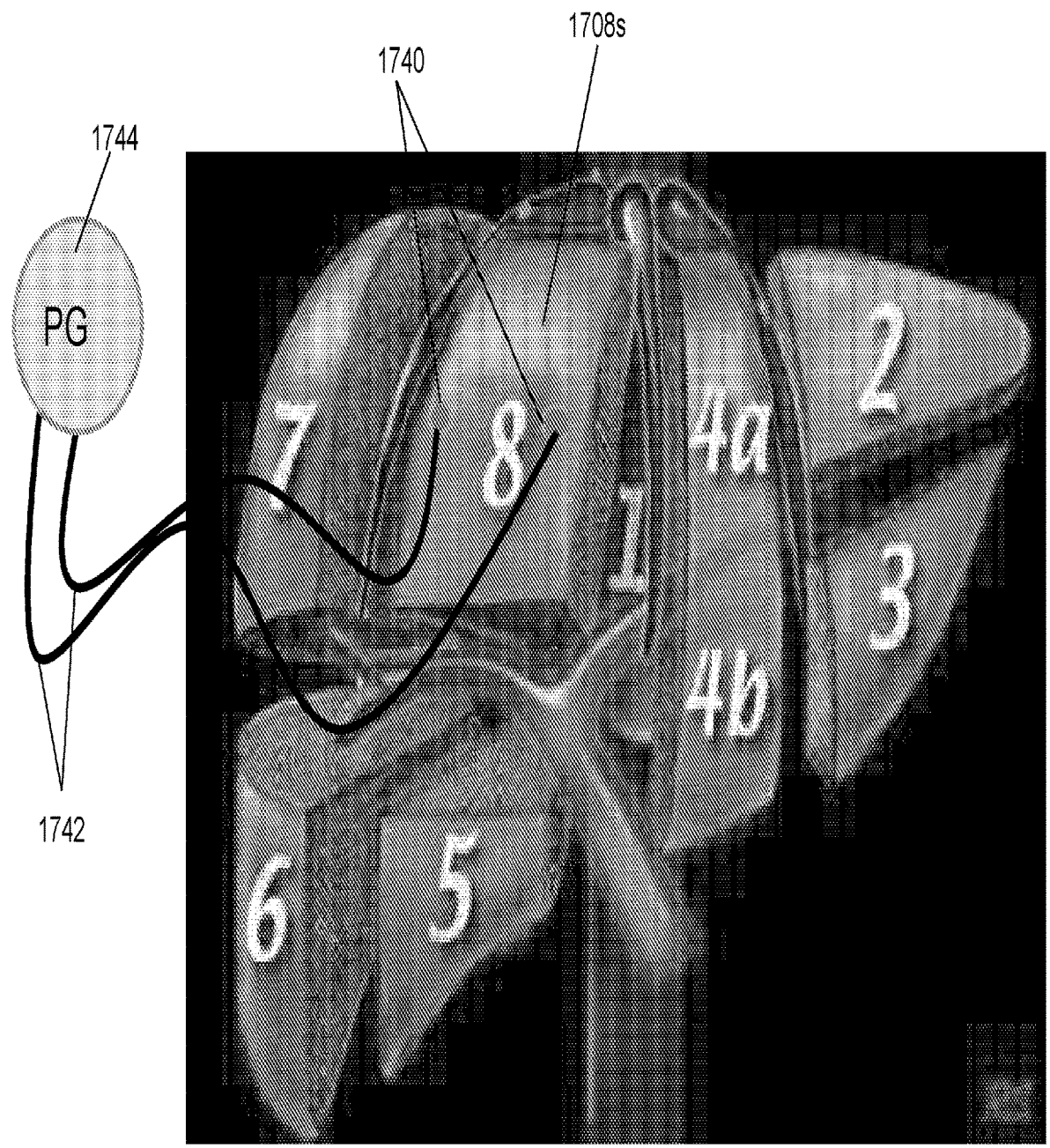
FIG. 17D illustrates controlling liver hemorrhage by application of electrical stimulation, in accordance with another embodiment of the present specification.

In another embodiment a hemorrhage in a liver segment may also be controlled by placing one or more electrodes on the surface or into the parenchyma of one or more segments of the liver and applying an electrical stimulation to the blood vessel in the liver parenchyma to stop bleeding. FIG. 17D illustrates controlling liver hemorrhage by application of electrical stimulation in accordance with another embodiment of the present specification. As shown in FIG. 17D, a pair of electrodes 1740 are placed on the surface or in the parenchyma of liver segment 1708s, which is actively bleeding, for applying electrical stimulation to generate an electrical field, which in turn stimulates the blood vessels within the liver segment 1708s, via leads 1742 connected to a pulse generator 1744, thereby controlling the bleeding.

Figure 18A:
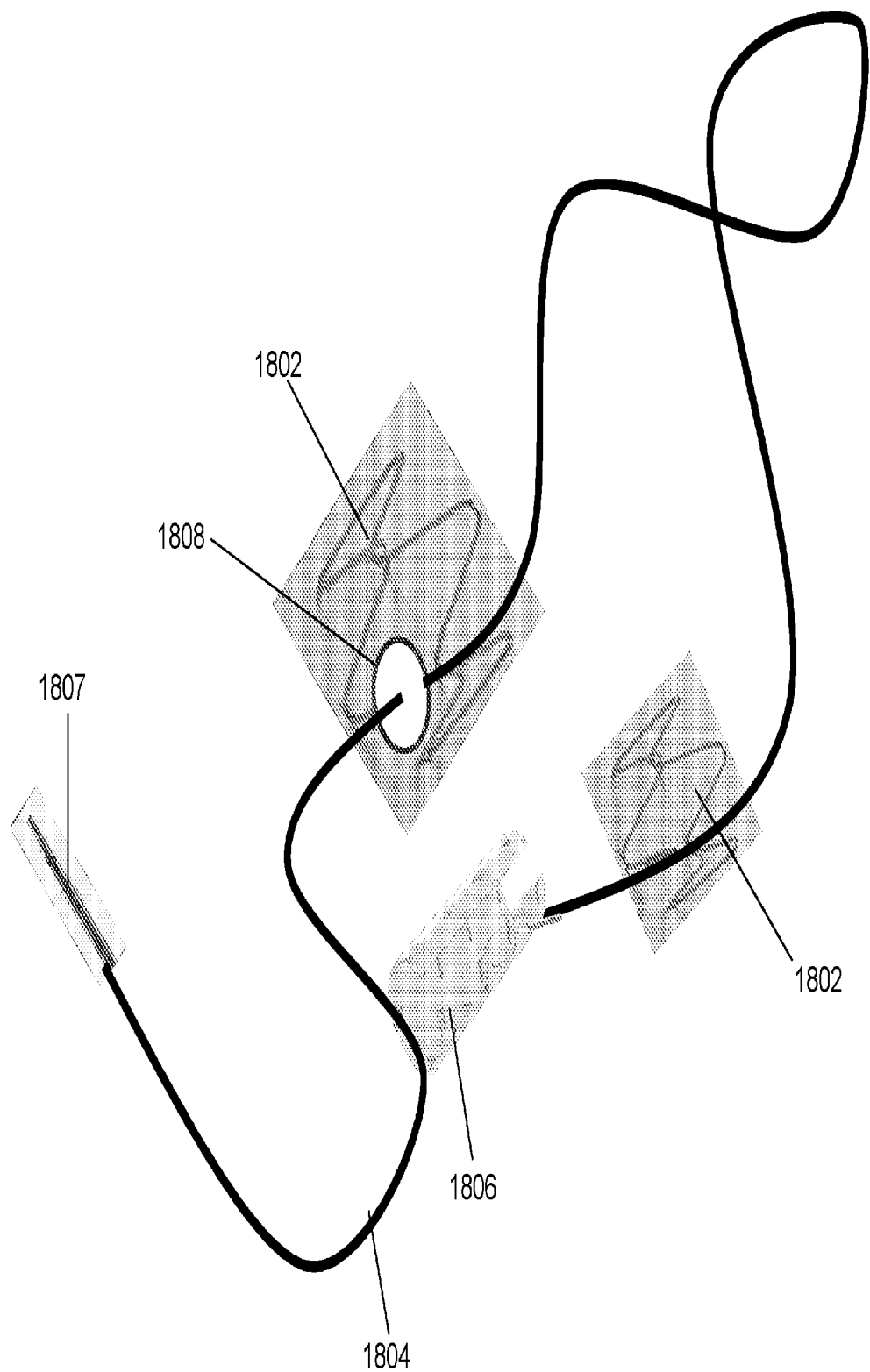
FIG. 18A illustrates anchors for holding an electrode lead within a blood vessel in accordance with one embodiment of the present specification.

FIG. 18A illustrates anchors 1802 for holding an electrode lead 1804 within a blood vessel. In various embodiments, an electrode coupled with a lead is inserted within a blood vessel for placement of the electrode within the blood vessel, such as shown in FIGS. 14A-14D. The blood vessel may be any artery or vein requiring hemorrhage treatment. FIG. 18A illustrates anchors 1802 which are used to hold the lead 1804 of the electrode 1806 in a desired position within a blood vessel and close to the vessel wall, preventing clot formation on the lead wall. The lead 1804 ends in a connector 1807 for connecting with a pulse generator (not shown), enabling application of electrical stimulation to the blood vessel.

In various embodiments, the electrode 1806 coupled with the lead 1804 is inserted within an intravascular catheter for placing the electrode 1806 within a blood vessel. The catheter is used to puncture the blood vessel for placing the electrode 1806 within. In an embodiment, the anchors 1802 also comprise a patch 1808 which is used to seal the puncture site at the position of entry of the catheter into the blood vessel in order to prevent bleeding or hematoma formation. In various embodiments, the patch is composed of PTFE, silicone, or of other materials known in the art for creating intravascular stent grafts. In various embodiments, the patch dimensions range from 2× to 200× the diameter of the intravascular catheter, which in turn determines the size of the puncture opening.

Figure 18B:
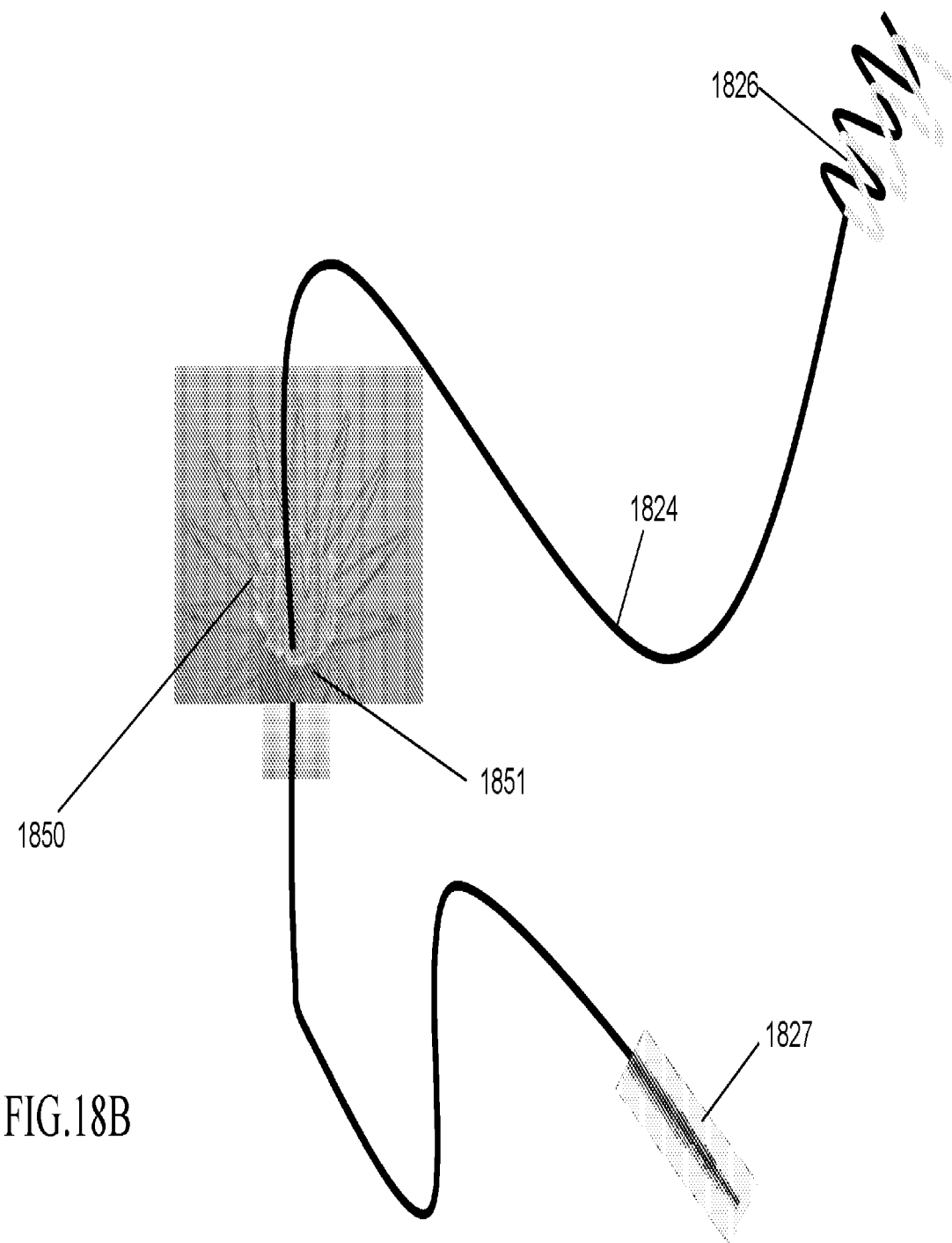
FIG. 18B illustrates anchors for holding an electrode lead within a blood vessel in accordance with another embodiment of the present specification.

FIG. 18B illustrates another embodiment of anchors 1850 for holding an electrode lead 1824 within a blood vessel. Anchor 1850 is used to hold lead 1824 of the electrode 1826 in a desired position within a blood vessel. In various embodiments, the anchor 1850 is partially or completely covered with PTFE 1851 or a similar material used in endovascular grafts and functions in positioning the lead body as well as sealing the puncture site. The lead 1824 ends in a connector 1827 for connecting with a pulse generator (not shown), enabling application of electrical stimulation to the blood vessel.

Figures 19A, 19B:
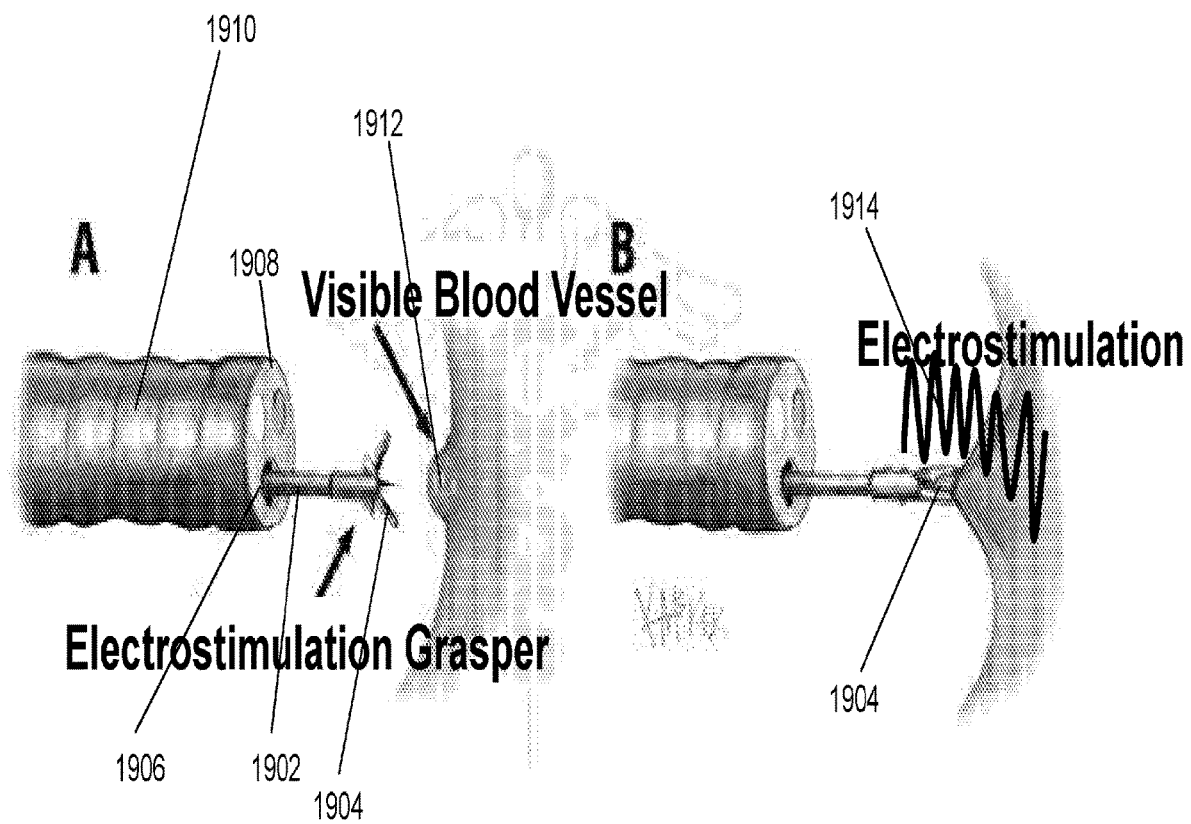
FIG. 19A illustrates a surgical device having an articulating jaw operable as forceps, protruding from an opening of a tip of an endoscope catheter proximate to a blood vessel having a hemorrhage, in accordance with an embodiment of the present specification.
FIG. 19B illustrates electrostimulation being applied to a blood vessel via the articulating jaws of FIG. 19A.

In an embodiment, an articulating jaw is used to provide electrical stimulation to a blood vessel in order to control a hemorrhage of the vessel. An electrostimulation device with articulating jaws may be passed through an endoscope within a patient's body and may be placed proximate a vascular structure for application of electrical stimulation to the vascular structure. FIG. 19A illustrates a surgical device 1902 having an articulating jaw 1904 which can operate as forceps, operating similarly to a hot biopsy forceps, protruding from an opening 1906 of a tip 1908 of an endoscope 1910, proximate a blood vessel 1912 having a hemorrhage. The surgical device 1902 providing electrostimulation may be monopolar or bipolar and, in an embodiment, includes an impedance sensor that measures the impedance to control the delivery of electrical stimulation to blood vessel 1912.

FIG. 19B illustrates electrostimulation being applied to a blood vessel via articulating jaw 1904, in accordance with an embodiment of the present specification. Electrostimulation causes vasoconstriction of blood vessel 1912 without coagulation. In an embodiment, an additional coagulation current may also be applied to blood vessel 1912 after vasoconstriction to seal the vascular structure. In various embodiments, the coagulation current has a frequency >100 kHz and preferably ranges from 300 kHz to 3 MHz. As shown in FIG. 19B, articulating jaw 1904 is used to grasp the vascular structure to cause mechanical tamponade, prior to applying the electrostimulation, to assist with vasoconstriction.

Figure 20A:
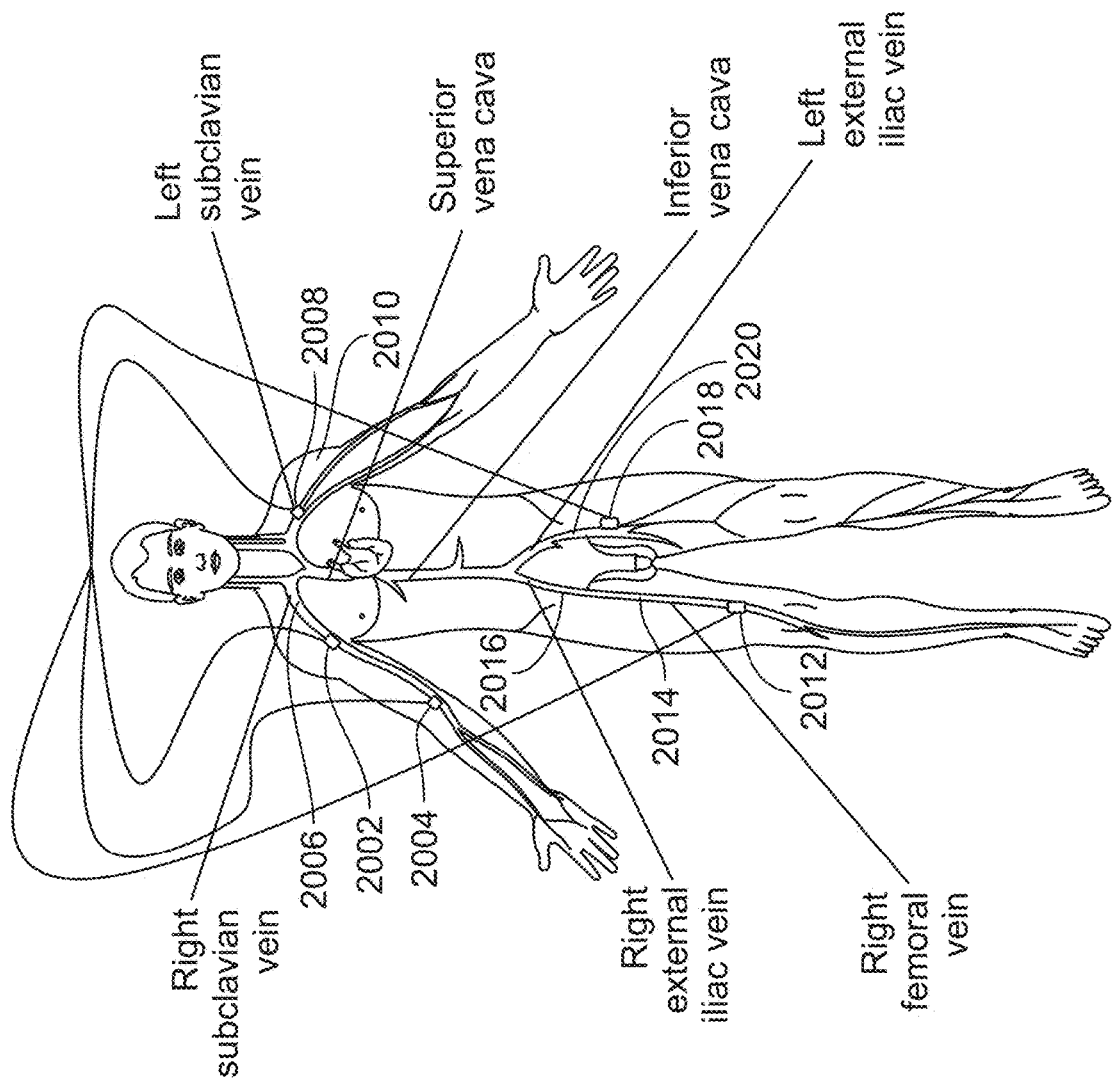
FIG. 20A illustrates sites within a human body for implantation of an active or passive wireless microdevice for delivering electrical stimulations to a blood vessel, in accordance with an embodiment of the present specification.

In various embodiments, one or more active or passive wireless microdevices are permanently implanted proximate a vascular structure supplying a limb of a patient. In the event of a traumatic injury to the limb, the device is activated with an external device, such as a handheld remote control device, to deliver electrical stimulation to control hemorrhage from the vascular structure as explained in the preceding sections of the specification. In various embodiments, the implantable microdevices comprise inert passive devices or active microstimulators as known in the art. FIG. 20A illustrates sites within a human body for implanting an active or passive wireless microdevice, in accordance with embodiments of the present specification. As shown, microdevices 2002 and 2004 are implanted proximate (or within) a right subclavian vein 2006 and micro device 2008 is implanted proximate (or within) a left subclavian vein 2010. Similarly, microdevice 2012 is implanted proximate (or within) a right femoral vein 2014, which extends from a right external iliac vein 2016, and microdevice 2018 is implanted proximate (or within) a left external iliac vein 2020. As would be apparent to persons of skill in the art, the sites of implantation of microdevices shown in FIG. 20A are only exemplary and microdevices used for providing electrical stimulation may be implanted within multiple other blood vessels in the human body. FIG. 20B illustrates an exemplary implantable microdevice 2019 used for delivering electrical stimulation to blood vessels, in accordance with an embodiment of the present specification. The microdevice 2019 can be implanted using a needle 2021.

FIG. 20C illustrates an exemplary hand held remote control device 2022 for activating an implanted microdevice for delivering electrical stimulation to blood vessels, in accordance with an embodiment of the present specification. The hand held remote could be operated by the patient receiving the electrical stimulation or by another person. FIG. 20D illustrates another exemplary hand held remote control device 2024 for activating an implanted microdevice for delivering electrical stimulation to blood vessels, in accordance with another embodiment of the present specification. In an embodiment, the remote control device 2024 may be a smart phone with a predefined application for activating the implanted microdevice running on it. As shown in FIG. 20D, in some embodiments, a screen of the remote control device 2024 displays a list of individual implanted microdevices located at different regions of a body and, based on the site of the injury, the specific microdevice can be activated for delivering electrical stimulation to the specified body region via the remote control device 2024.

Figure 20E:
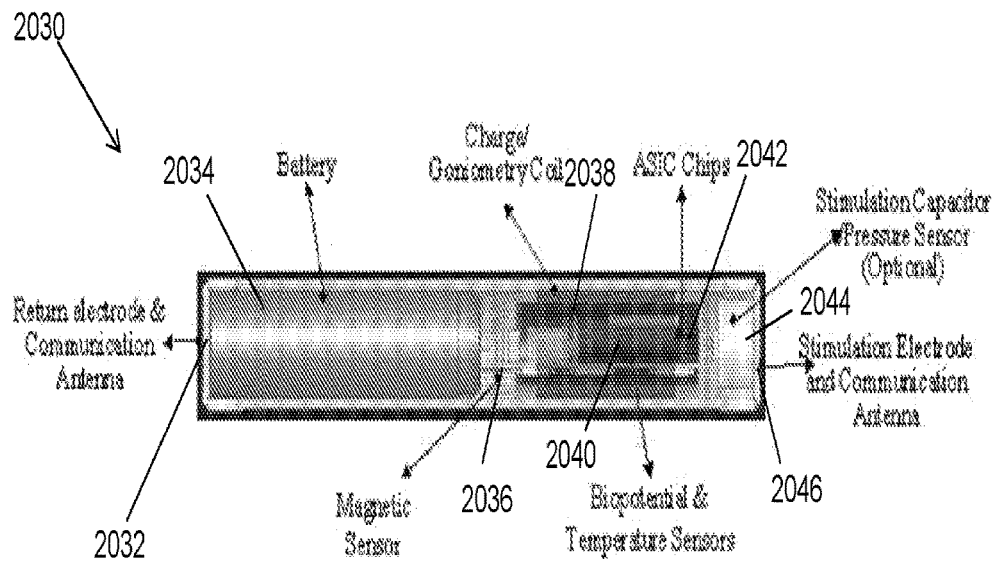
FIG. 20E illustrates an exemplary implantable microdevice used for delivering electrical stimulation to blood vessels, in accordance with an embodiment of the present specification.
Figure 20F:
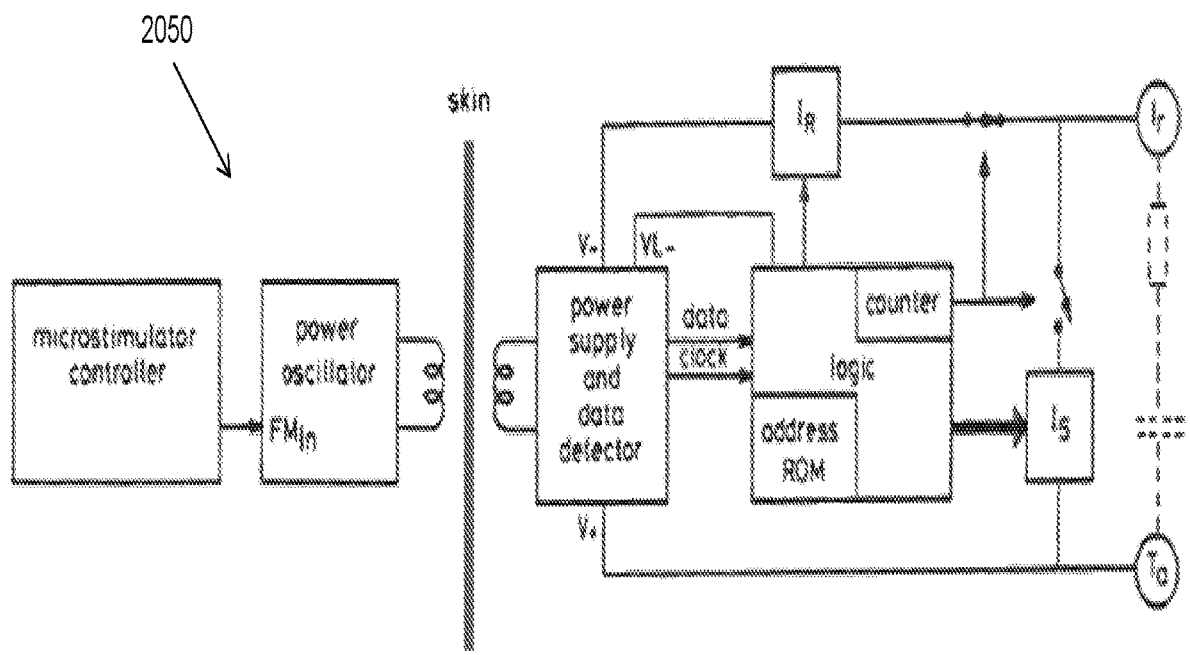
FIG. 20F illustrates an exemplary circuit diagram of an implantable microdevice used for delivering electrical stimulation to blood vessels, in accordance with an embodiment of the present specification.

FIG. 20E illustrates an exemplary implantable microdevice 2030 used for delivering electrical stimulation to blood vessels, in accordance with an embodiment of the present specification. Microdevice 2030 comprises a communication antenna 2032 for communicating with a hand held remote control device, such as those shown in FIGS. 20C and 20D, for activating the micro device 2030. Communication antenna 2032 is coupled with a battery 2034 or any mechanism of storing energy such as a capacitor for powering the microdevice 2030. The electronic circuitry of microdevice 2030 comprises a magnetic sensor 2036 coupled with a charge coil 2038 which in turn is coupled with one or more bio-potential and temperature sensors 2040, all positioned on ASCI chip 2042, which is coupled with simulation capacitor 2044 and a simulation electrode and communication antenna 2046. FIG. 20F illustrates an exemplary circuit diagram 2050 of a microdevice used for delivering electrical stimulation to blood vessels, in accordance with an embodiment of the present specification.

Figure 20G:
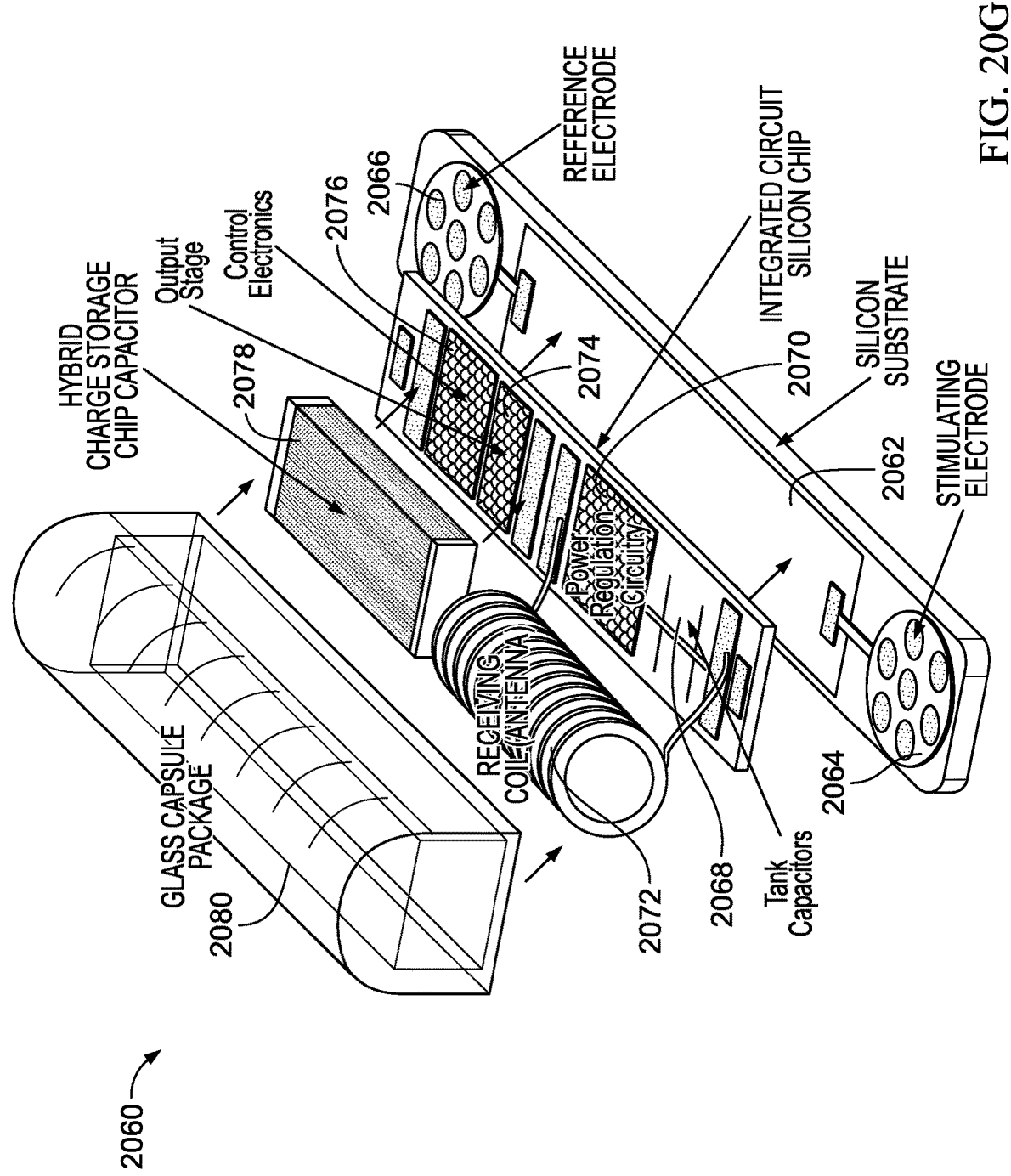
FIG. 20G illustrates another exemplary implantable micro device used for delivering electrical stimulation to blood vessels, in accordance with another embodiment of the present specification.

FIG. 20G illustrates another exemplary implantable microdevice 2060 used for delivering electrical stimulation to blood vessels, in accordance with an embodiment of the present specification. Microdevice 2060 comprises an elongated silicon substrate 2062 comprising stimulating electrode 2064 and a reference electrode 2066 placed at a proximal and a distal end respectively. The portion of the substrate 2062 between the proximal and distal ends comprises electronic circuitry such as tank capacitors 2068, power regulation circuitry 2070 coupled with a recycling coil antenna 2072, and an output stage 2074 and control electronics 2076 coupled with a hybrid charge storage chip capacitor 2078 as shown. The entire substrate 2062 comprising all the electrodes 2064, 2066 and all the electronic circuitry is encased in a glass capsule package 2080 or any other hermetically sealed packaging.

Figure 21:
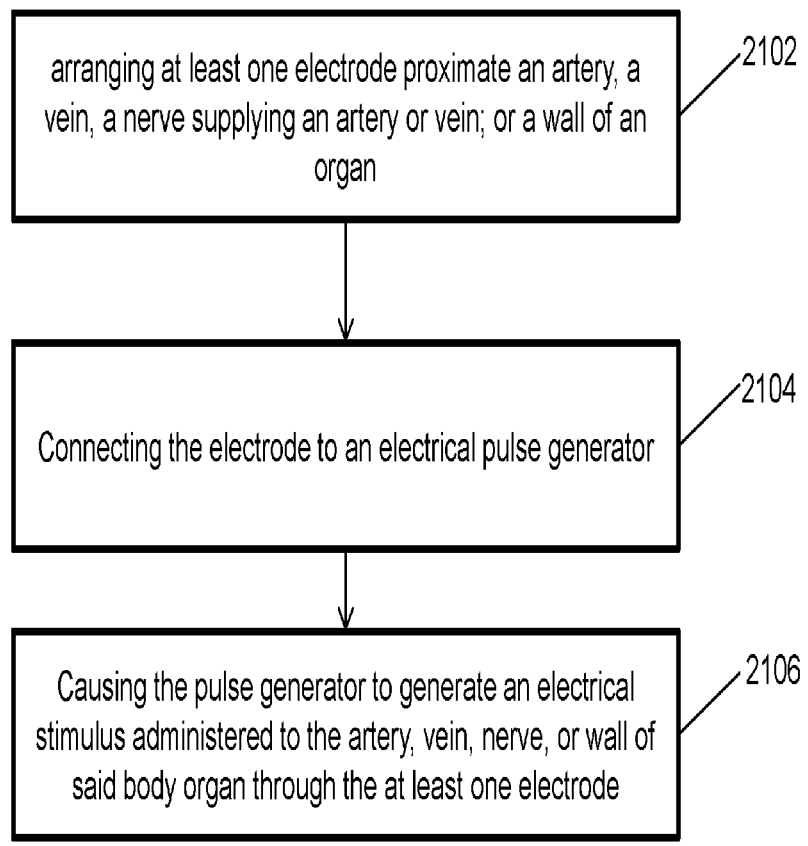
FIG. 21 is a flowchart illustrating the steps of modulating blood flow via application of electrical stimulation to a blood vessel, in accordance with an embodiment of the present specification.

FIG. 21 is a flowchart illustrating the steps of modulating blood flow via application of electrical stimulation to a blood vessel, in accordance with an embodiment of the present specification. At step 2102 at least one electrode is arranged proximate an artery, a vein, a nerve supplying an artery or vein, or a wall of an organ. In various embodiments, any of the electrodes described with reference to FIG. 6 and FIGS. 10A through 14D may be used. At step 2104, the electrode is connected to an electrical pulse generator to provide electrical pulses of a desired frequency and amplitude for a desired duration. In an embodiment, a first electrical stimulation reaction threshold for vasoconstriction is predetermined. Further, a second reaction threshold for thrombosis in the subject is also predetermined. In an embodiment, the magnitude of electrical pulses is below the predetermined reaction threshold for thrombosis, but above the reaction threshold for vasoconstriction, such that the stimulus generates a predominance of vasoconstriction over thrombosis.

At step 2106 the electrode is activated to provide electrical stimulation for modulating blood flow to the organ being supplied by the artery or the vein. In an embodiment, the electrode is activated and the electrical stimulation is controlled via an algorithm running on a computing device coupled with the electrical pulse generator. In an embodiment, the algorithm may cause the electrode to be stimulated only upon occurrence of a bleeding in a corresponding artery, vein or organ. In another embodiment, the algorithm may induce the electrode to apply a first stimulation that causes artery/vein constriction such that a baseline blood flow greater than 50% or 75% or 90% of the maximum blood flow is maintained, and a second stimulation in case of occurrence of bleeding to decrease blood flow to less than 50%, 25% or 10% of the maximum blood flow. In other embodiments, the electrical stimulation is applied for a duration wherein, after the cessation of the electrical stimulation, the change in the blood flow is maintained for at least 1 minute. In other embodiments, electrical stimulation is applied for another duration wherein, after the cessation of the electrical stimulation, the change in the blood flow is maintained for at least 5 minutes. In other embodiments, the electrical stimulation is intermittently turned on and off to maintain adequate control on the blood flow to allow for adequate hemostasis without compromising the viability of the organs supplied by the blood vessel. The duty cycle in such a scenario ranges from 1% to 99%. In some embodiments, the ideal duty cycle ranges from 10% to 90%. In other embodiments, the stimulation parameters, including specific duty cycle, are configured to produce vasodilation.

In an embodiment, the present specification provides a method of treating a hemorrhage by applying electrical stimulation at a pre-defined location, wherein the hemorrhage site is downstream from the stimulation location. The electrical stimulation may be provided by placing an electrode (connected to an electrical pulse generator) in proximity to (or within) a blood vessel for modulating blood flow downstream to the hemorrhage site.

In various embodiments, an electrical current having a frequency of up to 1000 KHz may be used to stimulate the blood vessels without causing thermal damage to the vessel wall or coagulation. Electrical stimulation above 1000 KHz usually generates some heat which may harm the blood vessels. In an embodiment, electrical stimulation may be applied to a blood vessel supplying a body organ, causing vasoconstriction for preventing a hemorrhagic condition in the body organ during a surgical procedure. In embodiments, a vasoconstriction of less than 25% is non-therapeutic, whereas a vasoconstriction between 25% to 50% is used for preventing a hemorrhagic condition. Further, a vasoconstriction of greater than 50% is used to treat a hemorrhage.

In various embodiments, each stimulation site serves a different hemorrhage site that is downstream from the stimulation site. In exemplary embodiments, a stimulation site in an upper limb of a patient serves to modulate blood flow (and thereby treat hemorrhage conditions) in the entire limb downstream of the upper limb stimulation site. Similarly, a stimulation site in a lower limb of a patient serves to modulate blood flow (and thereby treat hemorrhage conditions) in the entire limb downstream of the lower limb stimulation site.

Figure 22A:
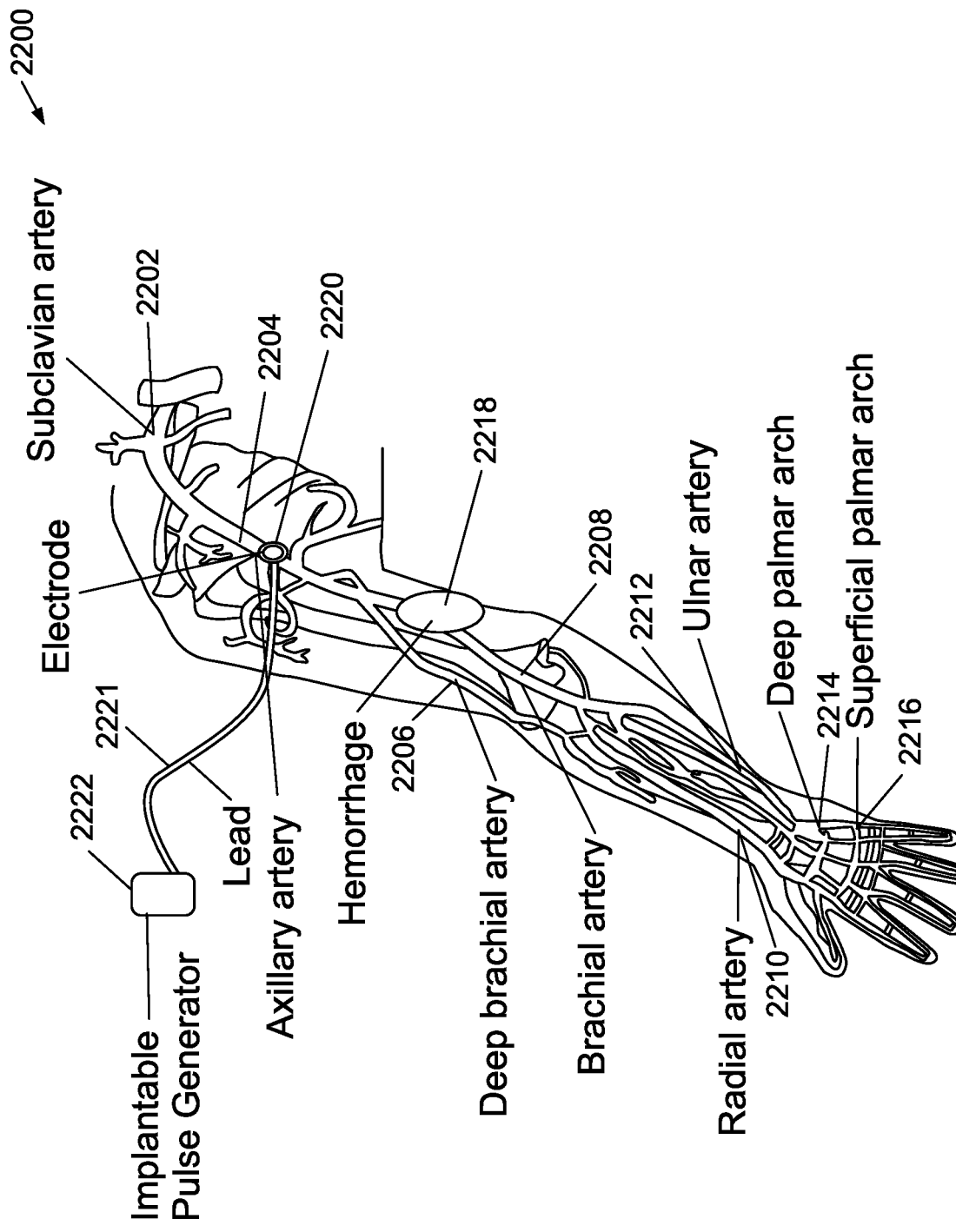
FIG. 22A illustrates stimulation provided to a blood vessel in an upper limb of a patient to control bleeding downstream from the stimulation site, in accordance with an embodiment of the present specification.

FIG. 22A illustrates stimulation provided to a blood vessel in an upper limb of a patient to control bleeding downstream from the stimulation site, in accordance with an embodiment of the present specification. As described earlier, a nerve supplying the blood vessel may also be stimulation to achieve the same desired therapeutic effect. As shown, the upper limb or arm 2200 comprises blood vessels such as subclavian artery 2202, axillary artery 2204, deep brachial artery 2206, brachial artery 2208, radial artery 2210, ulnar artery 2212, deep palmar arch 2214, and superficial palmar arch 2216. In case of a hemorrhage in one of the blood vessels in the arm 2200, such as the exemplary hemorrhage 2218 in the brachial artery 2208 as shown in FIG. 22A, electrical stimulation is applied to a blood vessel at a site positioned upstream from the hemorrhage 2218. In an exemplary embodiment, the stimulation is applied to the axillary artery 2204 by placing therein or proximate thereto an electrode 2220 coupled with an implantable pulse generator 2222 via lead 2221. The electrode 2220, activated via the pulse generator 2222, provides electrical stimulation to constrict the axillary artery 2204 and modulate the blood flowing downstream to the hemorrhage 2218 in the brachial artery 2208. In embodiments, the electrode 2220 may be placed in proximity to any viable blood vessel at a location upstream from the hemorrhage site 2218. In an embodiment, a palpable vessel area at a distance ranging between 0.5 and 5 cm from the vessel is identified for placing the electrode 2220, wherein the electrode placement site is at least 1 cm from the hemorrhage site 2218.

Figure 22B:
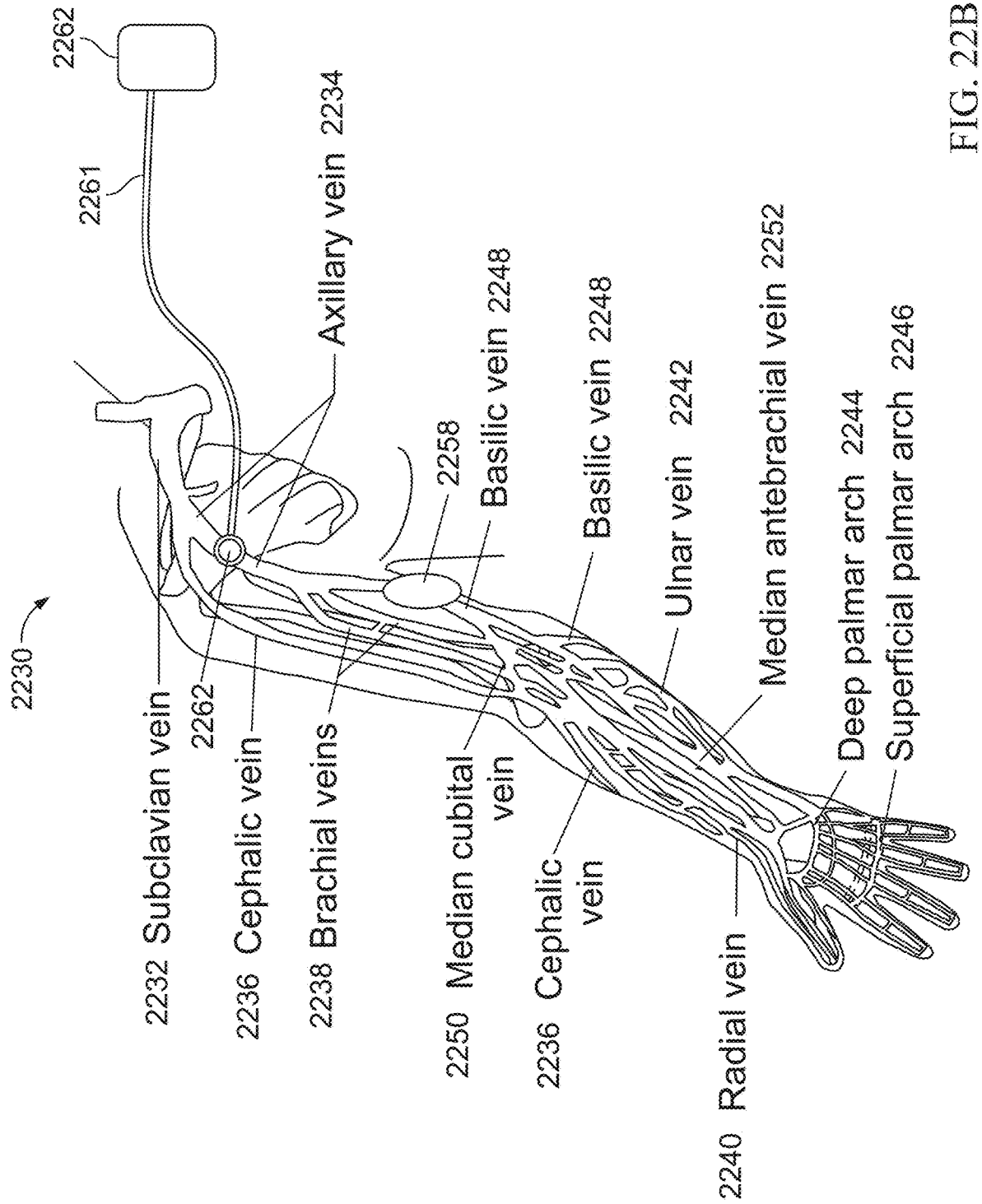
FIG. 22B illustrates stimulation provided to a blood vessel in an upper limb of a patient to control bleeding downstream from the stimulation site, in accordance with another embodiment of the present specification.

FIG. 22B illustrates stimulation provided to a blood vessel in an upper limb of a patient to control bleeding downstream from the stimulation site, in accordance with another embodiment of the present specification. As shown, the upper limb or arm 2230 comprises blood vessels such as subclavian vein 2232, axillary vein 2234, cephalic vein 2236, brachial veins 2238, radial vein 2240, ulnar vein 2242, deep palmar arch 2244, superficial palmar arch 2246, basilic vein 2248, median cubital vein 2250, and median antebrachial vein 2252. In case of a hemorrhage in one of the blood vessels in the arm 2230, such as the exemplary hemorrhage 2258 in the basilica vein 2248 as shown in FIG. 22B, electrical stimulation is applied to a blood vessel at a site positioned upstream from the hemorrhage 2258. In an exemplary embodiment, the stimulation is applied to the axillary vein 2234 by placing therein or proximate thereto an electrode 2260 coupled with an implantable pulse generator 2262 via lead 2261. The electrode 2260, activated via the pulse generator 2262, provides electrical stimulation to constrict the axillary vein 2234 and modulate the blood flowing downstream to the hemorrhage 2258 in the basilic vein 2248. In embodiments, the electrode 2260 may be placed in proximity to any viable blood vessel at a location upstream from the hemorrhage site 2258. In an embodiment, a palpable vessel area at a distance ranging between 0.5 and 5 cm from the skin surface is identified for placing the electrode 2260, wherein the electrode placement site is at least 1 cm from the hemorrhage site 2258.

Figure 23:
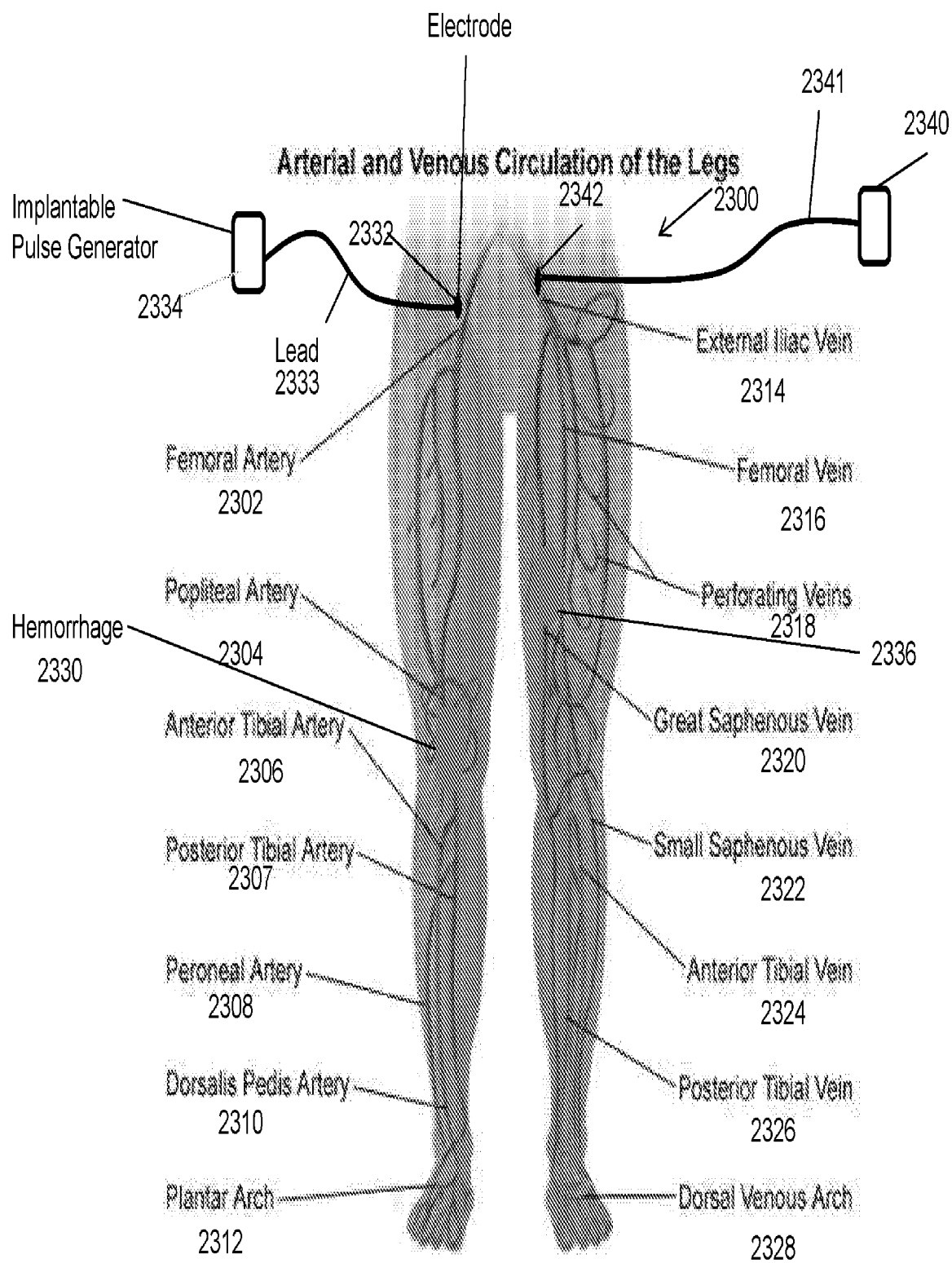
FIG. 23 illustrates stimulation provided to a blood vessel in a lower limb of a patient to control bleeding downstream from the stimulation site, in accordance with an embodiment of the present specification.

FIG. 23 illustrates stimulation provided to a blood vessel in a lower limb of a patient to control bleeding downstream from the stimulation site, in accordance with an embodiment of the present specification. As shown, lower limb or leg 2300 comprises blood vessels including both arteries and veins such as femoral artery 2302, popliteal artery 2304, anterior tibial artery 2306, posterior tibial artery 2307, peroneal artery 2308, dorsalis pedis artery 2310 and plantar arch 2312, external iliac vein 2314, femoral vein 2316, perforating veins 2318, great saphenous vein 2320, small saphenous vein 2322, anterior tibial vein 2324, posterior tibial vein 2326, and dorsal venous arch 2328. In case of a hemorrhage in one of the blood vessels in the leg 2300, such as the exemplary hemorrhage 2330 in the popliteal artery 2304 as shown in FIG. 23, electrical stimulation is applied to a blood vessel at a site positioned upstream from the hemorrhage 2330.

In an exemplary embodiment, the stimulation is applied to the femoral artery 2302 by placing therein or proximate thereto an electrode 2332 coupled with an implantable pulse generator 2334 via lead 2333. The electrode 2332, activated via the pulse generator 2334, provides electrical stimulation to constrict the femoral artery 2302 and modulate the blood flowing downstream to the hemorrhage 2330 in the popliteal artery 2302. In embodiments, the electrode 2332 may be placed in electrical communication with any viable blood vessel at a location upstream from the hemorrhage site 2330. In an embodiment, a palpable vessel area at a distance ranging between 0.5 cm and 5 cm from the skin surface is identified for placing the electrode 2332, wherein the electrode placement site is at least 1 cm from the hemorrhage site 2330.

In case of a hemorrhage in one of the veins in the leg 2300, such as the exemplary hemorrhage 2336 in the great saphenous vein 2320 as shown in FIG. 23, electrical stimulation is applied to a blood vessel at a site positioned upstream from the hemorrhage 2336.

In an exemplary embodiment, the stimulation is applied to the external iliac vein 2314 by placing therein or proximate thereto an electrode 2342 coupled with an implantable pulse generator 2340 via lead 2341. The electrode 2342, activated via the pulse generator 2340, provides electrical stimulation to constrict the external iliac vein 2314 and modulate the blood flowing downstream to the hemorrhage 2336 in the greater saphenous vein 2320. In embodiments, the electrode 2342 may be placed in electrical communication with any viable blood vessel at a location upstream from the hemorrhage site 2336. In an embodiment, a palpable vessel area at a distance ranging between 0.5 and 5 cm from the skin surface is identified for placing the electrode 2342, wherein the electrode placement site is at least 1 cm from the hemorrhage site 2336.

The embodiments described with reference to FIGS. 22A, 22B, and 23 would be effective for treating hemorrhages occurring following trauma to the upper limb and lower limb respectively, such as hemorrhages caused by accidents.

Figure 24:
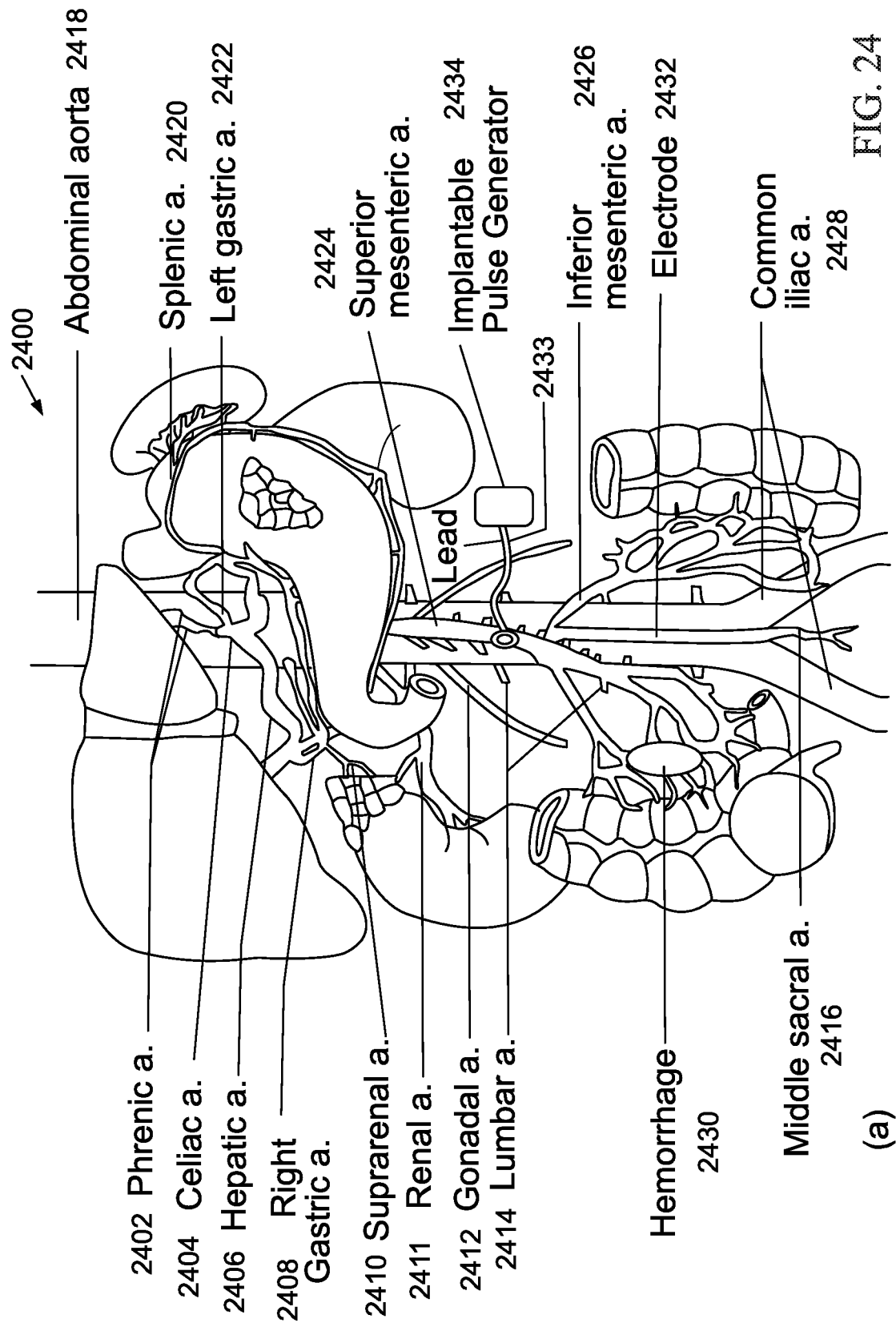
FIG. 24 illustrates stimulation provided to a blood vessel in an abdomen of a patient to control bleeding downstream from the stimulation site, in accordance with an embodiment of the present specification.

FIG. 24 illustrates stimulation provided to a blood vessel in an abdomen of a patient to control bleeding downstream from the stimulation site, in accordance with an embodiment of the present specification. As shown, abdomen 2400 is supplied blood via blood vessels such as phrenic artery 2402, celiac artery 2404, hepatic artery 2406, right gastric artery 2408, suprarenal artery 2410, renal artery 2411, gonadal artery 2412, lumbar artery 2414, middle sacral artery 2416, abdominal aorta 2418, splenic artery 2420, left gastric artery 2422, superior mesenteric artery 2424, inferior mesenteric artery 2426 and common iliac artery 2428. In case of a hemorrhage in one of the blood vessels in the abdomen 2400, such as the exemplary hemorrhage 2430 in the lumbar artery 2414 as shown in FIG. 24, electrical stimulation is applied to a blood vessel at a site positioned upstream from the hemorrhage 2430. In an exemplary embodiment, the stimulation is applied to the superior mesenteric artery 2424 by placing therein or proximate thereto an electrode 2432 coupled with an implantable pulse generator 2434 via lead 2433. The electrode 2432, activated via the pulse generator 2434, provides electrical stimulation to constrict the superior mesenteric artery 2424 and modulate the blood flowing downstream to the hemorrhage 2430 in the lumbar artery 2414. In embodiments, the electrode 2432 is placed in proximity to any viable blood vessel at a location upstream from the hemorrhage site 2430. In an embodiment, a palpable vessel area at a distance ranging between 0.5 cm and 5 cm from the skin surface is identified for placing the electrode 2432, wherein the electrode placement site is at least 1 cm from the hemorrhage site 2430.

Since hemorrhages are commonly observed in the abdominal region due to surgical procedures, in embodiments, electrodes for providing electrical stimulation are placed at one or more pre-defined locations within a patient's abdominal cavity prior to a surgical procedure. During the surgical procedure, blood loss from a blood vessel may be controlled by activating an electrode placed in proximity to any blood vessel lying upstream from the hemorrhage for providing electrical stimulation, as explained with reference to FIG. 24. Hence, in embodiments, vasoconstriction achieved by application of electrical stimulation to a blood vessel for controlling blood loss functions like a real-time electronic tourniquet and is used for preventing a hemorrhagic condition during a surgery. Such an approach is preferable to using physical clamps in real time as it is quicker and can be adjusted more easily.

Figure 25:
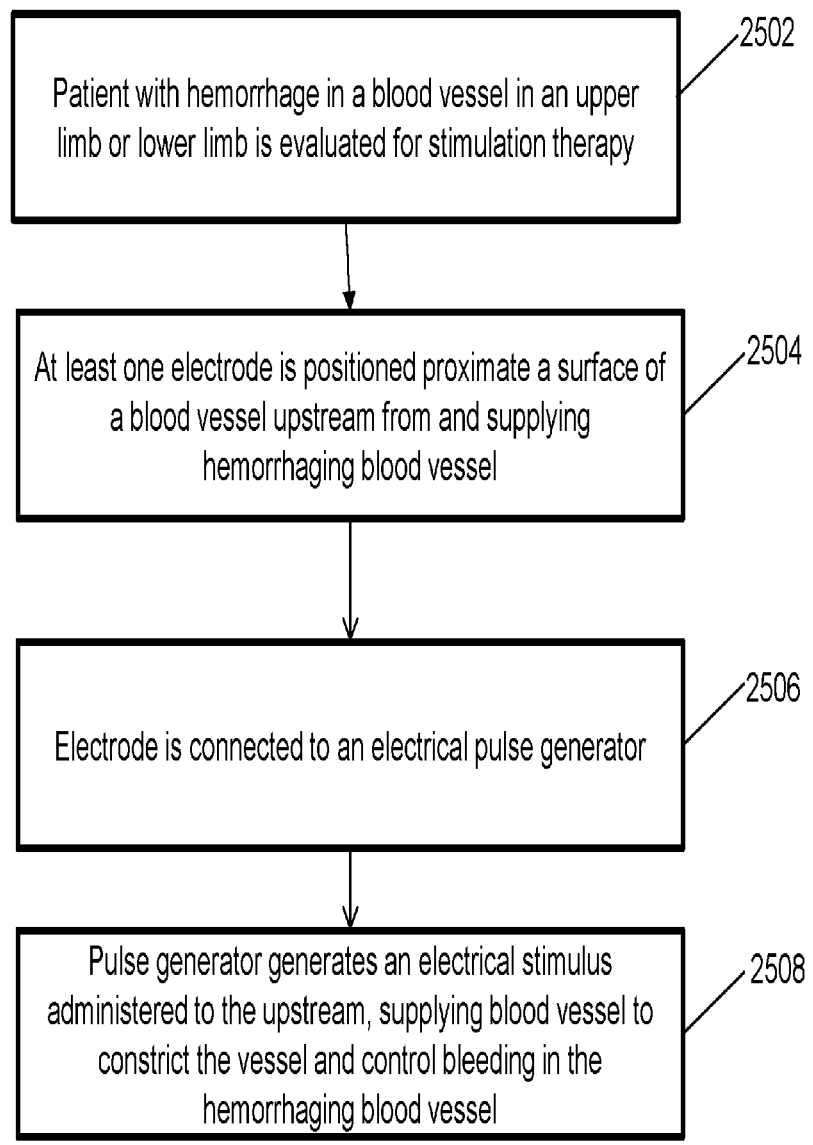
FIG. 25 is a flowchart illustrating the steps of controlling a hemorrhage in an upper limb or lower limb of a patient via application of electrical stimulation to a blood vessel upstream from a hemorrhage site, in accordance with an embodiment of the present specification.

FIG. 25 is a flowchart illustrating the steps of controlling a hemorrhage in an upper limb or lower limb of a patient via application of electrical stimulation to a blood vessel upstream from a hemorrhage site, in accordance with an embodiment of the present specification. At step 2502, a patient with a hemorrhage in a blood vessel in an upper limb or lower limb is evaluated for stimulation therapy. At least one electrode is positioned proximate a surface of a blood vessel upstream from and supplying a hemorrhaging blood vessel at step 2504. In various embodiments, the electrode is positioned at least 1 cm upstream from a location of the hemorrhage. In various embodiments, the blood vessel is an artery comprising at least one of a subclavian artery, an axillary artery, a deep brachial artery, a brachial artery, a radial artery, an ulnar artery, a deep palmar arch, and a superficial palmar arch or a vein comprising at least one of subclavian vein, axillary vein, cephalic vein, brachial vein, radial vein, ulnar vein, deep palmar arch, superficial palmar arch, basilic vein, median cubital vein, and median antebrachial vein. In other embodiments, the blood vessel is an artery comprising as least one of a femoral artery, popliteal artery, anterior tibial artery, posterior tibial artery, peroneal artery, dorsalis pedis artery, and plantar arch or a vein comprising at least one of an external iliac vein, femoral vein, perforating vein, great saphenous vein, small saphenous vein, anterior tibial vein, posterior tibial vein, and dorsal venous arch. The electrode is connected to an electrical pulse generator at step 2506. At step 2508, the pulse generator generates an electrical stimulus administered to the upstream, supplying blood vessel to constrict the vessel and control bleeding in the hemorrhaging blood vessel. The electrical stimulus has a pulse duration, a pulse amplitude, and a pulse frequency selected such that the electrical stimulus is effective to cause vasoconstriction in said artery or said vein.

Figure 26A:
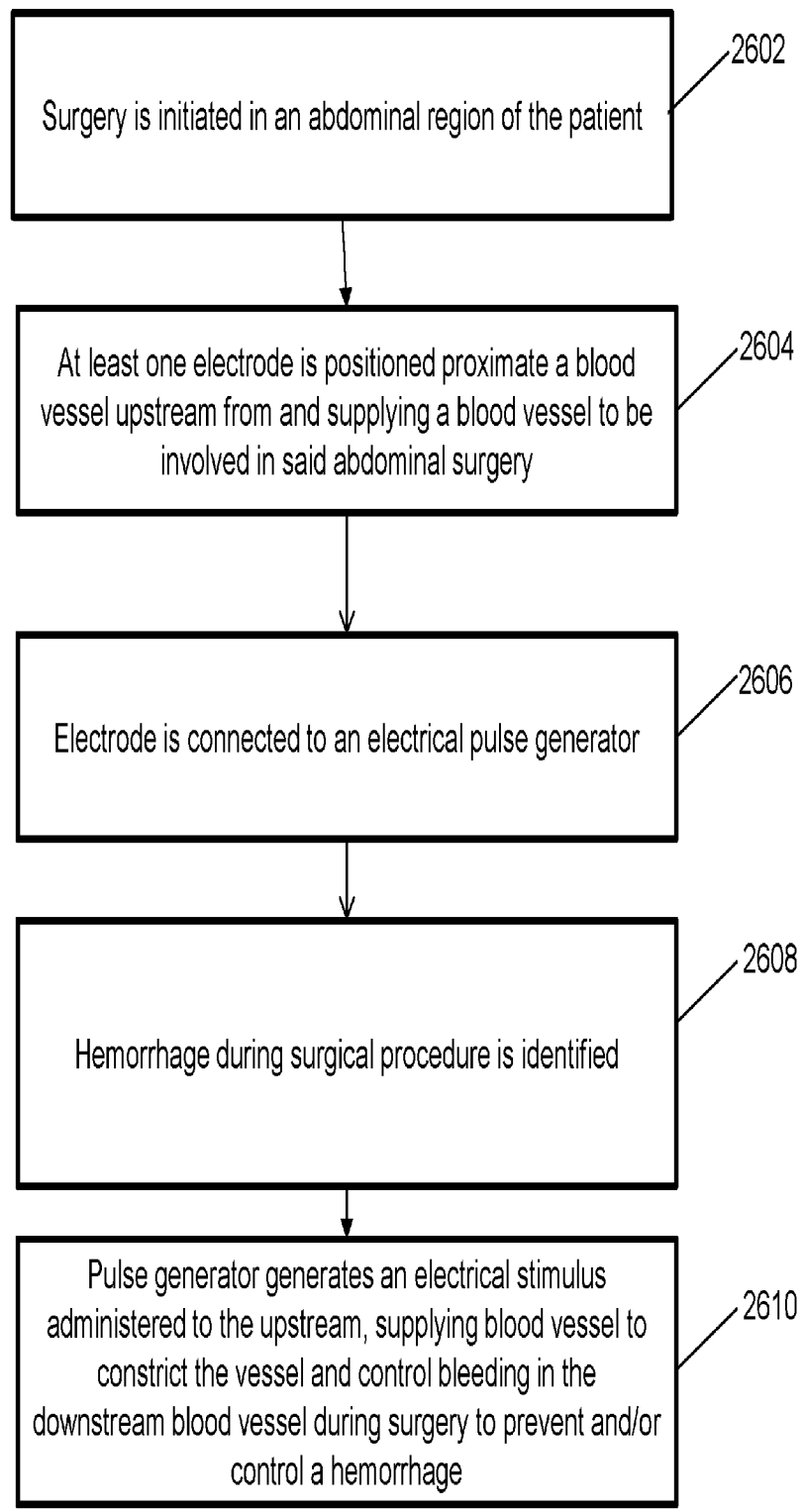
FIG. 26A is a flowchart illustrating the steps of preventing and/or controlling a hemorrhage in a patient during abdominal surgery via application of electrical stimulation to a blood vessel upstream from a possible hemorrhage site, in accordance with an embodiment of the present specification.

FIG. 26A is a flowchart illustrating the steps of preventing and/or controlling a hemorrhage in a patient during abdominal surgery via application of electrical stimulation to a blood vessel upstream from a possible hemorrhage site, in accordance with an embodiment of the present specification. At step 2602, surgery is initiated in an abdominal region of the patient. At least one electrode is positioned proximate a blood vessel upstream from and supplying a blood vessel to be involved in said abdominal surgery at step 2604. At step 2606, the electrode is connected to an electrical pulse generator. A hemorrhage during the surgical procedure is identified at step 2608. At step 2610, the pulse generator generates an electrical stimulus administered to the upstream, supplying blood vessel to constrict the vessel and control bleeding in the downstream blood vessel during surgery to prevent and/or control a hemorrhage, wherein the electrical stimulus has a pulse duration, a pulse amplitude, and a pulse frequency and wherein the pulse duration, pulse amplitude, and pulse frequency are selected such that the electrical stimulus is effective for causing vasoconstriction.

Figure 26B:
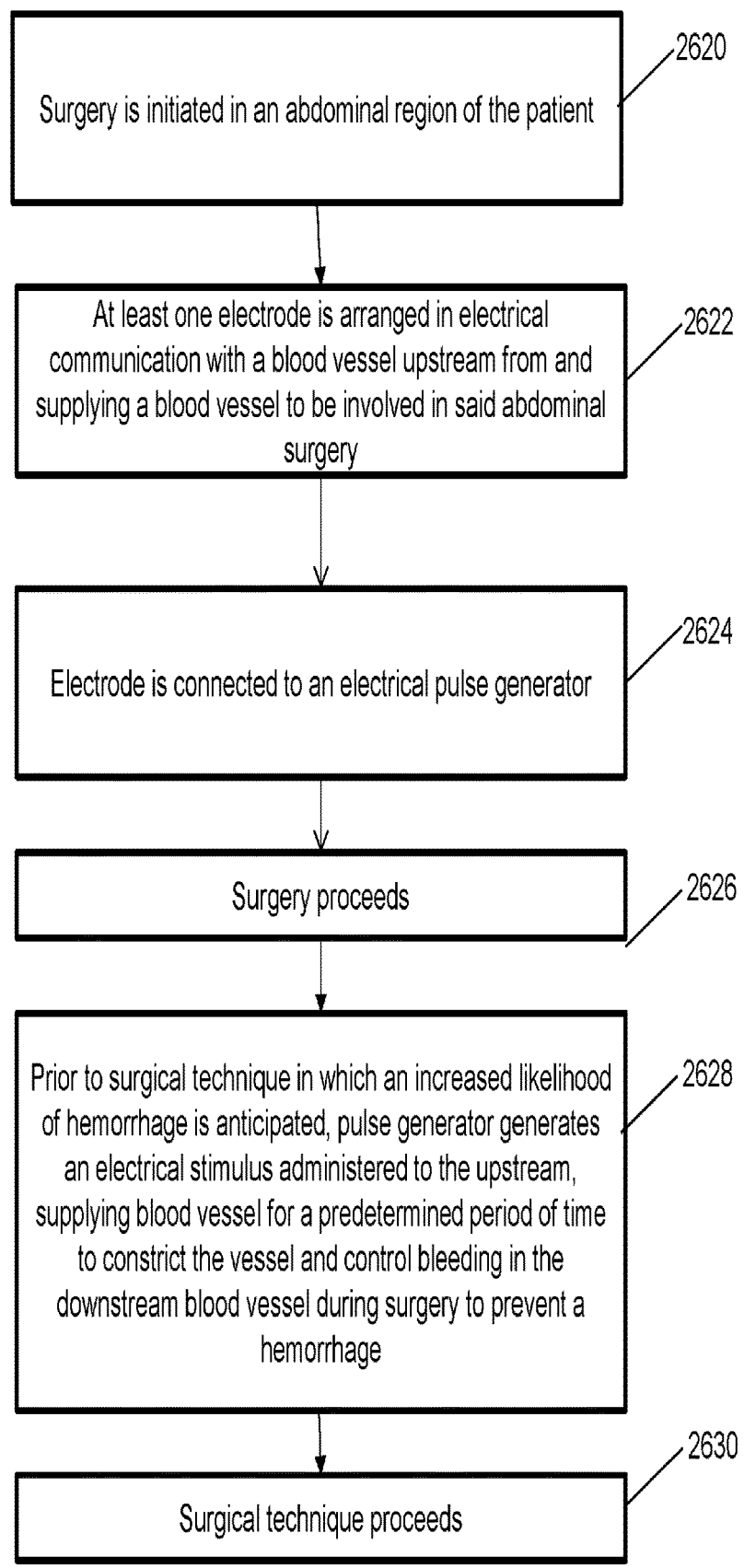
FIG. 26B is a flowchart illustrating the steps of preventing an anticipated hemorrhage in a patient during abdominal surgery via application of electrical stimulation to a blood vessel upstream from a possible hemorrhage site, in accordance with an embodiment of the present specification.

FIG. 26B is a flowchart illustrating the steps of preventing an anticipated hemorrhage in a patient during abdominal surgery via application of electrical stimulation to a blood vessel upstream from a possible hemorrhage site, in accordance with an embodiment of the present specification. At step 2620, a surgery is initiated in an abdominal region of said patient, wherein initiating surgery is defined as exposing an area proximate a blood vessel to be involved in said surgery. At least one electrode of a stimulation apparatus is arranged at a location in electrical communication with a blood vessel upstream to and supplying blood to a blood vessel in said abdominal region before a hemorrhage develops at step 2622. At step 2624, said at least one electrode is connected to an electrical pulse generator. Then, surgery proceeds at step 2626. Prior to the beginning of a surgical technique in which an increased likelihood of hemorrhage is anticipated, at step 2628, the pulse generator generates an electrical stimulus administered to the upstream blood vessel for a predetermined period of time, wherein the electrical stimulus has a pulse duration, a pulse amplitude, and a pulse frequency and wherein said pulse duration, said pulse amplitude, and said pulse frequency are selected such that the electrical stimulus is effective for causing vasoconstriction of the upstream blood vessel and reducing blood flow to prevent or control hemorrhage of the blood vessel involved in the abdominal region. The surgical technique then proceeds at step 2630.

In various embodiments, the predetermined period of time to administer electrical stimulation prior to the surgical technique is equal to at least 30 seconds. In some embodiments, the electrical stimulus is administered for at least 10 seconds during the surgical technique. In some embodiments, the electrical stimulus is administered both prior to beginning said surgical technique and for the duration of the remainder of the surgery. Further, in some embodiments, for example in some high risk cases, the at least one electrode is configured to remain within the abdominal region of the patient for a period of time ranging from 1 to 7 days and the electrical stimulus is administered post-operatively to treat post-operative hemorrhage.

Figure 27:
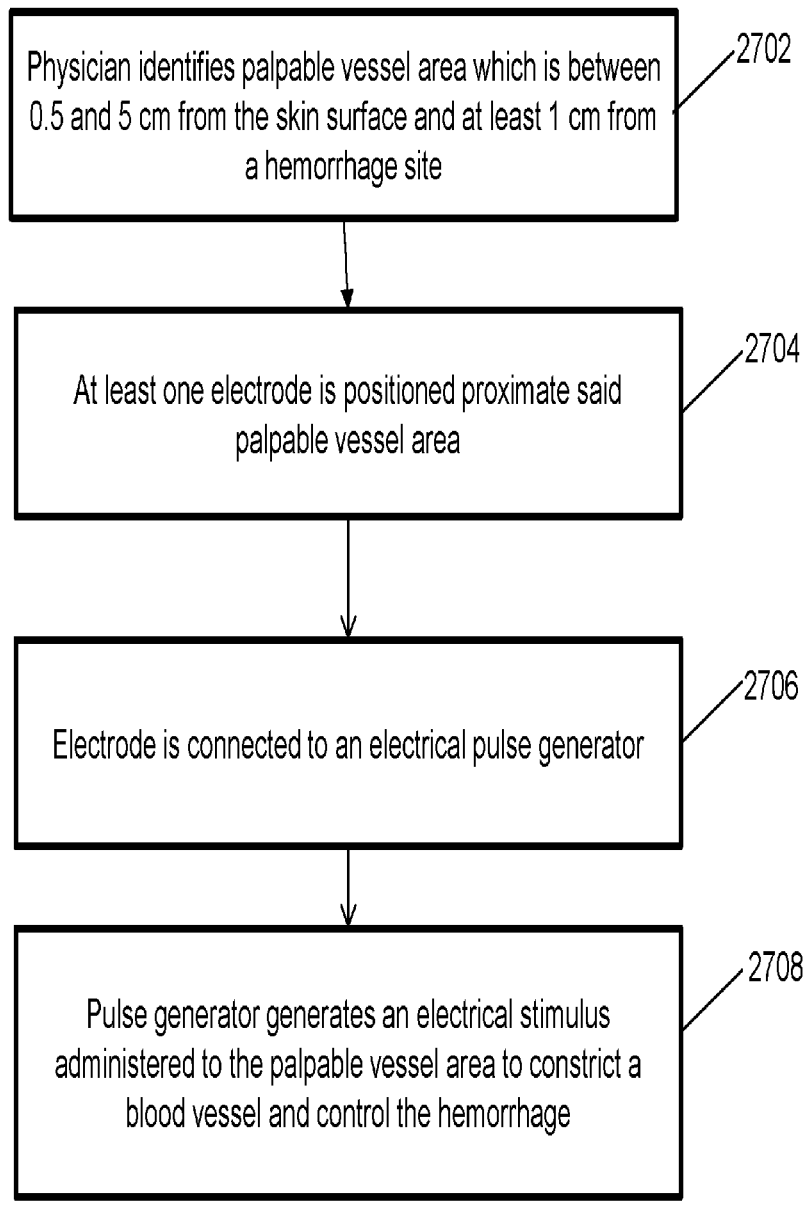
FIG. 27 is a flowchart illustrating the steps of locating a stimulation site on a skin surface and providing electrical stimulation to control a hemorrhage, in accordance with an embodiment of the present specification.

FIG. 27 is a flowchart illustrating the steps of locating a stimulation site on a skin surface and providing electrical stimulation to control a hemorrhage, in accordance with an embodiment of the present specification. At step 2702, a physician identifies a palpable vessel area which is between 0.5 and 5 cm from a patient's skin surface and at least 1 cm from a hemorrhage site. At least one electrode is positioned proximate said palpable vessel area at step 2704. The electrode is connected to an electrical pulse generator at step 2706. At step 2708, the pulse generator generates an electrical stimulus administered to the palpable vessel area to constrict a blood vessel and control the hemorrhage.

In other embodiments, it may be desirable to increase the blood flow in a blood vessel to treat a condition or a disease associated with a decrease in blood flow, such as peripheral vascular disease, Raynaud's disease, coronary artery disease, cerebrovascular disease, etc. In various embodiments, this is accomplished by modifying the duty cycle of the stimulation algorithm such that the electrical stimulation is delivered to the blood vessel at a duty-cycle of >25% and on >25% of the days the therapy is delivered.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

All headings are for the convenience of the reader and should not be used to limit the meaning of the text that follows the heading, unless so specified.

What is claimed is:

1. A method of controlling a hemorrhage in an artery or vein of an upper limb of a patient in advance of a planned surgical procedure, the method comprising:

initiating the surgical procedure in an upper limb of the patient;

arranging the at least one electrode at a location proximate a surface of the patient's artery or vein, wherein said artery is at least one of a subclavian artery, an axillary artery, a deep brachial artery, a brachial artery, a radial artery, an ulnar artery, a deep palmar arch, and a superficial palmar arch or said vein is at least one of subclavian vein, axillary vein, cephalic vein, brachial vein, radial vein, ulnar vein, deep palmar arch, superficial palmar arch, basilic vein, median cubital vein, and median antebrachial vein and wherein said location is at least 1 cm upstream from a location of the anticipated hemorrhage, before the hemorrhage develops;

connecting said at least one electrode to a pulse generator;

identifying the hemorrhage during said surgical procedure; and causing the pulse generator to generate an electrical stimulus administered to the artery or the vein through the at least one electrode, wherein the electrical stimulus has a pulse duration, a pulse amplitude, and a pulse frequency and wherein said pulse duration, said pulse amplitude, and said pulse frequency are selected such that the electrical stimulus is effective to cause vasoconstriction in said artery or said vein and thereby prevent said hemorrhage.

2. The method of claim 1 wherein the pulse duration ranges from 1 μsec to 500 msec, the pulse amplitude ranges from 1 V to 250 V, and the pulse frequency ranges from 1 Hz to 100 kHz.

3. The method of claim 1 wherein the at least one electrode is at least one of a cuff electrode and a clamp electrode and wherein arranging the at least one electrode comprises placing said cuff electrode or said clamp electrode in direct physical contact with said location.

4. The method of claim 1 wherein a radio-frequency (RF) receiver is coupled to said at least one electrode and a RF transmitter is coupled to said pulse generator and in wireless communication with said RF receiver and wherein said method further comprises causing the pulse generator to generate, and wirelessly transmit, an electrical stimulus from the RF transmitter to the RF receiver to be administered by said at least one electrode.

5. The method of claim 1 further comprising using a microprocessor operably connected to the pulse generator to selectively set said pulse duration, said pulse amplitude, and said pulse frequency.

6. The method of claim 1, wherein the generated electrical stimulus is administered for a predefined period of time.

7. The method of claim 6, wherein the predefined period of time is at least 30 seconds.

8. The method of claim 1, wherein the generated electrical stimulus is administered for at least 10 seconds during the surgical procedure.

* * * * *